(12) United States Patent
Gold et al.

(10) Patent No.: US 8,426,198 B2
(45) Date of Patent: Apr. 23, 2013

(54) IN VITRO DIFFERENTIATED CELL AND HUMAN EMBRYONIC STEM CELL POPULATION

(75) Inventors: Joseph D. Gold, San Francisco, CA (US); Jane S. Lebkowski, Portola Valley, CA (US)

(73) Assignee: Geron Corporation, Menlo Park, CA (US)

( * ) Notice: Subject to any disclaimer, the term of this patent is extended or adjusted under 35 U.S.C. 154(b) by 52 days.

(21) Appl. No.: 11/359,341

(22) Filed: Feb. 21, 2006

(65) Prior Publication Data

US 2006/0134782 A1 Jun. 22, 2006

Related U.S. Application Data

(63) Continuation of application No. 10/141,220, filed on May 7, 2002, now abandoned, which is a continuation-in-part of application No. 09/783,203, filed on Feb. 13, 2001, now Pat. No. 6,576, 464.

(60) Provisional application No. 60/253,443, filed on Nov. 27, 2000, provisional application No. 60/253,357, filed on Nov. 27, 2000.

(51) Int. Cl.
  *C12N 5/071* (2010.01)
  *C12N 15/00* (2006.01)

(52) U.S. Cl.
  USPC ............................................ 435/366; 435/455

(58) Field of Classification Search .................. None
  See application file for complete search history.

(56) References Cited

U.S. PATENT DOCUMENTS

| | | | |
|---|---|---|---|
| 4,959,313 A | 9/1990 | Taketo | |
| 5,068,191 A | 11/1991 | Clausen et al. | |
| 5,082,670 A | 1/1992 | Gage et al. | |
| 5,326,857 A | 7/1994 | Yamamoto et al. | |
| 5,523,226 A | 6/1996 | Wheeler | |
| 5,631,236 A | 5/1997 | Woo et al. | |
| 5,639,613 A | 6/1997 | Shay et al. | |
| 5,639,618 A * | 6/1997 | Gay | 435/7.21 |
| 5,672,499 A | 9/1997 | Anderson et al. | |
| 5,716,411 A | 2/1998 | Orgill et al. | |
| 5,736,396 A | 4/1998 | Bruder et al. | |
| 5,750,397 A | 5/1998 | Tsukamoto et al. | |
| 5,759,793 A | 6/1998 | Schwartz et al. | |
| 5,766,948 A | 6/1998 | Gage et al. | |
| 5,843,780 A * | 12/1998 | Thomson | 435/363 |
| 5,851,832 A | 12/1998 | Weiss et al. | |
| 5,942,435 A | 8/1999 | Wheeler | |
| 5,968,829 A | 10/1999 | Carpenter | |
| 6,015,671 A | 1/2000 | Field | |
| 6,087,168 A | 7/2000 | Levesque et al. | |
| 6,090,622 A | 7/2000 | Gearhart et al. | |
| 6,117,985 A | 9/2000 | Thomas et al. | |
| 6,146,888 A | 11/2000 | Smith et al. | |
| 6,200,806 B1 | 3/2001 | Thomson | |
| 6,204,431 B1 | 3/2001 | Prieto et al. | |
| 6,458,589 B1 * | 10/2002 | Rambhatla et al. | 435/370 |
| 6,576,464 B2 | 6/2003 | Gold et al. | |
| 6,921,665 B2 | 7/2005 | McWhir et al. | |
| 2003/0017589 A1 * | 1/2003 | Mandalam et al. | 435/366 |

FOREIGN PATENT DOCUMENTS

| | | |
|---|---|---|
| GB | 2321642 B | 9/2000 |
| GB | 2379447 A | 3/2003 |
| WO | WO 94/02593 | 2/1994 |
| WO | WO 94/02593 A1 | 2/1994 |
| WO | WO 94/24274 A1 | 10/1994 |
| WO | WO 96/07732 A1 | 3/1996 |
| WO | WO 96/29395 A1 | 9/1996 |
| WO | WO 97/23635 A1 | 7/1997 |
| WO | WO 97/32025 A1 | 9/1997 |
| WO | WO 98/08556 A1 | 3/1998 |
| WO | WO 98/14593 A2 | 4/1998 |
| WO | WO 98/16634 A1 | 4/1998 |
| WO | WO 98/33387 A1 | 8/1998 |
| WO | WO 98/39427 A2 | 9/1998 |
| WO | WO 99/01552 A1 | 1/1999 |
| WO | WO 99/10535 A1 | 3/1999 |
| WO | WO 99/19469 A1 | 4/1999 |
| WO | WO 99/20741 A1 | 4/1999 |
| WO | WO 99/27076 A1 | 6/1999 |
| WO | WO 99/33998 A2 | 7/1999 |
| WO | WO 99/45100 A1 | 9/1999 |
| WO | WO 99/53022 A2 | 10/1999 |
| WO | WO 99/63061 A1 | 12/1999 |
| WO | WO 00/15764 A2 | 3/2000 |
| WO | WO 00/18885 A1 | 4/2000 |
| WO | WO 00/46355 A2 | 8/2000 |
| WO | WO 01/11011 A2 | 2/2001 |
| WO | WO 01/51616 A2 | 7/2001 |
| WO | WO 01/88104 A2 | 11/2001 |

(Continued)

OTHER PUBLICATIONS

Khamsi, Geneticists hail variety show, Map of DNA differences will help experts tailor drugs, Nature, Oct. 26, 2005 (online, two pages).*

(Continued)

*Primary Examiner* — Deborah Crouch
(74) *Attorney, Agent, or Firm* — Law Office of Salvatore Arrigo and Scott Lee, LLP

(57) ABSTRACT

This invention provides a system for producing differentiated cells from a stem cell population for use wherever a relatively homogenous cell population is desirable. The cells contain an effector gene under control of a transcriptional control element (such as the TERT promoter) that causes the gene to be expressed in relatively undifferentiated cells in the population. Expression of the effector gene results in depletion of undifferentiated cells, or expression of a marker that can be used to remove them later. Suitable effector sequences encode a toxin, a protein that induces apoptosis; a cell-surface antigen, or an enzyme (such as thymidine kinase) that converts a prodrug into a substance that is lethal to the cell. The differentiated cell populations produced according to this disclosure are suitable for use in tissue regeneration, and non-therapeutic applications such as drug screening.

11 Claims, 13 Drawing Sheets

FOREIGN PATENT DOCUMENTS

| WO | WO 02/42445 A2 | 5/2002 |
| WO | WO 02/42445 A3 | 5/2002 |
| WO | WO 02/61033 A2 | 8/2002 |

OTHER PUBLICATIONS

Li, R-K. et al, Isolation of Cardiomyocytes from human myocardium for primary cell culture, J. Tiss. Cult. Meth. 15: 147-154, 1993.*

Kobayashi et al., A novel strategy for the negative selection in mouse embryonic stem cells operated with immunotoxin-mediated cell targeting, Nucleic Acids Res. 24(18): 3653-3655, 1996.*

Bauer et al., Neuronal stem cells in adults. Exp Gerontol. 41(2):111-6, 2006.*

Armstrong et al., mTert expression correlates with telomerase activity during the differentiation of murine embryonic stem cells. Mech Dev. 97(1-2):109-16, 2000.*

Lee et al., Stimulation of Oct-4 activity by Ewing's sarcoma protein. Stem Cells. 23(6):738-51, 2005.*

Autexier et al., The structure and function of telomerase reverse transcriptase. Annu Rev Biochem. 75:493-517, 2006.*

Cong et al., The human telomerase catalytic subunit hTERT: organization of the gene and characterization of the promoter., Hum Mol Genet. 8(1):137-42, 1999.*

Abuljadayel, I., "Induction of stem cell-like plasticity in mononuclear cells derived from unmobilised adult human peripheral blood," *Curr. Med. Res. Opinion* 19(5):355-75 (2003).

Amit, M. et al., "Clonally Derived Human Embryonic Stem Cell Lines Maintain Pluripotency and Proliferative Potential for Prolonged Periods of Culture," *Dev. Biol.* 227:271-78 (2000).

Auerbach, J. et al., "Transplanted CNS stem cells form functional synapses in vivo," *Eur. J. Neurosci.* 12:1696-704 (2000).

Bradley, J. et al., "Stem cell medicine encounters the immune system," *Nat. Rev. Immunol.* 2:859-71 (2002).

Brandau, S. et al., "Perforin-mediated Lysis of Tumor Cells by *Mycobacterium Bovis Bacillus Calmette-Guerin*-Activated Killer Cells," *Clin. Cancer Res.* 6:3729-38 (2000).

Brüstle, O. et al., "Embryonic stem cell-derived glial precursors: A source of myelinating transplants," *Science* 285:754-56 (1999).

Clausen, H. et al., "Carbohydrates of the cell surface: Molecular aspects of glycosyltransferases and their genes," *APMIS* 100(Suppl. 27)9-17 (1992).

Cruz, I. et al., "Lack of MHC Class I Surface Expression on Neoplastic Cells and Poor Activation of the Secretory Pathway of Cytotoxic Cells in Oral Squamous Cell Carcinomas," *Br. J. Cancer* 81:881-89 (1999).

D'Ippolito, G. et al., "Marrow-isolated adult multilineage inducible (MIAMI) cells, a unique population of postnatal young and old human cells with extensive expansion and differentiation potential," *J. Cell. Sci.* 117:2971-81 (2004).

Dyce, P. et al., "Stem cells with multilineage potential derived from porcine skin," *Biochem. Biophys. Res. Comm.* 316:651-58 (2004).

Forsyth, N. et al, "Telomerase and differentiation in multicellular organisms: Turn it off, turn it on, and turn it off again," *Differentiation* 69:188-97 (2002).

Galili, U. et al., "Man, apes, and Old World monkeys differ from other mammals in the expression of alpha-galactosyl epitopes on nucleated cells," *J. Biol. Chem.* 263:17755-62 (1988).

Gammaitoni, L. et al., "Elevated telomerase activity and minimal telomere loss in cord blood long-term cultures with extensive stem cell replication," *Blood* 103(12):4440-48 (2004).

Goolsby, J. et al., "Hematopoetic progenitors express neural genes," *PNAS* 100(25):14926-31 (2003).

Gorelik, E. et al., "On the role of cell surface carbohydrates and their binding proteins (lectins) in tumor metastasis," *Cancer Metastatis Rev.* 20:245-77 (2001).

Gu, J. et al., "Tumor-Specific Transgene Expression From the Human Telomerase Reverse Transcriptase Promoter Enables Targeting of the Therapeutic Effects of the Bax Gene to Cancers," *Cancer Res.* 60(19):5359-64 (2000).

Hashimoto, N. et al., "Bone marrow-derived progenitor cells in pulmonary fibrosis," *J. Clin. Invest.* 113(2):243-52 (2004).

Hodes, R. et al., "Telomeres in T and B cells," *Nat. Rev. Immunol.* 2:699-706 (2002).

Horikawa, I. et al., "Cloning and Characterization of the Promoter Region of *Human Telomerase Reverse Transcriptase* Gene," *Cancer Res.* 59:826-30 (1999).

Inverardi, L. et al., "Human natural killer lymphocytes directly recognize evolutionarily conserved oligosaccharide ligands expressed by xenogeneic tissues," *Transplantation* 63:1318-30 (1997).

Itskovitz-Eldor, J. et al., "Differentiation of Human Embryonic Stem Cells into Embryoid Bodies Comprising the Three Embryonic Germ Layers," *Molec. Med.* 6(2):88-95 (2000).

Keller, G., "In Vitro Differentiation of Embryonic Stem Cells," *Cell Biol.* 7:862-869 (1995).

Klug, M. et al., "Genetically selected cardiomyocytes from differentiating embryonic stem cells form stable intracardiac grafts," *J. Clin. Invest.* 98:216-24 (1996).

Koga, S., et al., "A Novel Telomerase-Specific Gene Therapy: Gene Transfer of Caspase-8 Utilizing the Human Telomerase Catalytic Subunit Gene Promoter," *Human Gene Therapy* 11:1397-1406 (2000).

Liu, T. et al., "Regulation of telomerase activity in rat lung fibroblasts," *Am. J. Respir. Cell Mol. Biol.* 26:534-40 (2002).

Mattson, M. et al., "Assessing the involvement of telomerase in stem cell biology," *Meth. Molec. Biol.* 198:125-36 (2002).

Moore, J. et al., "The corneal epithelial stem cell," *DNA Cell Biol.* 21(5/6):443-51 (2002).

Murasawa, S. et al., "Constitutive human telomerse reverse transcriptase expression enhances regenerative properties of endothelial progenitor cells," *Circulation* 106:1133-39 (2002).

Oh, H. et al., "Cardiac muscle plasticity in adult and embryo by heart-derived progenitor cells," *Ann. N.Y. Acad. Sci.* 1015:182-89 (2004).

Parsch, D. et al., "Telomere length and telomerase activity during expansion and differentiation of human mesenchymal stem cells and chondrocytes," *J. Mol. Med.* 82(1):49-55 (2004).

Pesce, M. & Schöler, H., "*Oct-4*: Gatekeeper in the beginnings of mammalian development," *Stem Cells* 19:271-78 (2001).

Planz, B. et al., "Studies on the differentiation pathway and growth characteristics of epithelial culture cells of the human prostate," *Prostate Cancer Prostatic Dis.* 7:73-83 (2004).

Pochampally, R. et al., "Serum deprivation of human marrow stromal cells (hMSCs) selects for a subpopulation of early progenitor cells with enhanced expression of *OCT-4* and other embryonic genes," *Blood* 103(5):1647-52 (2004).

Prowse, K., "Detection of Telomerase Activity in Neural Cells," *Meth. Mol. Biol.* 198:137-47 (2002).

Reim, G. et al., "The POU domain protein Spg (Pou2/Oct4) is essential for endoderm formation in cooperation with the HMG domain protein Casanova," *Dev. Cell* 6:91-101 (2004).

Reubinoff, B. et al., "Embryonic stem cell lines from human blastocysts: Somatic differentiation in vitro," *Nat. Biotech.* 18:399-404 (2000).

Rubin, H., "Promise and problems in relating cellular senescence in vitro to aging in vivo," *Arch. Gerontol. Geriat.* 34:275-86 (2002).

Scholer, H., "Octamania: The POU Factors in Murine Development," *Trends Genet.* 7(10):323-329 (1991).

Schuldiner, M. et al., "Effects of eight growth factors on the differentiation of cells derived from human embryonic stem cells," *Proc. Natl. Acad. Sci. USA* 97:11307-12 (2000).

Seruya, M. et al., "Clonal population of adult stem cells: Life span and differentiation potential," *Cell. Transplant.* 13:93-101 (2004).

Shamblott, M. et al., "Derivation of pluripotent stem cells from cultured human primordial germ cells," *Proc. Natl. Acad. Sci. USA* 95:13726-31 (1998).

Swynghedauw, B., "Are adult cardiocytes still able to proliferate?" *Arch. Mal. Coeur* 96(12):1225-30 (2003).

Szyper-Kravitz, M. et al., "Granulocyte colony-stimulating factor administration upregulates telomerase activity in CD34$^+$ haematopoietic cells and may prevent telomere attrition after chemotherapy," *Br. J. Haematol.* 120:329-36 (2003).

Tabilio, A. et al., "Expression of SSEA-I antigen (3-fucosyl-*N*-acetyl-lactosamine) on normal and leukaemic human haematopoietic cells: modulation by neuraminidase treatment," *Br. J. Haematol.* 58:697-710 (1984).

Tang, D. et al., "Lack of replicative senescence in cultured rat oligodendrocyte precursor cells," *Science* 291:868-71 (2001).

Tavernarakis, N. et al., "Heritable and Inducible Genetic Interference by Double-Stranded RNA Encoded by Transgenes," *Nat. Genet.* 24:180-83 (2000).

Thiem, J., "Substrate specificity and synthetic use of glycosyltransferases," *Ernst Schering Res. Found. Workshop* 44:75-94 (2004).

Thomson, J. et al., "Isolation of a primate embryonic stem cell line," *Proc. Natl. Acad. Sci. USA* 92:7844-48 (1995).

Thomson, J., "Embryonic stem cell lines derived from human blastocysts," *Science* 282:1145-7 (1998).

Tsai, M-S. et al., "Isolation of human multipotent mesenchymal stem cells from second-trimester amniotic fluid using a novel two-stage culture protocol," *Hum. Reprod.* 19(6):1450-56 (2004).

Villa, A. et al., "Long-term molecular and cellular stability of human neural stem cell lines," *Exp. Cell Res.* 294:559-70 (2004).

Yui, J. et al., "Telomerase activity in candidate stem cells from fetal liver and adult bone marrow," *Blood* 91(9):3255-62 (1998).

Okano, H. & Agata, K., "Stem Cells and Regeneration," *Saiboukougaku* 19(3):368-74 (2000). Japanese laguage document, Only title, legends of Figures 1 and 3 are in English.

Sharma, A. et al., "Reduction in the level of Gal($\alpha$1,3)Gal in transgenic mice and pigs by the expression of an $\alpha$(1,2)fucosyltransferase," *Proc. Natl. Acad. Sci. USA* 93:7190-5 (1996).

Herget, T. et al., "Retinoic acid induces apoptosis-associated neural differentiation of a murine teratocarcinoma cell line," *J. Neurochem.* 70(1):47-58 (1998).

Bestilny, L. et al., "Selective inhibition of telomerase activity during terminal differentiation of immortal cell lines," *Cancer Res.* 56:3796-802 (1996).

Savoysky, E. et al., "Down-regulation of telomerase activity is an early event in the differentiation of HL60 cells," *Biochem. Biophys. Res. Commun.* 226:329-34 (1996).

Sharma, H. et al., "Differentiation of immortal cells inhibits telomerase activity," *Proc. Natl. Acad. Sci. USA* 92:12343-6( 1995).

Tzukerman, M. et al., "Identification of a novel transcription factor binding element involved in the regulation by differentiation of the human telomerase (hTERT) promoter," *Mol. Biol. Cell* 11(12):4381-91 (2000).

Lim, J. et al., "Proteosome analysis of conditioned medium from mouse embryonic fibroblast feeder layers which support the growth of human embryonic stem cells", *Proteomics 2*, (2002),pp. 1187-203.

Owen-Smith, J. et al., "An international gap in human ES cell research", *Nature Biotechnol.* 24(4), (2006),pp. 391-392.

Robertson, D. "NIH sacrifices commercial rights in WiCell deal", *Nature Biotechnol.* 19, (2001),p. 1001.

Scott, C. et al., "And then there were two: use of hESC lines", *Nature Biotechnol.* 27(8), (2009),pp. 696-697.

Wertz, D. "Embryo and stem cell research in the United States: History and politics", *Gene Ther.* 9(11), (2002),pp. 674-678.

\* cited by examiner

Transgene expression cassette for
hTERT-promoter/TK/Adenovirus Plasmid

A.

B.

IN VITRO DIFFERENTIATED CELL AND HUMAN EMBRYONIC STEM CELL POPULATION

REFERENCE TO RELATED APPLICATIONS

This application is a continuation of U.S. patent application Ser. No. 10/141,220, filed May 7, 2002 now abandoned, which is a continuation-in-part of U.S. patent application Ser. No. 09/783,203, filed Feb. 13, 2001 (now U.S. Pat. No. 6,576,464), which claims priority to U.S. provisional applications 60/253,443 and 60/253,357, both filed Nov. 27, 2000 (expired). The priority applications are hereby incorporated herein by reference in their entirety, as is International Patent Publication WO 02/042445.

TECHNICAL FIELD

This invention relates generally to the field of cell biology of embryonic cells, and the molecular biology of promoter controlled viral vectors. More specifically, it describes a technology for removing undifferentiated cells from populations derived from pluripotent stem cells using selectively expressed lytic vectors.

BACKGROUND

Precursor cells have become a central interest in medical research. Many tissues in the body have a back-up reservoir of precursors that can replace cells that are senescent or damaged by injury or disease. Considerable effort has been made recently to isolate precursors of a number of different tissues for use in regenerative medicine.

U.S. Pat. No. 5,750,397 (Tsukamoto et al., Systemix) reports isolation and growth of human hematopoietic stem cells which are Thy-1+, CD34+, and capable of differentiation into lymphoid, erythroid, and myelomonocytic lineages. U.S. Pat. No. 5,736,396 (Bruder et al.) reports methods for lineage-directed differentiation of isolated human mesenchymal stem cells, using an appropriate bioactive factor. The derived cells can then be introduced into a host for mesenchymal tissue regeneration or repair.

U.S. Pat. No. 5,716,411 (Orgill et al.) proposes regenerating skin at the site of a burn or wound, using an epithelial autograft. U.S. Pat. No. 5,766,948 (F. Gage) reports a method for producing neuroblasts from animal brain tissue. U.S. Pat. No. 5,672,499 (Anderson et al.) reports obtaining neural crest stem cells from embryonic tissue. U.S. Pat. No. 5,851,832 (Weiss et al., Neurospheres) reports isolation of putative neural stem cells from 8-12 week old human fetuses. U.S. Pat. No. 5,968,829 (M. Carpenter) reports human neural stem cells derived from primary central nervous system tissue.

U.S. Pat. No. 5,082,670 (F. Gage) reports a method for grafting genetically modified cells to treat defects, disease or damage of the central nervous system. Auerbach et al. (Eur. J. Neurosci. 12:1696, 2000) report that multipotential CNS cells implanted into animal brains form electrically active and functionally connected neurons. Brustle et al. (Science 285:754, 1999) report that precursor cells derived from embryonic stem cells interact with host neurons and efficiently myelinate axons in the brain and spinal cord.

Considerable interest has been generated by the development of embryonic stem cells, which are thought to have the potential to differentiate into many cell types. Early work on embryonic stem cells was done in mice. Mouse stem cells can be isolated from both early embryonic cells and germinal tissue. Desirable characteristics of pluripotent stem cells are that they be capable of proliferation in vitro in an undifferentiated state, retain a normal karyotype, and retain the potential to differentiate to derivatives of all three embryonic germ layers (endoderm, mesoderm, and ectoderm).

Development of human pluripotent stem cell preparations is considerably less advanced than work with mouse cells. Thomson et al. propagated pluripotent stem cells from lower primates (U.S. Pat. No. 5,843,780; Proc. Natl. Acad. Sci. USA 92:7844, 1995), and then from humans (Science 282:114, 1998). Gearhart and coworkers derived human embryonic germ (hEG) cell lines from fetal gonadal tissue (Shamblott et al., Proc. Natl. Acad. Sci. USA 95:13726, 1998; and U.S. Pat. No. 6,090,622).

Both hES and hEG cells have the long-sought characteristics of pluripotent stem cells: they are capable of being grown in vitro without differentiating, they have a normal karyotype, and they remain capable of producing a number of different cell types. Clonally derived human embryonic stem cell lines maintain pluripotency and proliferative potential for prolonged periods in culture (Amit et al., Dev. Biol. 227:271, 2000). These cells hold considerable promise for use in human therapy, acting as a reservoir for regeneration of almost any tissue compromised by genetic abnormality, trauma, or a disease condition.

International Patent Publication WO 99/20741 (Geron Corp.) refers to methods and materials for growing primate-derived primordial stem cells. In one embodiment, a cell culture medium is provided for growing primate-derived primordial stem cells in a substantially undifferentiated state, having a low osmotic pressure and low endotoxin levels. The basic medium is combined with a nutrient serum effective to support the growth of primate-derived primordial stem cells and a substrate of feeder cells or an extracellular matrix component derived from feeder cells. The medium can further include non-essential amino acids, an anti-oxidant, and growth factors that are either nucleosides or a pyruvate salt.

A significant challenge to the use of stem cells for therapy is to control growth and differentiation into the particular type of tissue required for treatment of each patient.

U.S. Pat. No. 4,959,313 (M. Taketo, Jackson Labs) provides a particular enhancer sequence that causes expression of a flanking exogenous or recombinant gene from a promoter accompanying the gene that does not normally cause expression in undifferentiated cells. U.S. Pat. No. 5,639,618 (D. A. Gay, Plurion Inc.) proposes a method for isolating a lineage specific stem cell in vitro, in which a pluripotent embryonic stem cell is transfected with a construct in which a lineage-specific genetic element is operably linked to a reporter gene, culturing the cell under conditions where the cell differentiates, and then separation of cells expressing the reporter are separated from other cells.

U.S. Pat. No. 6,087,168 (Levesque et. al., Cedars Sinai Med. Ctr.) is directed to transdifferentiating epidermal cells into viable neurons useful for both cell therapy and gene therapy. Skin cells are transfected with a neurogenic transcription factor, and cultured in a medium containing an antisense oligonucleotide corresponding to a negative regulator of neuronal differentiation.

International Patent Publication WO 97/32025 (McIvor et al., U. Minnesota) proposes a method for engrafting drug resistant hematopoietic stem cells. The cells in the graft are augmented by a drug resistance gene (such as methotrexate resistant dihydrofolate reductase), under control of a promoter functional in stem cells. The cells are administered into a mammal, which is then treated with the drug to increase engraftment of transgenic cells relative to nontransgenic cells.

International Patent Publication WO 98/39427 (Stein et al., U. Massachusetts) refers to methods for expressing exogenous genes in differentiated cells such as skeletal tissue. Stem cells (e.g., from bone marrow) are contacted with a nucleic acid in which the gene is linked to an element that controls expression in differentiated cells. Exemplary is the rat osteocalcin promoter. International Patent Publication WO 99/10535 (Liu et al., Yale U.) proposes a process for studying changes in gene expression in stem cells. A gene expression profile of a stem cell population is prepared, and then compared a gene expression profile of differentiated cells.

International Patent Publication WO 99/19469 (Braetscher et al., Biotransplant) refers to a method for growing pluripotent embryonic stem cells from the pig. A selectable marker gene is inserted into the cells so as to be regulated by a control or promoter sequence in the ES cells, exemplified by the porcine OCT-4 promoter.

International Patent Publication WO 00/15764 (Smith et al., U. Edinburgh) refers to propagation and derivation of embryonic stem cells. The cells are cultured in the presence of a compound that selectively inhibits propagation or survival of cells other than ES cells by inhibiting a signaling pathway essential for the differentiated cells to propagate. Exemplary are compounds that inhibit SHP-2, MEK, or the ras/MAPK cascade.

Klug et al. (J. Clin. Invest. 98:216, 1996) propose a strategy for genetically selecting cardiomyocytes from differentiating mouse embryonic stem cells. A fusion gene consisting of the α-cardiac myosin heavy chain promoter and a cDNA encoding aminoglycoside phosphotransferase was stably transfected into the ES cells. The resulting lines were differentiated in vitro and selected using G418. The selected cardiomyocyte cultures were reported to be highly differentiated. When engrafted back into mice, ES-derived cardiomyocyte grafts were detectable as long as 7 weeks after implantation.

Schuldiner et al. (Proc. Natl. Acad. Sci. USA 97:11307, 2000) report the effects of eight growth factors on the differentiation of cells from human embryonic stem cells. After initiating differentiation through embryoid body formation, the cells were cultured in the presence of bFGF, TGF-β1, activin-A, BMP-4, HGF, EGF, βNGF, or retinoic acid. Each growth factor had a unique effect on the differentiation pathway, but none of the growth factors directed differentiation exclusively to one cell type.

There is a need for new approaches to generate populations of differentiated cells suitable for human administration.

SUMMARY OF THE INVENTION

This invention provides a system for depleting relatively undifferentiated cells from a heterogeneous cell population, such as may be obtained by differentiation of stem cells. The population is treated with a vector that puts a lethal or potentially lethal effector gene under control of a gene element that allows the gene to be expressed at a higher level in the undifferentiated subpopulation. This produces a population relatively enriched for mature cells, and suitable for use in regenerative medicine.

One embodiment of this invention is a population of cells differentiated from stem cells cultured ex vivo, which is essentially free of undifferentiated cells. Exemplary are pluripotent stem cells of primate origin, such as human embryonic stem cells.

Cells in the population can contain or be derived using a polynucleotide comprising the structure P-X, where X is a nucleic acid sequence that is lethal to a cell in which it is expressed, or renders a cell in which it is expressed susceptible to a lethal effect of an external agent; and P is a transcriptional control element that causes X to be preferentially expressed in undifferentiated cells. The connecting line in P-X indicates that the genetic elements are operatively linked, whether or not they are adjacent in the nucleic acid molecule.

X is referred to in the description that follows as an effector sequence. X can encode a toxin, a protein that induces or mediates apoptosis, or an enzyme (such as thymidine kinase) that converts a prodrug (such as ganciclovir) to a compound that is lethal to a cell in which X is expressed. Other examples are provided later in this disclosure.

In certain embodiments, P-X is an introduced heterologous molecule, meaning that the cell or its ancestors was genetically altered with a vector comprising P-X. In other embodiments the cell or its ancestors was genetically altered with a vector to place X under control of an endogenous transcriptional control element. Following transfection, X can be either transiently expressed in undifferentiated cells in the population, or P-X can be inheritable and expressed in undifferentiated progeny. Non-limiting examples for P include the OCT-4 promoter, and the promoter of telomerase reverse transcriptase (TERT). The cells can also contain a drug resistance gene Y under control of P, depicted in this disclosure as P-X-Y, indicating a functional relationship where P regulates transcription of both X and Y, with the elements being in any orientation in the sequence that links the functions in this manner.

Another embodiment of the invention is a stem cell genetically altered so as to contain a nucleic acid with the structure P-X, as already described. The invention also provides polynucleotide vectors adapted to genetically alter stem cells in this fashion.

Another embodiment of the invention is a method of producing a population of differentiated cells. A cell population comprising undifferentiated stem cells that contain a nucleic acid molecule comprising the structure P-X is treated to cause at least some undifferentiated cells in the population to differentiate.

Another embodiment of the invention is a method for depleting undifferentiated stem cells from a cell population. Stem cells in the population are genetically altered so that they contain a nucleic acid molecule comprising the structure P-X as already described. In this way, a gene that is lethal to a cell in which it is expressed, or renders it susceptible to a lethal effect of an external agent, is placed under control of a transcriptional control element that causes the gene to be preferentially expressed in undifferentiated cells. The cell population can be genetically altered when it is still predominantly undifferentiated (before being caused to differentiate), or when it already predominantly comprises differentiated cells.

If X is lethal to the cell, then undifferentiated stem cells can be depleted simply by culturing the cell population under conditions where X is expressed. If X renders the cell susceptible to lethal effects of an external agent (such as a drug or prodrug), then undifferentiated stem cells are depleted by combining the cells with the external agent. This can be done by contacting the cells in vitro with the agent in tissue culture, or administering the cells to the subject simultaneously or sequentially with the external agent, if not already present.

The reagents and techniques of this invention can be brought to bear on cell populations containing any type of stem cells. They are especially suited for application to primate pluripotent stem cells, such as human embryonic stem cells.

Other embodiments of the invention will be apparent from the description that follows.

The Upper Panel is a bar graph showing the number of cells surviving in culture. Treatment with $T_{PAC}$+GCV eliminated cells cultured under each condition. In each instance, culture of the surviving cells produced populations that appeared highly differentiated and substantially free of undifferentiated morphology. The Lower Panel is a half-tone reproduction of a gel showing RT-PCR analysis of the surviving cells. Those cells cultured with conditioned medium (mEF-CM) or DMSO had no detectable OCT-4 expression, while 2 out of 4 samples treated with retinoic acid (RA) showed amplification products consistent with very low levels of OCT-4 expression.

Figure 10:
Figure 10:

FIG. 10 is a reproduced micrograph of an hES cell line that has been transduced by combining with a control adenovirus vector (Panel A), or pGRN376 (Panel B), which contains the tk gene under control of the TERT promoter. Both wells of transduced cells were cultured for 3 days in a medium containing ganciclovir. Undifferentiated colonies typical of normal hES cell cultures were seen in the control wells. In the wells treated with pGRN376, most or all undifferentiated ES cell colonies were gone, and only differentiated cells remained.

Figure 11:
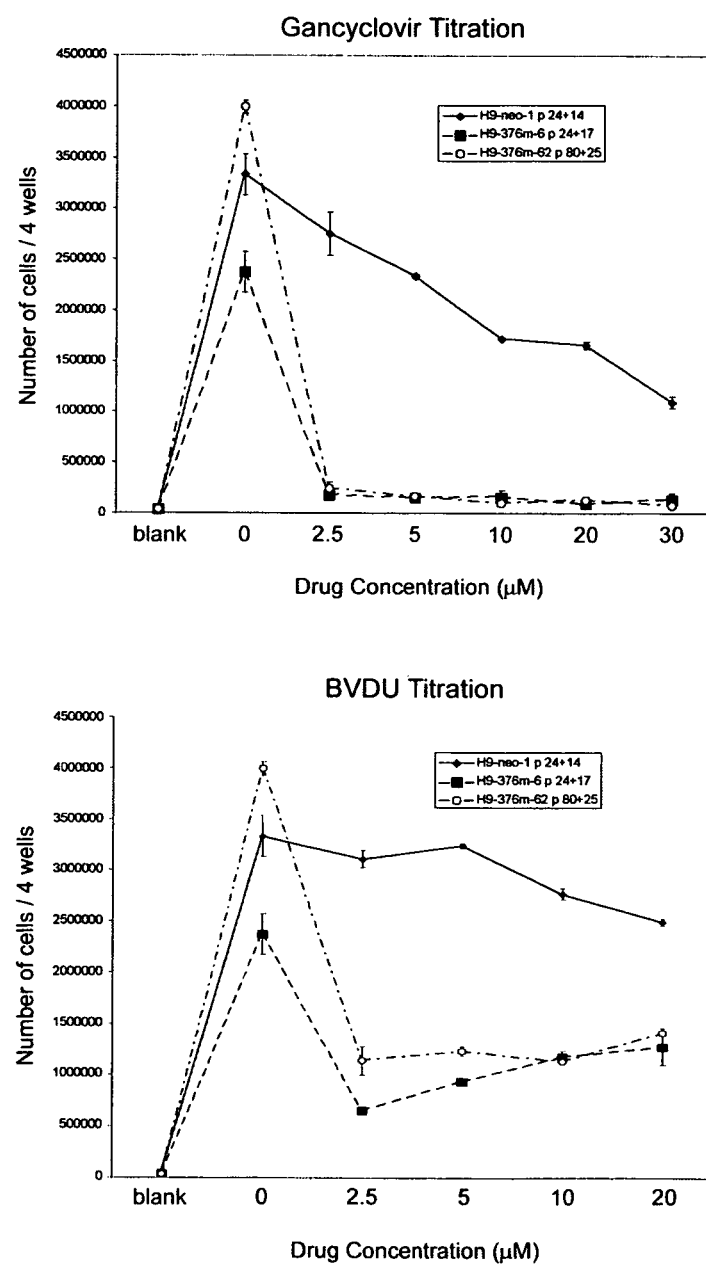

FIG. 11 is a two-panel line graph, showing drug sensitivity of undifferentiated cells containing the telomerase promoter driven thymidine kinase gene ($T_{PAC}$). Upper and lower panels show sensitivity to the prodrugs ganciclovir (GCV) and (E)-5-(2-bromovinyl)-2'-deoxyuridine (BVDU), respectively. Ganciclovir at a concentration as low as 2.5 µM kills virtually all of the undifferentiated $T_{PAC}$ ES cells within ~4 days.

Figure 12A:
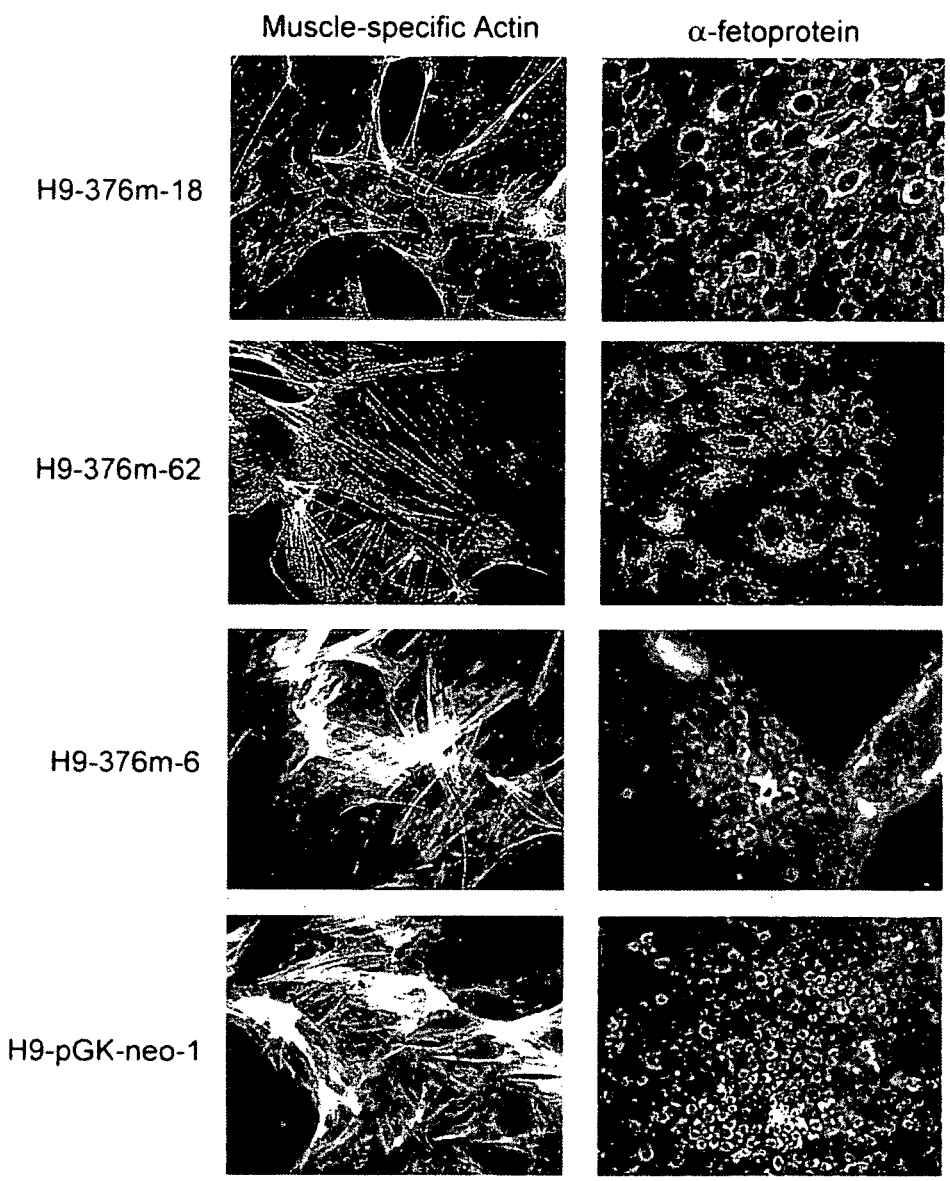

FIGS. 12(A) and (B) comprises black-and-white reproductions of fluorescence micrographs of differentiated ES cells. Cell lines H9-376m-18, H9-376m-62, and H9-376m-6 contain the $T_{PAC}$ gene; H9-pGK-neo-1 is the control cell line transfected only with the drug selection plasmid. The stably transfected cells were differentiated into embryoid bodies, and plated for immunocytochemistry analysis. A least three of the $T_{PAC}$ containing stem cell lines show areas that stain for muscle specific actin, α-fetoprotein, ⊕-tubulin, and cardiac troponin 1, representative of all three embryonic germ layers.

DETAILED DESCRIPTION OF THE INVENTION

Stem cells of various kinds have become an extremely attractive modality in regenerative medicine. They can be proliferated in culture, and then differentiated in vitro or in situ into the cell types needed for therapy. Recently, it has been demonstrated that human embryonic stem cells continuously express a high level of telomerase, enabling them to maintain telomere length and grow almost indefinitely in culture.

So far, efforts to differentiate stem cells have been directed primarily towards identifying culture conditions that promote outgrowth of a cell population with phenotypic features of a tissue type desirable for regenerative medicine. Schuldiner et al. (supra) report the effects of growth factors on the differentiation of human embryonic stem cells. In U.S. Pat. No. 5,639,613, stem cells are transfected with a lineage-specific gene that is operably linked to a reporter gene, which is then used to select for cells expressing the reporter. In WO 97/32025, hematopoietic stem cells are augmented by a drug resistance gene, and then engrafted into a subject. The cells are administered into a mammal, which is then treated with the drug to increase engraftment of transgenic cells. Klug et al. (supra) used a construct in which the α-cardiac myosin heavy chain promoter controlled expression of aminoglycoside phosphotransferase. Transfected differentiated cells were selected using G418, which produced lines of cardiomyocyte like cells. This is a positive selection strategy that uses gene expression patterns of the desired tissue type to allow preferential survival of differentiated tissue.

It is a hypothesis of this invention that some of the populations of differentiated cells produced using adaptive culture and positive selection methods will be suboptimal for use in human therapy. In some circumstances, undifferentiated cells in the population may impair engraftment or function of the cells in vivo. Undifferentiated cells may also increase the possibility of a malignancy or other tumor forming at the site of the therapeutic implant, or by migration of transplanted cells.

This invention is directed towards a strategy in which undifferentiated cells remaining in such differentiated cell populations can be depleted. This is effected by genetically altering the cells, so that a gene that is lethal to a cell in which it is expressed, or renders it susceptible to a lethal effect of an external agent, is placed under transcriptional control of a genetic element that causes it to be expressed preferentially in any undifferentiated cells in the population. This is a negative selection strategy, designed to minimize the proportion of undifferentiated cells. It is possible to combine this technique with positive selection techniques of various kinds, in order to obtain relatively pure populations of the desired tissue type that are essentially free of undifferentiated cells.

As a non-limiting validation of the invention, human embryonic stem (hES) cells have been transduced with an adenovirus vector ($T_{PAC}$) in which a herpes virus thymidine kinase gene was placed under control of a promoter sequence for human telomerase reverse transcriptase (hTERT). hES cells constitutively express hTERT, but this ability is lost upon differentiation. Example 10 (FIGS. 6-8) show that transduction of hES cells with $T_{PAC}$ vector renders undifferentiated cells susceptible to lethality by the prodrug ganciclovir, a substrate for thymidine kinase, at a concentration of ~20 µM. Example 11 (FIG. 9) shows that when hES cells are transduced with $T_{PAC}$ vector and then differentiated with DMSO, there are no surviving cells with detectable OCT-4 expression (a phenotype of undifferentiated cells).

The techniques of this invention are designed in part to provide cell populations with improved characteristics for human therapy. After depleting undifferentiated cells, the differentiated population is expected to possess better functional and engraftment characteristics, and have reduced risk of creating unwanted tissue architecture and malignancies in the treated subject. In addition, cell populations depleted of undifferentiated cells are more homogeneous, which provides a distinct advantage for non-therapeutic applications, such as producing antibody, cDNA libraries, and screening drug candidates.

DEFINITIONS

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. This invention relates to pPS cells that are not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated. Nevertheless, the undifferentiated colonies persist when the population is cultured or passaged under appropriate conditions, and individual undifferentiated cells constitute a substantial proportion of the cell population. Cultures that are substantially undifferentiated contain at least 20% undifferentiated pPS cells, and may contain at least 40%, 60%, or 80% in order of increasing preference. Whenever a culture or cell population is referred to in this disclosure as proliferating "without differentiation", what is meant is that after proliferation, the composition is substantially undifferentiated according to the preceding definition.

"Feeder cells" or "feeders" are terms used to describe cells of one type that are co-cultured with cells of another type, to provide an environment in which the cells of the second type can grow. The feeder cells are optionally from a different species as the cells they are supporting. For example, certain types of pPS cells can be supported by primary mouse embryonic fibroblasts, immortalized mouse embryonic fibroblasts, or human fibroblast-like cells differentiated from hES cells, as described later in this disclosure. pPS cell populations are said to be "essentially free" of feeder cells if the cells have been grown through at least one round after splitting in which fresh feeder cells are not added to support the growth of the pPS. Cultures essentially free of feeder cells contain less than about 5% feeder cells. Whenever a culture or cell population is referred to in this disclosure as "feeder-free", what is meant is that the composition is essentially free of feeder cells according to the preceding definition, subject only to further constraints explicitly required.

The term "embryoid bodies" is a term of art synonymous with "aggregate bodies". The terms refer to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria.

The terms "committed precursor cells", "lineage restricted precursor cells" and "restricted developmental lineage cells" all refer to cells that are capable of proliferating and differentiating into several different cell types, with a range that is typically more limited than pluripotent stem cells of embryonic origin capable of giving rise to progeny of all three germ layers. Non-limiting examples of committed precursor cells include hematopoietic cells, which are pluripotent for various blood cells; hepatocyte progenitors, which are pluripotent for bile duct epithelial cells and hepatocytes; and mesenchymal stem cells. Another example is neural restricted cells, which can generate glial cell precursors that progress to oligodendrocytes and astrocytes, and neuronal precursors that progress to neurons.

For the purposes of this description, the term "stem cell" can refer to either a pluripotent stem cell, or a committed precursor cell, both as defined above. Minimally, a stem cell has the ability to proliferate and form cells of more than one different phenotype, and is also capable of self renewal— either as part of the same culture, or when cultured under different conditions. Embryonic stem cells can be identified as positive for the enzyme telomerase.

As used in this disclosure, "differentiated" and "undifferentiated" are relative terms depending on the context in which they are used. Specifically, in reference to a particular type of self-renewing stem cell, the term "undifferentiated" refers back to the same self-renewing stem cell, whereas the term "differentiated" refers to one or more of the relatively mature phenotypes the stem cell can generate—as discernable by morphological criteria, antigenic markers, and gene transcripts they produce. Undifferentiated pPS cells have the ability to differentiate into all three germ layers. The cells differentiated from them do not, and can readily be recognized by one skilled in the art by morphological criteria.

The terms "polynucleotide" and "nucleic acid molecule" refer to a polymer of nucleotides of any length. Included are genes and gene fragments, mRNA, tRNA, rRNA, ribozymes, cDNA, recombinant polynucleotides, branched polynucleotides, plasmids, vectors, isolated DNA and RNA, nucleic acid probes, and primers. As used in this disclosure, the term polynucleotides refer interchangeably to double- and single-stranded molecules. Unless otherwise specified or required, any embodiment of the invention that is a polynucleotide encompasses both a double-stranded form, and each of the two complementary single-stranded forms known or predicted to make up the double-stranded form. Included are nucleic acid analogs such as phosporamidates and thiophosporamidates.

A cell is said to be "genetically altered", "transfected", or "genetically transformed" when a polynucleotide has been transferred into the cell by any suitable means of artificial manipulation, or where the cell is a progeny of the originally altered cell that has inherited the polynucleotide. The polynucleotide will often comprise a transcribable sequence encoding a protein of interest, which enables the cell to express the protein at an elevated level. The genetic alteration is said to be "inheritable" if progeny of the altered cell have the same alteration.

A "control element" or "control sequence" is a nucleotide sequence involved in an interaction of molecules that contributes to the functional regulation of a polynucleotide, such as replication, duplication, transcription, splicing, translation, or degradation of the polynucleotide. Transcriptional control elements include promoters, enhancers, and repressors.

Particular gene sequences referred to as promoters, like the "TERT promoter", or the "OCT-4 promoter", are polynucleotide sequences derived from the gene referred to that promote transcription of an operatively linked gene expression product. It is recognized that various portions of the upstream and intron untranslated gene sequence may in some instances contribute to promoter activity, and that all or any subset of these portions may be present in the genetically engineered construct referred to. The promoter may be based on the gene sequence of any species having the gene, unless explicitly restricted, and may incorporate any additions, substitutions or deletions desirable, as long as the ability to promote transcription in the target tissue. Genetic constructs designed for treatment of humans typically comprise a segment that is at least 90% identical to a promoter sequence of a human gene. A particular sequence can be tested for activity and specificity, for example, by operatively linking to a reporter gene (Example 9).

Genetic elements are said to be "operatively linked" if they are in a structural relationship permitting them to operate in a manner according to their expected function. For instance, if a promoter helps initiate transcription of the coding sequence, the coding sequence can be referred to as operatively linked to (or under control of the promoter. There may be intervening sequence between the promoter and coding region so long as this functional relationship is maintained.

In the context of encoding sequences, promoters, and other genetic elements, the term "heterologous" indicates that the element is derived from a genotypically distinct entity from that of the rest of the entity to which it is being compared. For example, a promoter or gene introduced by genetic engineering techniques into an animal of a different species is said to be a heterologous polynucleotide. An "endogenous" genetic element is an element that is in the same place in the chromosome where it occurs in nature, although other elements may be artificially introduced into a neighboring position.

The terms "polypeptide", "peptide" and "protein" are used interchangeably in this disclosure to refer to polymers of amino acids of any length. The polymer may comprise modified amino acids, it may be linear or branched, and it may be interrupted by non-amino acids.

General Techniques

For further elaboration of general techniques useful in the practice of this invention, the practitioner can refer to standard textbooks and reviews in cell biology, tissue culture, and embryology. Included are *Teratocarcinomas and embryonic stem cells: A practical approach* (E. J. Robertson, ed., IRL Press Ltd. 1987); *Guide to Techniques in Mouse Development* (P. M. Wasserman et al., eds., Academic Press 1993); *Embryonic Stem Cell Differentiation in Vitro* (M. V. Wiles, Meth. Enzymol. 225:900, 1993); *Properties and uses of Embryonic Stem Cells: Prospects for Application to Human Biology and Gene Therapy* (P. D. Rathjen et al., Reprod. Fertil. Dev. 10:31, 1998). Differentiation of stem cells is reviewed in Robertson, Meth. Cell Biol. 75:173, 1997; and Pedersen, Reprod. Fertil. Dev. 10:31, 1998.

Methods in molecular genetics and genetic engineering are described generally in the current editions of *Molecular Cloning: A Laboratory Manual*, (Sambrook et al.); *Oligonucleotide Synthesis* (M. J. Gait, ed.); *Animal Cell Culture* (R. I. Freshney, ed.); *Gene Transfer Vectors for Mammalian Cells* (Miller & Calos, eds.); *Current Protocols in Molecular Biology and Short Protocols in Molecular Biology, 3rd Edition* (F. M. Ausubel et al., eds.); and *Recombinant DNA Methodology* (R. Wu ed., Academic Press). Reagents, cloning vectors, and kits for genetic manipulation referred to in this disclosure are available from commercial vendors such as BioRad, Stratagene, Invitrogen, and ClonTech.

General techniques in cell culture and media collection are outlined in *Large Scale Mammalian Cell Culture* (Hu et al., Curr. Opin. Biotechnol. 8:148, 1997); *Serum-free Media* (K. Kitano, Biotechnology 17:73, 1991); *Large Scale Mammalian Cell Culture* (Curr. Opin. Biotechnol. 2:375, 1991); and *Suspension Culture of Mammalian Cells* (Birch et al., Bioprocess Technol. 19:251, 1990). Other observations about the media and their impact on the culture environment have been made by Marshall McLuhan and Fred Allen.

Sources of Stem Cells

This invention can be practiced using stem cells of various types, which may include the following non-limiting examples.

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Primary liver cell cultures can be obtained from human biopsy or surgically excised tissue by perfusion with an appropriate combination of collagenase and hyaluronidase. Alternatively, EP 0 953 633 A1 reports isolating liver cells by preparing minced human liver tissue, resuspending concentrated tissue cells in a growth medium and expanding the cells in culture. The growth medium comprises glucose, insulin, transferrin, $T_3$, FCS, and various tissue extracts that allow the hepatocytes to grow without malignant transformation. The cells in the liver are thought to contain specialized cells including liver parenchymal cells, Kupffer cells, sinusoidal endothelium, and bile duct epithelium, and also precursor cells (referred to as "hepatoblasts" or "oval cells") that have the capacity to differentiate into both mature hepatocytes or biliary epithelial cells (L. E. Rogler, Am. J. Pathol. 150:591, 1997; M. Alison, Current Opin. Cell Biol. 10:710, 1998; Lazaro et al., Cancer Res. 58:514, 1998).

U.S. Pat. No. 5,192,553 reports methods for isolating human neonatal or fetal hematopoietic stem or progenitor cells. U.S. Pat. No. 5,716,827 reports human hematopoietic cells that are Thy-1 positive progenitors, and appropriate growth media to regenerate them in vitro. U.S. Pat. No. 5,635,387 reports a method and device for culturing human hematopoietic cells and their precursors. U.S. Pat. No. 6,015,554 describes a method of reconstituting human lymphoid and dendritic cells.

U.S. Pat. No. 5,486,359 reports homogeneous populations of human mesenchymal stem cells that can differentiate into cells of more than one connective tissue type, such as bone, cartilage, tendon, ligament, and dermis. They are obtained from bone marrow or periosteum. Also reported are culture conditions used to expand mesenchymal stem cells. WO 99/01145 reports human mesenchymal stem cells isolated from peripheral blood of individuals treated with growth factors such as G-CSF or GM-CSF. WO 00/53795 reports adipose-derived stem cells and lattices, substantially free of adipocytes and red cells. These cells reportedly can be expanded and cultured to produce hormones and conditioned culture media.

The invention can be practiced using stem cells of any vertebrate species. Included are stem cells from humans; as well as non-human primates, domestic animals, livestock, and other non-human mammals.

Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells.

Media and Feeder Cells

Media for isolating and propagating pPS cells can have any of several different formulas, as long as the cells obtained have the desired characteristics, and can be propagated further. Suitable sources are as follows: Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Exemplary serum-containing ES medium is made with 80% DMEM (typically KO DMEM), 20% defined fetal bovine serum (FBS) not heat inactivated, 0.1 mM non-essential amino acids, 1 mM L-glutamine, and 0.1 mM β-mercaptoethanol. The medium is filtered and stored at 4° C. for no longer than 2 weeks. Serum-free ES medium is made with 80% KO DMEM, 20% serum replacement, 0.1 mM non-essential amino acids, 1 mM L-glutamine, and 0.1 mM β-mercaptoethanol. An effective serum replacement is Gibco #10828-028. The medium is filtered and stored at 4° C. for no longer than 2 weeks. Just before use, human bFGF is added to a final concentration of 4 ng/mL (Bodnar et al., Geron Corp, International Patent Publication WO 99/20741).

Feeder cells (where used) are propagated in mEF medium, containing 90% DMEM (Gibco #11965-092), 10% FBS (Hyclone #30071-03), and 2 mM glutamine. mEFs are propagated in T150 flasks (Corning #430825), splitting the cells 1:2 every other day with trypsin, keeping the cells subconfluent. To prepare the feeder cell layer, cells are irradiated at a dose to inhibit proliferation but permit synthesis of important factors that support hES cells (~4000 rads gamma irradiation). Six-well culture plates (such as Falcon #304) are coated by incubation at 37° C. with 1 mL 0.5% gelatin per well overnight, and plated with 375,000 irradiated mEFs per well. Feeder cell layers are typically used 5 h to 4 days after plating. The medium is replaced with fresh hES medium just before seeding pPS cells.

Conditions for culturing other stem cells are known, and can be optimized appropriately according to the cell type. Media and culture techniques for particular cell types referred to in the previous section are provided in the references cited.

Embryonic Stem Cells

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one cell human embryos can be expanded to the blastocyst stage (Bongso et al., Hum Reprod 4: 706, 1989). Human embryos are cultured to the blastocyst stage in G1.2 and G2.2 medium (Gardner et al., Fertil. Steril. 69:84, 1998). Blastocysts that develop are selected for ES cell isolation. The zona pellucida is removed from blastocysts by brief exposure to pronase (Sigma). The inner cell masses are isolated by immunosurgery, in which blastocysts are exposed to a 1:50 dilution of rabbit anti-human spleen cell antiserum for 30 minutes, then washed for 5 minutes three times in DMEM, and exposed to a 1:5 dilution of Guinea pig complement (Gibco) for 3 minutes (see Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps either by exposure to calcium and magnesium-free phosphate-buffered saline (PBS) with 1 mM EDTA, by exposure to dispase or trypsin, or by mechanical dissociation with a micropipette; and then replated on mEF in fresh medium. Dissociated cells are replated on mEF feeder layers in fresh ES medium, and observed for colony formation. Colonies demonstrating undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (without calcium or magnesium and with 2 mM EDTA), exposure to type IV collagenase (~200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8-11 weeks after the last menstrual period. Suitable preparation methods are described in Shamblott et al., Proc. Natl. Acad. Sci. USA 95:13726, 1998 and U.S. Pat. No. 6,090,622.

Briefly, genital ridges are rinsed with isotonic buffer, then placed into 0.1 mL 0.05% trypsin/0.53 mM sodium EDTA solution (BRL) and cut into <1 mm$^3$ chunks. The tissue is then pipelted through a 100 μL tip to further disaggregate the cells. It is incubated at 37° C. for ~5 min, then ~3.5 mL EG growth medium is added. EG growth medium is DMEM, 4500 mg/L D-glucose, 2200 mg/L mM sodium bicarbonate; 15% ES qualified fetal calf serum (BRL); 2 mM glutamine (BRL); 1 mM sodium pyruvate (BRL); 1000-2000 U/mL human recombinant leukemia inhibitory factor (LIF, Genzyme); 1-2 ng/ml human recombinant basic fibroblast growth factor (bFGF, Genzyme); and 10 μM forskolin (in 10% DMSO). In an alternative approach, EG cells are isolated using hyaluronidase/collagenase/DNAse. Gonadal anlagen or genital ridges with mesenteries are dissected from fetal material, the genital ridges are rinsed in PBS, then placed in 0.1 ml HCD digestion solution (0.01% hyaluronidase type V, 0.002% DNAse I, 0.1% collagenase type IV, all from Sigma prepared in EG growth medium). Tissue is minced and incubated 1 h or overnight at 37° C., resuspended in 1-3 mL of EG growth medium, and plated onto a feeder layer.

Ninety-six well tissue culture plates are prepared with a sub-confluent layer of feeder cells cultured for 3 days in modified EG growth medium free of LIF, bFGF or forskolin, inactivated with 5000 rad γ-irradiation. Suitable feeders are STO cells (ATCC Accession No. CRL 1503). ~0.2 mL of primary germ cell (PGC) suspension is added to each of the wells. The first passage is conducted after 7-10 days in EG growth medium, transferring each well to one well of a 24-well culture dish previously prepared with irradiated STO mouse fibroblasts. The cells are cultured with daily replacement of medium until cell morphology consistent with EG cells are observed, typically after 7-30 days or 1-4 passages.

Propagation of pPS Cells in an Undifferentiated State pPS cells can be propagated continuously in culture, using a combination of culture conditions that promote proliferation without promoting differentiation.

Traditionally, pPS cells are cultured on a layer of feeder cells, typically fibroblast type cells, often derived from embryonic or fetal tissue. The cell lines are plated to near confluence, usually irradiated to prevent proliferation, and then used to support pPS cell cultures.

In one illustration, pPS cells are first derived and supported on primary embryonic fibroblasts. Mouse embryonic fibroblasts (mEF) can be obtained from outbred CF1 mice (SASCO) or other suitable strains. The abdomen of a mouse at 13 days of pregnancy is swabbed with 70% ethanol, and the decidua is removed into phosphate buffered saline (PBS). Embryos are harvested; placenta, membranes, and soft tissues are removed; and the carcasses are washed twice in PBS. They are then transferred to fresh 10 cm bacterial dishes containing 2 mL trypsin/EDTA, and finely minced. After incubating 5 min at 37° C., the trypsin is inactivated with 5 mL DMEM containing 10% bovine serum (FBS), and the mixture is transferred to a 15 mL conical tube and dissociated. Debris is allowed to settle for 2 min, the supernatant is made up to a final volume of 10 mL, and plated onto a 10 cm tissue culture plate or T75 flask. The flask is incubated undisturbed for 24 h, after which the medium is replaced. When flasks are confluent (~2-3 d), they are split 1:2 into new flasks.

Scientists at Geron have discovered that hPS cells can be maintained in an undifferentiated state even without feeder cells. The environment for feeder-free cultures includes a suitable culture substrate, particularly an extracellular matrix, such as may be derived from basement membrane or that may form part of adhesion molecule receptor-ligand couplings. A suitable preparation is available from Becton Dickenson under the name Matrigel®. Other extracellular matrix components and component mixtures are suitable as an alterative. Depending on the cell type being proliferated, this may include laminin, fibronectin, proteoglycan, entactin, heparan sulfate, and the like, alone or in various combinations. Laminins are major components of all basal laminae in vertebrates, which interact with integrin heterodimers such as α6β1 and α6β4 (specific for laminins) and other heterodimers (that cross-react with other matrices).

The pluripotent stem cells are plated onto the substrate in a suitable distribution and in the presence of a medium that promotes cell survival, propagation, and retention of the desirable characteristics. It has been found that plating densities of at least ~15,000 cells cm$^{-2}$ (typically 90,000 cm$^{-2}$ to 170,000 cm$^{-2}$) promote survival and limit differentiation. The passage of pPS cells in the absence of feeders benefits from preparing the pPS cells in small clusters. Typically, enzymatic digestion is halted before cells become completely dispersed (say, ~5 min with collagenase IV). Clumps of ~10-2000 cells are then plated directly onto the substrate without further dispersal. Alternatively, primate PS cells can be passaged between feeder-free cultures as a finer cell suspension, providing that an appropriate enzyme and medium are chosen, and the plating density is sufficiently high. By way of illustration, confluent human embryonic stem cells cultured in the absence of feeders are removed from the plates by incubating with a solution of 0.05% (wt/vol) trypsin (Gibco) and 0.053 mM EDTA for 5-15 min at 37° C. With the use of pipette, the remaining cells in the plate are removed and the cells are triturated with the pipette until the cells are dispersed into a suspension comprising single cells and some small clusters. The cells are then plated at densities of 50,000-200,000 cells/cm$^2$ to promote survival and limit differentiation. The phenotype of ES cells passaged by this technique is similar to what is observed when cells are harvested as clusters by collagen digestion. As another option, the cells can be harvested without enzymes before the plate reaches confluence. The cells are incubated ~5 min in a solution of 0.5 mM EDTA alone in PBS, washed from the culture vessel, and then plated into a new culture without further dispersal.

pPS cells plated in the absence of fresh feeder cells benefit from being cultured in a nutrient medium. The medium will generally contain the usual components to enhance cell survival, including isotonic buffer, essential minerals, and either serum or a serum replacement of some kind. Conditioned medium can be prepared by culturing irradiated primary mouse embryonic fibroblasts (or another suitable cell preparation) at a density of ~5-6×10$^4$ cm$^{-2}$ in a serum free medium such as KO DMEM supplemented with 20% serum replacement and 4 ng/mL basic fibroblast growth factor (bFGF). The culture supernatant is harvested after ~1 day at 37° C.

As an alternative to primary mouse fibroblast cultures, conditioned medium can be prepared from an embryonic fibroblast cell line tested for its ability to condition medium appropriately. Such lines can optionally be transfected with telomerase reverse transcriptase to increase their replicative capacity. Another possible source is differentiated pPS cells with the morphological features of fibroblasts. pPS cells are suspension cultured as aggregates in differentiation medium using non-adherent cell culture plates (~2×10$^6$ cells/9.6 cm$^2$). After 2 days the aggregates are transferred into gelatin-coated plates, and fibroblast-like cells appear in clusters of 100-1000 cells in the mixed population after ~11 days. After brief collagenase treatment, the fibroblast-like cells can be collected under a microscope, passaged in mEF medium, and tested for their ability to condition ES medium.

Medium that has been conditioned for 1-2 days is typically used to support pPS cell culture for 1-2 days, and then exchanged. If desired, conditioned medium can be supplemented before use with additional growth factors that benefit pPS cell culture. For hES, a growth factor like bFGF or FGF-4 can be used. For hEG, culture medium may be supplemented with a growth factor like bFGF, an inducer of gp130, such as LIF or Oncostatin-M, and perhaps a factor that elevates cyclic AMP levels, such as forskolin.

Characteristics of Undifferentiated pPS Cells

In the two dimensions of a standard microscopic image, hES cells have high nuclear/cytoplasmic ratios in the plane of the image, prominent nucleoli, and compact colony formation with poorly discernable cell junctions. Cell lines can be karyotyped using a standard G-banding technique (available at many clinical diagnostics labs that provides routine karyotyping services, such as the Cytogenetics Lab at Oakland Calif.) and compared to published human karyotypes.

hES and hEG cells can also be characterized by expressed cell markers. In general, the tissue-specific markers discussed in this disclosure can be detected using a suitable immunological technique—such as flow cytometry for membrane-bound markers, immunohistochemistry for intracellular markers, and enzyme-linked immunoassay, for markers secreted into the medium. The expression of protein markers can also be detected at the mRNA level by reverse transcriptase-PCR using marker-specific primers. See U.S. Pat. No. 5,843,780 for further details.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., *Cell Lines from Human Germ Cell Tumors*, in E. J. Robertson, 1987, supra). hES cells are typically SSEA-1 negative and SSEA-4 positive. hEG cells are typically SSEA-1 positive. Differentiation of pPS cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze® XK Telomerase Detection Kit, Cat. s7707; Intergen Co., Purchase N.Y.; or TeloTAGGG™ Telomerase PCR ELISAplus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Differentiating pPS Cells

Differentiation of the pPS can be initiated by first forming embryoid bodies. General principles in culturing embryoid bodies are reported in O'Shea, Anat. Rec. (New Anat. 257: 323, 1999). pPS cells are cultured in a manner that permits aggregates to form, for which many options are available: for example, by overgrowth of a donor pPS cell culture, or by culturing pPS cells in culture vessels having a substrate with low adhesion properties which allows EB formation. Embryoid bodies can also be made in suspension culture. pPS cells are harvested by brief collagenase digestion, dissociated into clusters, and plated in non-adherent cell culture plates. The aggregates are fed every few days, and then harvested after a suitable period, typically 4-8 days. The cells can then be cultured in a medium and/or on a substrate that promotes enrichment of cells of a particular lineage. The substrate can comprise matrix components such as Matrigel® (Becton Dickenson), laminin, collagen, gelatin, or matrix produced by first culturing a matrix-producing cell line (such as a fibroblast or endothelial cell line), and then lysing and washing in such a way that the matrix remains attached to the surface of the vessel. Embryoid bodies comprise a heterogeneous cell population, potentially having an endoderm exterior, and a mesoderm and ectoderm interior.

Scientists at Geron Corporation have discovered that pPS cells can be differentiated into committed precursor cells or terminally differentiated cells without forming embryoid bodies or aggregates as an intermediate step. Briefly, a suspension of undifferentiated pPS cells is prepared, and then plated onto a solid surface that promotes differentiation. Suitable substrates include glass or plastic surfaces that are adherent. For example, glass coverslips can be coated with a polycationic substance, such as a polyamines like poly-lysine, poly-ornithine, or other homogeneous or mixed polypeptides or other polymers with a predominant positive charge. The cells are then cultured in a suitable nutrient medium that is adapted to promote differentiation towards the desired cell lineage.

In some circumstances, differentiation is further promoted by withdrawing serum or serum replacement from the culture medium. This can be achieved by substituting a medium devoid of serum and serum replacement, for example, at the time of replating. In certain embodiments of the invention, differentiation is promoted by withdrawing one or more medium component(s) that promote(s) growth of undifferentiated cells, or act(s) as an inhibitor of differentiation. Examples of such components include certain growth factors, mitogens, leukocyte inhibitory factor (LIF), and basic fibroblast growth factor (bFGF). Differentiation may also be promoted by adding a medium component that promotes differentiation towards the desired cell lineage, or inhibits the growth of cells with undesired characteristics. For example, to generate cells committed to neural or glial lineages, the medium can include any of the following factors or medium constituents in an effective combination: Brain derived neurotrophic factor (BDNF), neutrotrophin-3 (NT-3), NT-4, epidermal growth factor (EGF), ciliary neurotrophic factor (CNTF), nerve growth factor (NGF), retinoic acid (RA), sonic hedgehog, FGF-8, ascorbic acid, forskolin, fetal bovine serum (FBS), and bone morphogenic proteins (BMPs).

General principals for obtaining tissue cells from pluripotent stem cells are reviewed in Pedersen (Reprod. Fertil. Dev. 6:543, 1994), and U.S. Pat. No. 6,090,622. Other publications of interest include the following: For neural progenitors, neural restrictive cells and glial cell precursors, see Bain et al., Biochem. Biophys. Res. Commun. 200:1252, 1994; Trojanowski et al., Exp. Neurol. 144:92, 1997; Wojcik et al., Proc. Natl. Acad. Sci. USA 90:1305-130; and U.S. Pat. Nos. 5,851, 832, 5,928,947, 5,766,948, and 5,849,553. For cardiac muscle and cardiomyocytes see Chen et al., Dev. Dynamics 197:217, 1993 and Wobus et al., Differentiation 48:173, 1991. For hematopoietic progenitors, see Burkert et al., New Biol. 3:698, 1991 and Biesecker et al., Exp. Hematol. 21:774, 1993. U.S. Pat. No. 5,773,255 relates to glucose-responsive insulin secreting pancreatic beta cell lines. U.S. Pat. No. 5,789,246 relates to hepatocyte precursor cells. Other progenitors of interest include but are not limited to chondrocytes, osteoblasts, retinal pigment epithelial cells, fibroblasts, skin cells such as keratinocytes, dendritic cells, hair follicle cells, renal duct epithelial cells, smooth and skeletal muscle cells, testicular progenitors, and vascular endothelial cells.

Scientists at Geron Corporation have discovered that culturing pPS cells or embryoid body cells in the presence of ligands that bind growth factor receptors promotes enrichment for neural precursor cells. The growth environment may contain a neural cell supportive extracellular matrix, such as fibronectin. Suitable growth factors include but are not limited to EGF, bFGF, PDGF, IGF-1, and antibodies to receptors for these ligands. The cultured cells may then be optionally separated by whether they express a marker such as A2B5. Under the appropriate circumstances, populations of cells enriched for expression of the A2B5 marker may have the capacity to generate both neuronal cells (including mature neurons), and glial cells (including astrocytes and oligodendrocytes). Optionally, the cell populations are further differentiated, for example, by culturing in a medium containing an activator of cAMP.

Scientists at Geron Corporation have discovered that culturing pPS cells or embryoid body cells in the presence of a hepatocyte differentiation agent promotes enrichment for hepatocyte-like cells. The growth environment may contain a hepatocyte supportive extracellular matrix, such as collagen or Matrigel®. Suitable differentiation agents include various isomers of butyrate and their analogs, exemplified by n-butyrate. The cultured cells are optionally cultured simultaneously or sequentially with a hepatocyte maturation factor, such as an organic solvent like dimethyl sulfoxide (DMSO); a maturation cofactor such as retinoic acid; or a cytokine or hormone such as a glucocorticoid, epidermal growth factor (EGF), insulin, TGF-α, TGF-β, fibroblast growth factor (FGF), heparin, hepatocyte growth factor (HGF), IL-1, IL-6, IGF-I, IGF-II, and HBGF-1.

Scientists at Geron Corporation have discovered that it is also possible to differentiate hPS cells into a highly enriched population comprising cardiomyocytes or cardiomyocyte precursors. The cardiomyocyte lineage cells can be obtained, for example, by differentiating hES cells in a growth environment comprising a cardiotrophic factor that affects DNA-methylation, exemplified by 5-azacytidine. Spontaneously contracting cells can then be separated from other cells in the population, for example, by density centrifugation. Further process steps can include culturing the cells in a medium containing creatine, carnitine, or taurine. Alternatively, it is possible to differentiate hPS cells into a highly enriched population comprising osteoprogenitors or osteoblasts expressing osteocalcin and collagen-1. The cells can be obtained by taking pPS-derived mesenchymal cells and differentiating them in a medium containing a bone morphogenic protein (particularly BMP-4), a ligand for a human TGF-β receptor, or a ligand for a human vitamin D receptor.

Characteristics of Differentiated Cells

Cells can be characterized according to a number of phenotypic criteria. The criteria include but are not limited to characterization of morphological features, detection or quantitation of expressed cell markers and enzymatic activity, and determination of the functional properties of the cells in vivo.

Markers of interest for neural cells include β-tubulin III or neurofilament, characteristic of neurons; glial fibrillary acidic protein (GFAP), present in astrocytes; galactocerebroside (GalC) or myelin basic protein (MBP); characteristic of oligodendrocytes; OCT-4, characteristic of undifferentiated hES cells; nestin, characteristic of neural precursors and other cells. A2B5 and NCAM are characteristic of glial progenitors and neural progenitors, respectively. Cells can also be tested for secretion of characteristic biologically active substances. For example, GABA-secreting neurons can be identified by production of glutamic acid decarboxylase or GABA. Dopaminergic neurons can be identified by production of dopa decarboxylase, dopamine, or tyrosine hydroxylase.

Markers of interest for liver cells include α-fetoprotein (liver progenitors); albumin, $\alpha_1$-antitrypsin, glucose-6-phosphatase, cytochrome p450 activity, transferrin, asialoglycoprotein receptor, and glycogen storage (hepatocytes); CK7, CK19, and γ-glutamyl transferase (bile epithelium). It has been reported that hepatocyte differentiation requires the transcription factor HNF-4α (Li et al., Genes Dev. 14:464, 2000). Markers independent of HNF-4α expression include $\alpha_1$-antitrypsin, α-fetoprotein, apoE, glucokinase, insulin growth factors 1 and 2, IGF-1 receptor, insulin receptor, and leptin. Markers dependent on HNF-4α expression include albumin, apoAI, apoAII, apoB, apoCIII, apoCII, aldolase B, phenylalanine hydroxylase, L-type fatty acid binding protein, transferrin, retinol binding protein, and erythropoietin (EPO).

Cell types in mixed cell populations derived from pPS cells can be recognized by characteristic morphology and the markers they express. For skeletal muscle: myoD, myogenin, and myf-5. For endothelial cells: PECAM (platelet endothelial cell adhesion molecule), Flk-1, tie-1, tie-2, vascular endothelial (VE) cadherin, MECA-32, and MEC-14.7. For smooth muscle cells: specific myosin heavy chain. For cardiomyocytes: GATA-4, Nkx2.5, cardiac troponin I, α-myosin heavy chain, and ANF. For pancreatic cells, pdx and insulin secretion. For hematopoietic cells and their progenitors: GATA-1, CD34, AC133, β-major globulin, and β-major globulin like gene βH1.

Certain tissue-specific markers listed in this disclosure or known in the art can be detected by immunological techniques—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez).

Preparing Cell Populations Essentially Free of Undifferentiated Cells

In accordance with this invention, populations of differentiated cells are depleted of relatively undifferentiated cells by expressing a gene that is lethal to cells or renders them susceptible to a lethal effect of an external agent, under control of a transcriptional control element that causes the gene to be preferentially expressed in the undifferentiated cells.

To accomplish this, the cells are genetically altered either before or after the process used to differentiate the cells into the desired lineage for therapy, in a way that puts an effector gene suitable for negative selection of undifferentiated cells, under control of a transcriptional control element with the desired properties.

Transcriptional Control Elements for Driving Negative Selection

The control element is selected with a view to the protein expression patterns of the undifferentiated and differentiated cells in the population.

Genes with desirable expression patterns can be identified by comparing expression at the transcription, translation, or functional level in two different cell populations—one relatively enriched for differentiated cells, the other relatively enriched for undifferentiated cells. Suitable methods of comparison include subtractive hybridization of cDNA libraries, and microarray analysis of mRNA levels. Once a transcript is identified with an appropriate expression pattern, the promoter or enhancer of the corresponding gene can be used for construction of the negative selection vector.

A suitable microarray analysis is conducted using a Genetic Microsystems array generator, and an Axon GenePix™ Scanner. Microarrays are prepared by amplifying cDNA fragments in a 96 or 384 well format, and then spotted directly onto glass slides. To compare mRNA preparations from two cell populations, one preparation is converted into Cy3-labeled cDNA, while the other is converted into Cy5-labeled cDNA. The two cDNA preparations are hybridized simultaneously to the microarray slide, and then washed to eliminate non-specific binding. Any given spot on the array will bind each of the cDNA products in proportion to abundance of the transcript in the two original mRNA preparations. The slide is then scanned at wavelengths appropriate for each of the labels, and the relative abundance of mRNA is determined. Preferably, the level of expression of the effector gene will be at least 5-fold or even 25-fold higher in the undifferentiated cells relative to the differentiated cells.

For the depletion of pluripotent embryonic cells, an exemplary control element is the promoter for telomerase reverse transcriptase (TERT). Sequence of the human TERT gene (including upstream promoter sequence) is provided below. The reader is also referred to U.K. Patent GB 2321642 B (Cech et al., Geron Corporation and U. Colorado), International Patent Publications WO 00/46355 (Morin et al., Geron Corporation), WO 99/33998 (Hagen et al., Bayer Aktiengesellschaft), and Horikawa, I., et al. (Cancer Res., 59:826, 1999). Sequence of the mouse TERT gene is provided in WO 99/27113 (Morin et al., Geron Corporation). A lambda phage clone designated λGΦ5, containing ~13,500 bases upstream from the hTERT encoding sequence is available from the ATCC under Accession No. 98505. Example 9 illustrates the testing and use of TERT promoter sequences (SEQ. ID NO:1) in vector expression systems.

Another exemplary control element is a promoter sequence for Octamer binding transcription factor 4 (OCT-4), a member of the POU family of transcription factors. OCT-4 transcription is activated between the 4 and 80 cell stage in the developing embryo, and it is highly expressed in the expanding blastocyst and then in the pluripotent cells of the egg cylinder. Transcription is down-regulated as the primitive ectoderm differentiates to form mesoderm, and by 8.5 days post coitum is restricted to migrating primordial germ cells. High-level OCT-4 gene expression is also observed in pluripotent embryo carcinoma and embryonic stem cell lines, and is down-regulated when these cells are induced to differentiate. Pig, mouse, and human OCT-4 promoter sequences are provided in International Patent Publication WO 9919469 (Biotransplant Inc.).

Other suitable control elements can be obtained from genes causing expression of markers characteristic of undifferentiated cells in the population but not of the differentiated cells. For example, SSEA-3, SSEA-4, Tra-1-60 and Tra-1-81 are characteristic of various types of undifferentiated pluripotent embryonic stem cells. The enzyme responsible for synthesis of SSEA-4 may have transcriptional control elements with the desirable expression specificity. A more recent example is the promoter for Rex1 protein, a retanoic acid regulated zinc finger protein that is expressed in preimplantation embryos. The mouse Rex1 promoter has been shown to act as an effective transcription marker for undifferentiated embryonic stem cells (Eiges et al., Current Biol. 11:514, 2001.

Suitability of particular elements can be estimated by analysis of gene transcript expression, for example, by microarray analysis. Reporter constructs can then be tested in differentiated and undifferentiated cells for the appropriate specificity, using a promoter or enhancer sequence from the identified cell-specific gene to control transcription of a reporter gene, such as green fluorescence protein, secreted alkaline phosphatase, β-glucuronidase, or β-galactosidase. Use of reporter constructs to test promoter specificity is illustrated below in Example 9.

Effector Genes for Achieving Negative Selection

A transcriptional regulatory element with appropriate specificity is operatively linked to an encoding region for a product that will provide elimination of cells in which it is expressed—either directly, or by rendering the cell susceptible to an otherwise innocuous external agent.

Suitable effector genes include those that encode a peptide toxin—such as ricin, abrin, diphtheria, gelonin, *Pseudomonas* exotoxin A, *Crotalus durissus terrificus* toxin, *Crotalus adamenteus* toxin, *Naja naja* toxin, and *Naja mocambique* toxin. Hughes et al., Hum. Exp. Toxicol. 15:443, 1996; Rosenblum et al., Cancer Immunol. Immunother. 42:115, 1996; Rodriguez et al., Prostate 34:259, 1998; Mauceri et al., Cancer Res. 56:4311; 1996.

Also suitable are genes that induce or mediate apoptosis—such as the ICE-family of cysteine proteases, the Bcl-2 family of proteins, Bax, bclXs and caspases (Favrot et al., Gene Ther. 5:728, 1998; McGill et al., Front. Biosci. 2:D353, 1997; McDonnell et al., Semin. Cancer Biol. 6:53, 1995). Another potential anti-tumor agent is apoptin, a protein that induces apoptosis even where small drug chemotherapeutics fail (Pietersen et al., *Adv. Exp. Med. Biol.* 465:153, 2000). Koga et al. (Hu. Gene Ther. 11:1397, 2000) propose a telomerase-specific gene therapy using the hTERT gene promoter linked to the apoptosis gene Caspase-8 (FLICE). Gu et al. (Cancer Res. 60:5359, 2000) reported a binary adenoviral system that induced Bax expression via the hTERT promoter. They found that it elicited tumor-specific apoptosis in vitro and suppressed tumor growth in nude mice.

Also of interest are enzymes present in the lytic package that cytotoxic T lymphocytes or LAK cells deliver to their targets. Perforin, a pore-forming protein, and Fas ligand are major cytolytic molecules in these cells (Brandau et al., Clin. Cancer Res. 6:3729, 2000; Cruz et al., Br. J. Cancer 81:881, 1999). CTLs also express a family of at least 11 serine proteases termed granzymes, which have four primary substrate specificities (Kam et al., Biochim. Biophys. Acta 1477:307, 2000). Low concentrations of streptolysin O and pneumolysin facilitate granzyme B-dependent apoptosis (Browne et al., Mol. Cell Biol. 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Lethality to progeny with an undifferentiated phenotype only occurs when the prodrug is present. Thus, the prodrug can be combined with the cells while they are being differentiated, expanded, or maintained in vitro, to minimize the proportion of cells with undifferentiated phenotype. The reader will readily appreciate that the prodrug can also be given to a patient being treated with the cells, either simultaneously with the treatment, or at a subsequent time, in order to minimize the emergence of progeny with an undifferentiated phenotype in vivo.

Exemplary effector genes with this property encode thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

U.S. Pat. No. 5,631,236 (Baylor College of Medicine) outlines adenoviral vectors containing an HSV tk gene operatively linked to a promoter that expresses tk in cancer cells. U.S. Pat. No. 5,997,859 and EP 702084 B1 (Chiron) pertain to replication-defective recombinant retrovirus, carrying a vector construct directing expression of HSV tk gene for converting an otherwise inert compound into a cytotoxic form. EP 415731 A1, EP 657540 A1, and EP 657541 A1 (Wellcome Foundation) propose retroviral vectors encoding an enzyme such as VZV tk, carboxypeptidase G2, alkaline phosphatase, penicillin-V amidase, and cytosine deaminase, for converting a prodrug into an agent toxic to a cancer cell. International Patent Publications WO 98/14593 and WO 00/46355 (Geron Corporation) describe constructs comprising HSV tk under control of hTERT promoter sequences.

The human HSV tk gene sequence is provided below (SEQ. ID NOS:2 & 3), along with illustrations of its use to target cells expressing TERT. Simultaneously or following expression of the gene in target cells, a convertible prodrug such as ganciclovir is added to the environment to effect depletion of the targets.

Another type of effector that renders the cell susceptible to an otherwise non-toxic agent is a gene that causes presentation of a foreign antigen on the cell membrane. The presented substance may be an alloantigen, a xenoantigen, or an antigen from a non-mammalian species for which specific antibody is readily available. Expression of the gene leads to presentation of the antigen on undifferentiated cells, which then can be used to effect depletion by a suitable immunological separation—such as immunoaffinity (e.g., panning), fluorescence-activated cell sorting, or complement-mediated lysis.

When the transducing agent is a viral vector, the effector can be a viral gene required for replication of the virus. Essential genes for replication of adenovirus include the E4, E1a, E1b, and E2 regions. Essential genes for replication of HSV-1 include ICP6 and ICP4. These genes are placed under control of the specific promoter, and used to transduce cells in the differentiated cell population. The viruses then replicate specifically in any undifferentiated cells present, causing them to rupture. See International Patent Publication WO 00/46355 (Morin et al., Geron Corporation) for a description of lytic vectors that replicate in cells expressing TERT.

Another type of effector sequence encodes a membrane protein that contains the epitope recognized by the specific antibody. The membrane protein may be a protein expressed in the same species on other types of cells, but more typically is obtained from another species, or is an artificial sequence. In this case, the antigen will be foreign to the species from which the stem cells are derived, and antibodies made in the same species will not cross-react with other antigens on the cell.

Alternatively, the target antigen can be a cell-surface carbohydrate or lipid component. In this case, the effector sequence will encode an enzyme involved in antigen synthesis. Of particular interest are glycosyl transferases of mammalian or non-mammalian origin that synthesize carbohydrate differentiation antigen, alloantigen, xenoantigen, or novel determinants detectable by antibody. Examples include the marker SSEA-1, for which the effector sequence encodes the corresponding fucosyltransferase; the Gal$\alpha$(1,3)Gal linkage present on endothelial tissue of most mammals except for humans and old-world monkeys, formed by an $\alpha$(1,3)galactosyltransferase ($\alpha$1,3GT); and the ABO histo blood group antigens present on most human cells, for which the encoding sequence is the corresponding ABO transferase. See GenBank Accession Nos. S71333, J05175, and AF134414. The Gal$\alpha$(1,3)Gal and ABO determinants are all susceptible to lysis mediated by antibodies that naturally occur in subjects that do not have the determinants as a self-antigen.

Another possible effector sequence is based on RNA-interference (RNAi) technology. Double-stranded or hairpin RNA corresponding to a portion of mature mRNA in a cell (such as a gene transcript) cause the target mRNA to be destroyed (Sharp et al., Genes Dev. 13:139, 1999; Wianny et al., Nat. Cell Biol. 2:70, 2000). For example, a plasmid containing a promoter that drives expression of a hairpin RNA (a transcript consisting of inverted repeats taken from the coding region of a cellular gene, separated by a short linker sequence, thus generating a synthetic RNA containing a double-stranded region) has been used to induce stable and inheritable RNAi effects in *C. elegans* (Tavernarakis et al.; Nat. Genet. 24:180, 2000).

In certain embodiments of this invention, a control element driving transcription in an undifferentiated cell (or a cell expressing TERT) is operatively linked to an encoding sequence for hairpin RNAI that targets a particular gene transcript. The target gene is chosen to be essential for cell viability: for example, a basic transcription or translation factor, a tRNA gene, a ribosomal RNA subunit, or DNA or RNA polymerase. In one illustration, the hTERT promoter drives RNAi that inactivates a gene in the purine salvage pathway. In the presence of drugs such as aminopterin, de novo synthesis of purines is prevented, because the activity of the enzymes hypoxanthine-guanine phosphoribosyl transferase (HGPRT) and thymidine kinase (TK) is inhibited. Cells that possess HGPRT and TK survive in the presence of aminopterin, as long as the medium is supplemented with hypoxanthine and thymidine (HAT medium). Residual undifferentiated cells can be removed from the population by incubation with HAT medium. Transcripts of essential genes such as HGPRT and TK can also be targeted using other types of effector sequences—for example, antisense polynucleotides, ribozymes, or encoding sequences for dominant negative analogs that lack a functional catalytic domain.

The effector region used in the vectors of this invention can be constructed so as to be functionally controlled by a molecular switch. Fusions between the ligand-binding domain of receptors result in molecules in which the normal function of the native protein is inhibited in the absence of the hormone recognized by the ligand-binding domain. A fusion protein is constructed comprising a switch molecule binding domain coupled to an effector domain, in such a way that binding of a ligand (such as a small molecule hapten) to the binding domain unmasks or activates the effector domain. Suitable ligand binding domains can be taken from a receptor (such the estrogen receptor) or an antibody. The effector domain can be any of the proteins already listed that are lethal to the cell, such as peptide toxins, endonucleases (meganucleases such as I-Sce −1 or humanized versions of standard restriction endonucleases), or mediators of apoptosis. The lethal function of the effector gene is quiescent, unless the ligand is present. This provides another system where the effector gene renders the cell susceptible to toxic effects of an external agent (in this case the ligand), which can be administered at will to control the depletion of undifferentiated cells, either in culture or in vivo.

The vector constructs for use in this invention can also contain a positive selection marker, such as an antibiotic resistance gene, that is also under control of the specific promoter. Exemplary is a vector having the configuration hTERT promoter—tk gene—IRES-neo. This is designed so that both the suicide effector and drug resistance gene are expressed under control of the TERT promoter. The internal ribosome entry site (IRES) sequence allows both the tk gene and the neo gene to be under transcriptional control of the hTERT promoter. A post-translational cleavage site, such as 2A sequences (Felipe et al., Gene Ther. 6:198, 1999 (can be used to similar effect. Generation and selection of hES lines that have stably integrated such a construct is facilitated by the activity of the drug resistance gene in the undifferentiated cells. This has an advantage over co-transfection methods using a drug resistant gene under control of a different promoter, because the drug resistance gene will not be expressed in differentiated cells. This should avoid an unwanted immunological response by the host against the gene product in transplanted cells.

Selection Techniques to Eliminate Undifferentiated Cells

To deplete differentiated cell populations of undifferentiated cells, the effector gene is selectively expressed in the undifferentiated cells.

This can be accomplished in several ways. In one embodiment, the population is genetically altered using a vector in which a transcriptional control element of the appropriate specificity is operatively linked to the effector gene. The genetic alteration may be transient (for example, using an adenovirus vector), meaning that the level of expression diminishes as the cells divide. This is suitable for generating differentiated cell populations that will be free of heterologous genes at the time of therapy. The genetic alteration may also be permanent (for example, using a retroviral vector), meaning that the alteration is inheritable by progeny of the initially altered cell. This is suitable for generating differentiated cell populations that will have an ongoing corrective function as they proliferate in vitro or in vivo, to eliminate any undifferentiated or dedifferentiated cells that arise in the population.

Any suitable expression vector can be used. Suitable viral vector systems for producing stem cells altered according to this invention can be prepared using commercially available virus components. Viral vectors comprising effector genes are generally described in the publications referenced in the last section. Alternatively, vector plasmids can be introduced into cells by electroporation, or using lipid/DNA complexes, such as those described in U.S. Pat. Nos. 5,578,475; 5,627,175; 5,705,308; 5,744,335; 5,976,567; 6,020,202; and 6,051,429. Exemplary is the formulation Lipofectamine 2000™, available from Gibco/Life Technologies. Another exemplary reagent is FuGENE™ 6 Transfection Reagent, a blend of lipids in non-liposomal form and other compounds in 80% ethanol, obtainable from Roche Diagnostics Corporation.

In another embodiment, the effector gene is placed under control of an endogenous transcriptional control element, such as the hTERT or OCT-4 promoter. This can be effected, for example, by homologous recombination, using a vector comprising the effector encoding sequence, flanked on one side by the transcriptional control element and other upstream genomic sequence, and flanked on the other side by downstream genomic sequence for the targeted gene. U.S. Pat. Nos. 5,464,764 and 5,631,153 describe a double-selection strategy, in which two sequences homologous to the gene target flank a positive selection marker, and a negative selection marker is attached to the 3' terminal of the second flanking region. U.S. Pat. No. 5,789,215 reports the use of homologous recombination targeting vectors for modifying the cell genome of mouse embryonic stem cells. Other information of interest for homologous recombination targeting can be found in U.S. Pat. Nos. 5,589,369, 5,776,774, and 5,789,215.

If the effector gene directly causes cell lysis or apoptosis, then the population will be depleted of undifferentiated cells upon culturing the cells under conditions where the control element is expected to cause transcription of the gene. However, if the effector gene is not directly lethal, but renders the cell susceptible to the lethal effects of an external agent, then depletion will be postponed until the external agent is provided. For example, where the gene is a prodrug converting enzyme, then depletion is effected upon placing the cells in an environment containing the prodrug. Where the gene is an antibody target, then depletion is effected upon placing the cells in an environment containing specific antibody, plus complement. The environment can be a culture vessel, in which case the agent can just be added to the culture medium at the requisite concentration. Alternatively or in addition, depletion can be performed in vivo, by administering the cell population to a subject, and simultaneously or sequentially administering the agent, if not already present.

Cell populations in which the majority of cells are differentiated can be genetically modified according to these procedures to deplete undifferentiated cells. Alternatively, a precursor population of relatively undifferentiated cells can be genetically modified according to these procedures, and then differentiated. In this situation, it is more typical to use an effector gene that does not kill the cells immediately upon expression, but renders the cells susceptible to the lethal effect of some external agent. In one illustration, undifferentiated pPS cells grown in culture are transduced with a retrovirus vector in which the herpes thymidine kinase gene is under control of the hTERT promoter. The cells are optionally selected for positive transduction, either by incorporating a selectable marker in the construct, or by measuring expression of the transduced gene, and proliferated in culture. When differentiated cells are desired, the population is taken through a differentiation procedure (for example, to make hepatocyte or neuron precursors, as described earlier). They are then cultured under conditions that permit expression of the tk gene in the presence of ganciclovir.

As an illustration where RNAi is the effector sequence, hES cells are stably transfected (e.g., by lipofection) with a construct consisting of 2 cassettes: one in which the PGK promoter drives the neomycin phosphotransferase gene (resulting in resistance to toxic neomycin analogs such as geneticin); the other in which the hTERT promoter drives an encoding region for RNAi that contains double-stranded regions from HGPRT or TK. Stably modified clones are isolated in a medium containing both geneticin and azaguanine or 6-mercaptopurine (to select for HGPRT negative cells), or in medium containing both geneticin and 5-bromodeoxyuridine (to select for TK negative cells). Alternatively, the transfection could be done with just the RNAi kit, in which case geneticin is omitted from the medium. After isolation of the surviving clones, these lines are induced to differentiate to the desired cell type, and exposed to HAT medium to kill any residual stem cells.

Cell populations may be obtained using these techniques that are "depleted" of undifferentiated cells, which indicates any significant reduction in the proportion of undifferentiated cells present. After the procedure is effected, the proportion of undifferentiated cells may be decreased by 50% or even 90%. Depending on the control element and effector chosen, it may be possible to achieve differentiated cell populations that are "essentially free" of undifferentiated cells. This means that the population as a whole contains less than 1% of cells with the undifferentiated phenotype. Populations containing less than 0.2%, 0.05%, 0.01%, 20 ppm or 5 ppm undifferentiated cells are increasingly more preferred. For pPS cells, the presence of undifferentiated cells can be determined by counting cells expressing SSEA-4 by FACS analysis, or by counting cells expressing TERT or OCT-4 by fluorescence in-situ hybridization.

Use of Differentiated Cells

Cells prepared according to this invention can be used for a variety of commercially important research, diagnostic, and therapeutic purposes.

Because the cell populations of this invention are depleted of undifferentiated cells, they can be used to prepare antibodies and cDNA libraries that are specific for the differentiated phenotype. General techniques used in raising, purifying and modifying antibodies, and their use in immunoassays and immunoisolation methods are described in *Handbook of Experimental Immunology* (Weir & Blackwell, eds.); *Current Protocols in Immunology* (Coligan et al., eds.); and *Methods of Immunological Analysis* (Masseyeff et al., eds., Weinheim: VCH Verlags GmbH). General techniques involved in preparation of mRNA and cDNA libraries are described in *RNA Methodologies: A Laboratory Guide for Isolation and Characterization* (R. E. Farrell, Academic Press, 1998); *cDNA Library Protocols* (Cowell & Austin, eds., Humana Press); and *Functional Genomics* (Hunt & Livesey, eds., 2000).

Relatively homogeneous cell populations are particularly suited for use in drug screening and therapeutic applications.

Drug Screening

Differentiated pPS cells of this invention can be used to screen for factors (such as solvents, small molecule drugs, peptides, polynucleotides, and the like) or environmental conditions (such as culture conditions or manipulation) that affect the characteristics of differentiated cells.

In some applications, differentiated cells are used to screen factors that promote maturation, or promote proliferation and maintenance of such cells in long-term culture. For example, candidate maturation factors or growth factors are tested by adding them to pPS cells in different wells, and then determining any phenotypic change that results, according to desirable criteria for further culture and use of the cells.

Particular screening applications of this invention relate to the testing of pharmaceutical compounds in drug research. The reader is referred generally to the standard textbook "In vitro Methods in Pharmaceutical Research", Academic Press, 1997, and U.S. Pat. No. 5,030,015). Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be determined by measuring DNA synthesis or repair. [$^3$H]thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Therapeutic Use

Differentiated cells of this invention can also be used for tissue reconstitution or regeneration in a human patient in need thereof. The cells are administered in a manner that permits them to graft to the intended tissue site and reconstitute or regenerate the functionally deficient area.

In one example, neural stem cells are transplanted directly into parenchymal or intrathecal sites of the central nervous system, according to the disease being treated. Grafts are done using single cell suspension or small aggregates at a density of 25,000-500,000 cells per μL (U.S. Pat. No. 5,968, 829). The efficacy of neural cell transplants can be assessed in a rat model for acutely injured spinal cord as described by McDonald et al. (Nat. Med. 5:1410, 1999. A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells embodied in this invention are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared according to this invention can be assessed in animal models for ability to repair liver damage. One such example is damage caused by intrapentoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

The efficacy of cardiomyocytes prepared according to this invention can be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modeled using an embolization coil in the distal portion of the left anterior descending artery (Watanabe et al., Cell Transplant. 7:239, 1998), and efficacy of treatment can be evaluated by histology and cardiac function. Cardiomyocyte preparations embodied in this invention can be used in therapy to regenerate cardiac muscle and treat insufficient cardiac function (U.S. Pat. No. 5,919,449 and WO 99/03973).

The examples that follow are provided by way of further illustration, and are not meant to imply any limitation in practicing the claimed invention.

EXAMPLES

Example 1

Feeder-Free Passage of hES Cells

In this experiment, undifferentiated hES cells that had been maintained on primary mouse embryonic feeder cells were harvested, and then maintained in the absence of feeders. The culture wells were coated with Matrigel®, and the cells were cultured in the presence of conditioned nutrient medium obtained from a culture of irradiated primary fibroblasts.

Preparation of Conditioned Media (CM) from Primary Mouse Embryonic Fibroblasts (mEF):

Fibroblasts were harvested from T150 flasks by washing one time with $Ca^{++}/Mg^{++}$ free PBS and incubating in 1.5-2 mL trypsin/EDTA (Gibco) for about 5 min. After the fibroblasts detached from the flask, they were collected in mEF media (DMEM+10% FBS). The cells were irradiated at 4000 rad (508 sec at 140 kV: shelf setting 6 in a Torrex™ generator), counted and seeded at about 55,000 cells $cm^{-2}$ in mEF media (525,000 cells/well of a 6 well plate). After at least 4 hours the media were exchanged with SR containing ES media (containing bFGF), using 3-4 mL per 9.6 cm well of a 6 well plate. Conditioned media was collected daily for feeding of hES cultures. Alternatively, medium was prepared using mEF plated in culture flasks, exchanging medium daily at 0.3-0.4 mL $cm^{-2}$. Before addition to the hES cultures, the conditioned medium was supplemented with 4 ng/mL of human bFGF (Gibco). Fibroblasts cultures were used in this system for about 1 week, before replacing with newly prepared cells.

Matrigel® Coating:

Growth Factor Reduced Matrigel® or regular Matrigel® (Becton-Dickinson, Bedford Mass.) was thawed at 4° C. The Matrigel® was diluted 1:10 to 1:500 (typically 1:30) in cold KO DMEM. 0.75-1.0 mL of solution was added to each 9.6 $cm^2$ well, and incubated at room temp for 1 h. The coated wells were washed once with cold KO DMEM before adding cells. Plates were used within 2 h after coating, or stored in DMEM at 4° C. and used within ~1 week.

Human ES Culture:

Undifferentiated hES colonies were harvested from hES cultures on feeders as follows. Cultures were incubated in ~200 U/mL collagenase IV for about 5 minutes at 37° C. Colonies were harvested by picking individual colonies up with a 20 μL pipet tip under a microscope or by scraping and dissociating into small clusters in conditioned medium (CM). These cells were then seeded onto Matrigel® in conditioned media at 15 colonies to each 9.6 $cm^2$ well (if 1 colony is ~10,000 cells, then the plating density is ~15,000 cells $cm^{-2}$).

The day after seeding on Matrigel®, hES cells were visible as small colonies (~100-2,000 cells) and there were single cells in-between the colonies that appeared to be differentiating or dying. As the hES cells proliferated, the colonies became quite large and very compact, representing the majority of surface area of the culture dish. The hES cells in the colonies had a high nucleus to cytoplasm ratio and had prominent nucleoli, similar to hES cells maintained on feeder cells. At confluence, the differentiated cells in between the colonies represented less than 10% of the cells in the culture.

Six days after seeding, the cultures had become almost confluent. The cultures were split by incubating with 1 mL ~200 U/mL Collagenase IV solution in KO DMEM for ~5 minutes at 37° C. The collagenase solution was aspirated, 2 mL hES medium was added per well, and the hES cells were scraped from the dish with a pipette. The cell suspension was transferred to a 15 mL conical tube, brought up to a volume of 6 mL, and gently triturated to dissociate the cells into small clusters of 10-2000 cells. The cells were then re-seeded on Matrigel® coated plates in CM, as above. Cells were seeded at a 1:3 or 1:6 ratio, approximately 90,000 to 170,000 cells $cm^{-2}$, making up the volume in each well to 3 mL. Medium was changed daily, and the cells were split and passaged again at 13 d and again at 19 d after initial seeding.

On day 19 after initial seeding, cells were harvested and evaluated for surface marker expression by immunofluorescence cell cytometry, using labeled antibodies specific for cell surface markers. For the hES cells maintained in the absence of feeders, a high percentage express SSEA-4, Tra-1-60 or Tra-1-81. These 3 markers are expressed on undifferentiated human ES cells that are maintained on feeders (Thomson et al., 1998). In addition, there is very little expression of SSEA-1, a glycolipid that is not expressed (or expressed at low levels) on undifferentiated ES cells. Immunohistochemical evaluation of SSEA-4, Tra-1-60 and Tra-1-81 indicates that the expression of these markers is localized to the ES colonies, not the differentiated cells in between the colonies.

Cultures of hES cells have been grown in the absence of feeder cells for over 180 days after initial seeding, with no apparent change in the proliferative capacity or phenotype. Human ES cells maintained on Matrigel® in mEF conditioned medium have a doubling time of about 31-33 hours, similar to the proliferation rate for hES cells grown on mEF feeder cells. H1 cells after 64 days of feeder-free culture showed a normal karyotype.

Example 2

Phenotypic Markers of hES Cells in Feeder-Free Culture

Undifferentiated hES cells express SSEA-4, Tra-1-60, Tra-1-81, OCT-4, and hTERT. The expression of these markers decreases upon differentiation. In order to assess whether the cells maintained in feeder-free conditions retained these markers, cells were evaluated by immunostaining, reverse transcriptase PCR amplification, and assay for telomerase activity.

For analysis by fluorescence-activated cell sorting (FACS), the hES cells were dissociated in 0.5 mM EDTA in PBS and resuspended to about $5 \times 10^5$ cells in 50 µL diluent containing 0.1% BSA in PBS. For analyzing surface marker expression, cells were incubated in the primary antibodies, including IgG isotype control (0.5 µg/test), IgM isotype control (1:10), SSEA-1 (1:10), SSEA-4 (1:20), Tra-1-60 (1:40) and Tra-1-81 (1:80), diluted in the diluent at 4° C. for 30 min. After washing with the diluent, cells were incubated with rat anti-mouse kappa chain antibodies conjugated with PE (Becton Dickinson, San Jose, Calif.) at 4° C. for 30 min. Cells were washed and analyzed on FACScalibur™ Flow Cytometer (Becton Dickinson, San Jose, Calif.) using CellQuest™ software.

Similar to the hES cells on feeders, cells on Matrigel®, laminin, fibronectin or collagen IV expressed SSEA-4, Tra-1-60 and Tra-1-81. There was very little expression of SSEA-1, a glycolipid that is not expressed by undifferentiated hES cells.

For analysis by immunocytochemistry, cells were incubated with primary antibodies, including SSEA-1 (1:10), SSEA-4 (1:20), Tra-1-60 (1:40) and Tra-1-81 (1:80), diluted in knockout DMEM at 37° C. for 30 min. Cells were then washed with warm knockout DMEM and fixed in 2% paraformaldehyde for 15 min. After washing with PBS, cells were incubated with 5% goat serum in PBS at room temp for 30 min, followed by incubation with the FITC-conjugated goat anti-mouse antibodies (1:125) (Sigma) at room temp for 30 min. Cells were washed, stained with DAPI and mounted. The staining was typically performed ~2 days after passaging. Cells were also examined for expression of alkaline phosphatase, a marker for undifferentiated ES cells. This was performed by culturing the cells on chamber slides, fixing with 4% paraformaldehyde for 15 min, and then washing with PBS. Cells were then incubated with alkaline phosphatase substrate (Vector Laboratories, Inc., Burlingame, Calif.) at room temperature in the dark for 1 h. Slides were rinsed for 2-5 min in 100% ethanol before mounting.

The results showed that SSEA-4, Tra-1-60, Tra-1-81, and alkaline phosphatase were expressed by the hES colonies on Matrigel® or laminin, as seen for the cells on feeders—but not by the differentiated cells in between the colonies.

Figure 1:
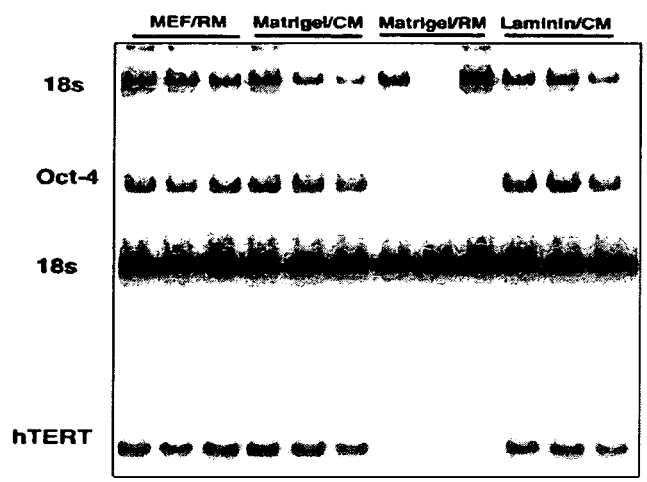
FIG. 1 provides an analysis of OCT-4 and hTERT expression in hES cells cultured with feeder cells (mEF) or extracellular matrix (Matrigel® or laminin) with regular medium (RM) or conditioned medium (CM). The upper panel is a copy of a gel showing OCT-4 and hTERT expression at the mRNA level by RT-PCR. The lower panel is a bar graph comparing the level of expression for cells grown on different substrates, expressed as the ratio of OCT-4 or hTERT to the 18s standard. hES cells grown on Laminin and Matrigel® in conditioned medium have similar expression patterns to those of cells grown on a feeder layer.
Figure 1:
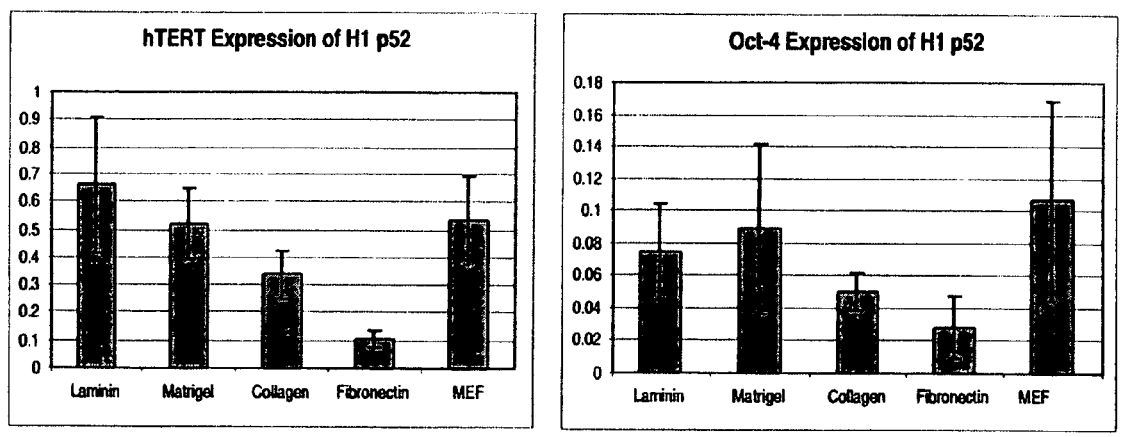

FIG. 1 shows OCT-4 and hTERT expression of H1 cells on feeders and off feeders, as detected by reverse-transcriptase PCR amplification. For radioactive relative quantification of individual gene products, QuantumRNA™ Alternate18S Internal Standard primers (Ambion, Austin Tex., USA) were employed according to the manufacturer's instructions. Briefly, the linear range of amplification of a particular primer pair was determined, then coamplified with the appropriate mixture of alternate18S primers:competimers to yield PCR products with coinciding linear ranges. Before addition of AmpliTaq™ (Roche) to PCR reactions, the enzyme was pre-incubated with the TaqStart™ antibody (ProMega) according to manufacturer's instructions. Radioactive PCR reactions were analyzed on 5% non-denaturing polyacrylamide gels, dried, and exposed to phosphoimage screens (Molecular Dynamics) for 1 hour. Screens were scanned with a Molecular Dynamics Storm 860 and band intensities were quantified using ImageQuant™ software. Results are expressed as the ratio of radioactivity incorporated into the hTERT or OCT-4 band, standardized to the radioactivity incorporated into the 18s band.

Primers and amplification conditions for particular markers are as follows. OCT-4: Sense (SEQ. ID NO:4) 5'-CTTGCTGCAG MGTGGGTGG AGGM-3'AntiSense (SEQ. ID NO:5) 5'-CTGCAGTGTG GGTTTCGGGC A-3'; alternate18:competimers 1:4; 19 cycles (94° 30 sec; 60° 30 sec; 72° 30 sec). hTERT: Sense (SEQ. ID NO:6) 5'-CGGMGAGTG TCTGGAGCM-3'AntiSense (SEQ. ID NO:7) 5'-GGATGMGCG GAGTCTGGA-3'; alternate18:competimers 1:12; 34 cycles (94° 30 sec; 60° 30 sec; 72° 30 sec).

hTERT and OCT-4 expression was seen in all the culture conditions except Matrigel® and regular medium. Furthermore, after exposure of cells to retinoic acid (RA) or dimethyl sulfoxide (DMSO), factors that promote cell differentiation, the expression of hTERT was markedly decreased.

Figure 2:
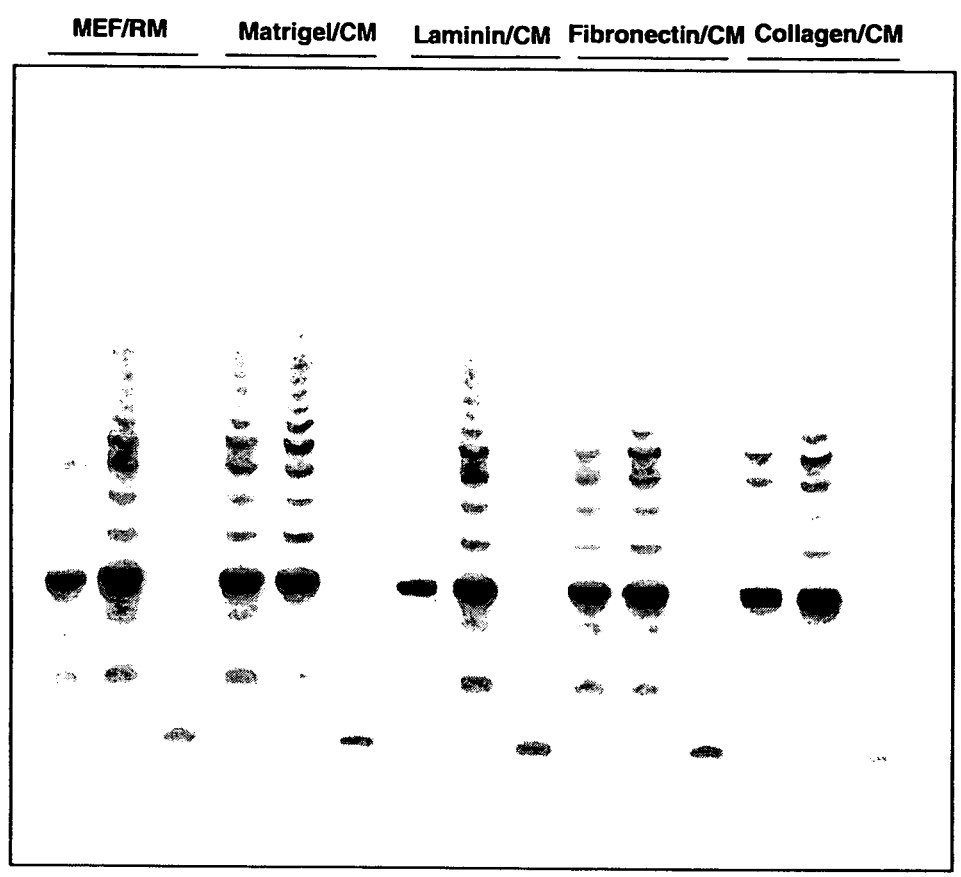
FIG. 2 is a half-tone reproduction of a gel showing telomerase activity measured in cultured hES cells by TRAP activity assay. All the culture conditions showed positive telomerase activity after 40 days in feeder-free culture.

FIG. 2 shows telomerase activity measured by TRAP activity assay (Kim et al., Science 266:2011, 1997; Weinrich et al., Nature Genetics 17:498, 1997). All the cultures conditions showed positive telomerase activity after 40 days on Matrigel®, laminin, fibronectin or collagen IV in mEF conditioned medium.

Example 3

Differentiation of hES Cells

In this experiment, differentiation using standard methods of aggregate formation was compared with a direct differentiation technique.

For the aggregate differentiation technique, monolayer cultures of rhesus and human ES lines were harvested by incubating in Collagenase IV for 5-20 min, and the cells were scraped from the plate. The cells were then dissociated and plated in non-adherent cell culture plates in FBS-containing medium. The plates were placed into a 37° C. incubator, and in some instances, a rocker was used to facilitate maintaining aggregates in suspension. After 4-8 days in suspension, aggregate bodies formed and were plated onto a substrate to allow for further differentiation.

For the direct differentiation technique, suspensions of rhesus and human ES cells were prepared in a similar fashion. The cells were then dissociated by trituration to clusters of ~50-100 cells, and plated onto glass coverslips treated with poly-ornithine. The cells were maintained in serum containing medium, or defined medium for 7-10 days before analysis.

Cells from both preparations were fixed and tested by immunoreactivity for β-tubulin III and MAP-2, which is characteristic of neurons, and glial fibrillary acidic protein (GFAP), which is characteristic of astrocytes. Results are shown in Table 1.

TABLE 1

Comparison of hPS Differentiation Methods

| ES Cell Line used for differentiation | | Differentiation via Aggregate Bodies | | Direct Differentiation | |
|---|---|---|---|---|---|
| | | Neurons | Astrocytes | Neurons | Astrocytes |
| R366.4 | (Rhesus line) | + | + | + | + |
| R278.5 | (Rhesus line) | + | + | + | + |
| R456 | (Rhesus line) | + | + | + | + |
| H9 | (Human line) | + | + | + | + |
| H9.1 | (Clone of H9) | (Not Done) | (Not Done) | + | + |
| H9.2 | (Clone of H9) | + | + | + | + |

Rhesus and human ES lines differentiated into cells bearing markers for neurons and astrocytes, using either the aggregate or direct differentiation technique. In the rhesus cultures, percentage of aggregates that contained neurons ranged from 49% to 93%. In the human lines examined, the percentage of aggregates containing neurons ranged from 60% to 80%. Double labeling for GABA and β-tubulin indicated that a sub-population of the neurons express the inhibitory neurotransmitter GABA. In addition, astrocytes and oligodendrocytes were identified with GFAP immune reactivity and GalC immune reactivity, respectively. Therefore, the human and rhesus ES cells have the capacity to form all three major cell phenotypes in the central nervous system.

The effect of several members of the neurotrophin growth factor family was examined. hES cells were differentiated by harvesting with collagenase, dissociating, and reseeding onto poly-ornithine coated cover slips. The cells were plated into DMEM/F12+N2+10% FBS overnight. The following day, the serum was removed from the medium and replaced with 10 ng/mL human bFGF and the growth factor being tested. After 24 hours, bFGF was removed from the medium. These cultures were fed every other day. They were fixed after 7 days of differentiation and immunostained for analysis. The number of neurons was evaluated by counting cells positive for β-tubulin. Cultures maintained in the presence of 10 ng/mL brain derived neurotrophic factor (BDNF) formed approximately 3-fold more neurons than the control cultures. Cultures maintained in neurotrophin-3 (1 ng/mL) formed approximately 2-fold more neurons than control cultures.

In a subsequent experiment, suspensions of human ES cells were prepared from parental line H9 and two subcloned lines. The cells were harvested using collagenase IV, and then replated onto poly-ornithine coated glass slides in medium containing 20% FBS. The cultures were then fed every other day for 7-10 days, then fixed for immunostaining. From each of these lines, a number of differentiated cells stained positively for muscle-specific actin (antibody from Dako), but were negative for cardiac troponin I. Several patches of cells stained positively for α-fetoprotein, indicating the presence of endoderm cells.

Example 4

Comparison of Direct Differentiation with Differentiation Through Embryoid Bodies To induce direct differentiation, undifferentiated hES cells were harvested and re-plated directly into differentiating conditions. Considerable cell death was apparent upon plating, but many cells adhered and began to proliferate and/or differentiate. In cultures differentiated using serum containing conditions, the cultures continued to proliferate and reached confluence within 5-10 days. At this time, the cultures contained a heterogeneous population that displayed many different morphologies. Immunocytochemistry revealed ectoderm, mesoderm and endoderm lineages using antibodies against β-tubulin III, muscle specific actin and α-fetoprotein, respectively. The positive staining for all of these cell types appeared in patches that were sometimes quite dense, therefore it was difficult to accurately quantify the percentages of each cell type.

In order to increase the percentage of neurons, the hES cells were plated onto poly-ornithine coated glass coverslips and cultures in defined media. Although these data indicate that cells from all three germ layers can be derived without the production of EBs, cardiomyocytes were not identified.

By way of comparison, hES cells were induced to differentiate by generating embryoid bodies (EBs). In these experiments, ES cells were harvested and replated in suspension cultures. Although initially a marked amount of cell death was observed, after 2-3 days the remaining cells formed aggregates. EBs were maintained for as many as 16 days in culture and were still viable and formed many structures after subsequent plating. Later stage human EBs often showed a cystic morphology and sometimes gave rise to beating EBs.

To assess cardiomyocyte formation, EBs were transferred to gelatin-coated plates or chamber slides after 4 days in the suspension cultures. The EBs attached to the surface after seeding, proliferated and differentiated into different types of cells. Spontaneously contracting cells were observed in various regions of the culture at differentiation day 8 and the number of beating regions increased until about day 10. In some cases, more than 75% of the EBs had contracting regions. Beating cells were morphologically similar to mouse ES cell-derived beating cardiomyocytes. In addition, the expression of the cardiac specific marker cardiac troponin I was examined at differentiation day 15 using immunocytochemistry. Individual contracting foci in the differentiated cultures were photographed to record the contracting area before the culture was fixed. The culture was then evaluated for cardiac cTnI expression and matched to the original photographs to determine the percentage of contracting areas that were positive for cTnI staining. As a control, cells adjacent to the contracting foci were also examined for cTnI staining. In these cultures 100% of the contracting areas showed positive immunoreactivity, while minimal immunoreactivity was observed in the non-beating cells.

Cultures of differentiated EBs were subjected to Western blot analysis using monoclonal antibody against cTnI. This assay gave a strong 31 kDa protein signal, corresponding to the size of the purified native human cardiac TnI. cTnI was detected in differentiated human ES cells containing contracting cells but not in undifferentiated ES cells or differentiated cultures with no evidence of contracting cells, suggesting the specific detection of cardiomyocytes. As a control, the blot was reprobed with β-actin specific antibody, confirming the presence of similar amounts of proteins in all samples.

In other experiments, EBs were cultured for 8 or 16 days and maintained as adherent cultures for an additional 10 days. RNA was prepared from the differentiated human ES cells and semiquantitative RT-PCR was performed to detect the relative expression of the endoderm-specific products $\alpha_1$-anti-trypsin, AFP, and albumin. Low levels of $\alpha_1$-anti-trypsin and AFP were detected in the undifferentiated cultures; little or no albumin was detected in the same cultures. All 3 markers were detected at significantly higher levels after differentiation. Expression of all 3 endoderm markers was higher in cultures derived from 8 day embryoid bodies than 16 day embryoid bodies.

Example 5

Transfection and Transduction of hES Cells Maintained on Primary mEF Feeder Layers hES cultures were maintained in a growth medium composed of 80% KO DMEM (Gibco) and 20% Serum Replacement (Gibco) supplemented with 1% non-essential amino acids, 1 mM glutamine, 0.1 mM β-mercaptoethanol and 4 ng/mL hbFGF (Gibco).

Plates were coated with a solution of 0.5% gelatin (Sigma) at 37° overnight before the addition of cells. Primary mEFs were cultured in standard mEF medium, and split 1:2 every 2 days for up to 5 splits. Subconfluent cultures of mEFs were detached with trypsin, resuspended in 10 mL medium, and irradiated with a cumulative dose of 3500-4000 rads with a Torrex™ 150D X-ray generator. Irradiated cells were pelleted at 400×g for 5 min and resuspended at $1.25 \times 10^5$ cells per mL in standard mEF medium. Individual wells of a 6-well plate were seeded with $3.75 \times 10^5$ irradiated mEFs per well; individual wells of a 24-well plate were seeded with 75,000 irradiated mEFs per well.

Transfection was performed as follows. hES cells plated in 6 well plates were removed from the feeder layer with collagenase (~200 units/mL) at 37° for 7-10 min. When colonies began to detach, the collagenase from each well was aspirated and replaced with 2 mL of standard hES growth medium/ well. The hES cells were removed by scraping the surface of a single well with a 5 mL pipet and transferred to a 50 mL conical tube. Additional hES growth medium was added to a final volume of 10 mL. The cell suspension was triturated 10-12 times with a 10 mL pipet, and an additional 8 mL of standard hES growth medium added. Three mL of the cell suspension were added to each well of 6 well plates that were pre-coated with gelatin and mEF feeder layers as described above (i.e., 1 well of a 6 well plate was sufficient to seed 6 wells of a new plate).

Replated hES cells were tested with a number of different transfection systems to determine whether genetic alteration of hES cells could be achieved without causing differentiation. Systems tested included the following: Mammalian Transfection Kit (CaPO4 and DEAE reagents), Stratagene cat #200285; TransIT-LT1 Mirus™ (Panvera), cat #MIR 2310; Polybrene (Sigma); Poly-L-Lysine (Sigma); Superfect™ (Qiagen); Effectene™ (Qiagen); Lipofectin™ (Life Technologies); Lipofectamine (differs from Lipofectamine 2000™) (Life Technologies); Cellfectin™ (Life Technologies); DMRIE-C (Life Technologies); Lipofectamine 2000 (Life Technologies); and electroporation using BioRad™ Gene pulser.

Under the conditions used, Lipofectamine 2000™ (Gibco Life Technologies cat #11668019, patent pending) and FuGENE™ (trademark of Fugent$_{L.L.C.}$; a proprietary blend of lipids and other components, purchased from Roche Diagnostic Corporation cat #1 814 443) both resulted in good transfection efficiency. The efficiency was generally best if these reagents were contacted with replated hES cells ~48 h after the replating.

Transfection using Lipofectamine 2000™ was conducted as follows: The plasmid DNA (3-5 µg of pEGFP-C1, ClonTech cat. #6084-1) was diluted in water to a final volume of 100 µl. In pilot experiments, 5 to 30 µL of Lipofectamine 2000™ (Gibco, cat #11668-019) were diluted in OptiMEM™ (Gibco, cat #11-58-021) to a final volume of 100 µL. The DNA solution was then added slowly to the Lipofectamine2000™ solution and mixed gently. The mixture was incubated at room temperature for 20-30 min before being supplemented with 800 µl of OptiMEM™. Cells were washed with 3 mL of pre-warmed OptiMEM™ and incubated in 0.5-1 mL of the DNA/lipid mixture solution at 37° C. for 4 h, per well (9.6 cm$^2$). In some experiments, at 4 h the complex was removed before the addition of 4 mL of mEF-conditioned medium; in others sufficient mEF-conditioned medium was added to the wells to reach a final volume of 3.5 mL and the mixture was left on the cells overnight. In other experiments the DNA/lipid mixture was added to wells containing sufficient mEF-conditioned medium such that the final volume was 3.5 mL, and the cells were incubated in this mixture overnight.

Transfection using FuGENE™ was conducted as follows. Each well was transfected with 10 µg DNA using FuGENE™ 6 (Roche Diagnostics Corp.), at a ratio of 3:2 FuGENE™ reagent to DNA as described by the manufacturer's directions. OptiMEM™ serum-free medium was used in the transfections. In the "old protocol", 4 h after the addition of the FuGENE™-DNA complex, 2.5 mL of standard hES growth medium was added to each transfected well. In the revised protocol ("3:2 L"), transfected wells were not re-fed with standard hES growth medium. Twenty-four hours after transfection, GFP-expression was assessed by flow cytometry.

Forty-eight hours before transfection, hES cells were seeded onto 6 well plates that had been coated with gelatin and mEF feeder layers as described above. hES cells were transfected using FuGENE™ 6 (Roche) or Lipofectamine 2000™ (Gibco) according to the manufacturers' instructions. Twenty-four hours after transfection, cells were assessed for GFP expression by inspection under a fluorescent microscope or flow cytometry. In the experiment shown in FIG. 1, three methods were compared: the standard Lipofectamine 2000™ protocol, the standard FuGENE™ protocol, and a variant FuGENE™ protocol in which the DNA/lipid mix was left on the cells overnight. The results demonstrated that while Lipofectamine 2000™ consistently yielded a higher percentage of GFP-expressing cells, the variant FuGENE™ protocol resulted in GFP-expressing cells with a higher mean fluorescence intensity.

Transient transductions using adenoviral vectors were conducted as follows. The vector Ad5CMV5-GFP (referred to here as Ad5GFP) contains the green fluorescent protein encoding region under control of the CMV promoter, and was purchased from Quantum Biotechnologies, cat #ADV0030. Seventy-two hours before transduction, hES cells were seeded onto 24 well plates that had been coated with gelatin and mEF feeder layers as described above. Before transduction, 3 wells of hES cells were detached with a solution of 0.05% trypsin/5 mM EDTA (Sigma) at 37°, resuspended in 500 µL of standard mEF growth medium, and counted with a hemocytometer (the 75,000 mEF feeder cells were subtracted from each well) to establish the cell number before transfection. The adenovirus stock was thawed on ice immediately prior to use.

For infection with Ad5GFP, growth media was aspirated from the wells containing hES cells and replaced with 1 mL of hES growth medium plus 9 µL of Ad5 GFP stock (MOI of 40). Two hours later, the virus-containing medium was replaced with 1 mL of hES growth medium per well. Each transduced well was refed with 1 mL of fresh hES growth medium every 24 hours. GFP expression was assessed by flow cytometry. The results from a typical experiment indicated that expression was highest at 24 hr after transduction but persisted for at least 8 days at low levels (by the later time points, extensive differentiation had occurred due to overgrowth of the hES cells).

Example 6

Preparation of the Immortalized Feeder Cell Line NH190

In this example, a permanent mouse cell line was established that is suitable for conditioning medium for the culture of primate pluripotent stem (pPS) cells. The NHG190 line is a mouse embryonic fibroblast cell line immortalized with telomerase that is triple drug resistant, and expresses green fluorescent protein (GFP).

Two mouse strains were obtained from Jackson Laboratory (Bar Harbor, Ma.) that have a transgene for resistance to the antibiotics neomycin or hygromycin. The C57BL/6J TgN (pPGKneobpA)3Ems mice and C57BL/6J-TgN (pPWL512hyg)1 Ems mice from Jackson Labs were crossbred. Embryos that were both neomycin- and hygromycin-resistant were dissected at day 13.5 post conception according to standard protocols for preparing mouse embryonic fibroblasts (mEF) for feeder layers (E. J. Robertson, pp. 71-112 in *Teratocarcinoma and Embryonic Stem Cell Lines*, ed. E. J. Robertson, Oxford: IRL Press, 1987). The derived mEF cells were stored frozen.

The mEFs were thawed in growth medium containing 20% fetal calf serum (HyClone), 2 mM L-glutamine (Gibco/BRL), 80% DMEM (Gibco/BRL). The cells were expanded using 1:2 split ratios for 4 passages. Two flasks that had reached ~75% confluence were fed with fresh medium 4 h before electroporation. Cells were removed from the flasks with 0.5% trypsin/500 mM EDTA (Gibco/BRL), pelleted at 400×g for 5 min at room temperature, and resuspended in the growth medium at a concentration of $4 \times 10^6$ cells/mL.

The cell suspension was divided into two 500 µL aliquots and transferred to two 0.4 cm gap electroporation curvets (BioRad). One cuvette received 5 µg of the control plasmid (pBS212; puromycin-resistance gene driven by the SV40 early enhancer/promoter); the other received 5 µg of pGRN190, comprising the murine telomerase reverse transcriptase (mTERT) coding region driven by MPSV promoter plus puromycin resistance gene driven by the SV40 early enhancer/promoter. The cells and DNA were mixed by hand, and electroporated using a BioRad gene Pulser with a BioRad capacitance extender at a setting of 300V, 960 µF.

Each aliquot of cells was transferred to an individual 150 cm plate containing 25 mL of growth medium. The medium on the plates was exchanged on the following day, and on the next day, growth medium was replaced by growth medium plus 0.5 µg/mL puromycin. The medium on the plates was exchanged for fresh puromycin-containing medium every 48 hrs until 29 days after electroporation. At this time, large individual colonies of puromycin-resistant cells were evident in both the pBS212- and pGRN190-electroporated plates. Ten colonies from the control plate and 12 from the pGRN190-electroporated plate were isolated with cloning cylinders and each colony was transferred to 1 well of a 48-well plate (1 well per colony).

One week later, all surviving colonies that had expanded to reach confluence in the 48 well plate (three control colonies, 1 pGRN190-electroporated colony) were transferred individually to wells of a 24 well plate. Six days later, the only colony that had continued to expand was derived from the pGRN190-electroporated plate, and was subsequently designated NH190. The cells were maintained in growth medium plus 0.5 µg/mL puromycin. Analysis for telomerase activity by TRAP assay (Kim et al., Nucleic Acids Res. 25:2595, 1997) demonstrated that NH190 cells express functional telomerase activity.

To facilitate monitoring of the cells in mixed culture populations and in vivo, NH190 cells were further infected with a retroviral construct conferring expression of green fluorescent protein (GFP). The enhanced GFP sequence from plasmid pEGFP-1 is one of the Living Colors™ fluorescent protein vectors, available from ClonTech. It contains an enhanced GFP encoding region, with changes that alter restriction nuclease cleavage sites, and shift the excitation and emission wavelengths of the encoded protein. The EGFP-1 sequence was cloned into the vector pMSCV neo, ClonTech cat #K1062-1. NH190 cells were transduced with the engineered vector, and GFP positive cells were separated by FACS sorting. The GFP expressing cell line was designated NHG190. These cells have been carried in culture for over 3 months.

Example 7

Genetic Modification of hES Cells Maintained on NHG190 Feeder Cells

NHG190 cells were cultured in DMEM (Gibco) plus 20% fetal bovine serum (HyClone) and 5 mM glutamine. Cells were split 1:10 every 3 d. Subconfluent cultures were detached with trypsin, suspended in 10 mL medium, and irradiated with a cumulative dose of 3500 rads with a Torrex™ 150D X-ray generator. Irradiated cells were pelleted at 400×g for 5 min and resuspended at $1.25 \times 10^5$ cells per mL in either NHG190 medium or standard hES medium.

Conditioned medium was prepared by plating NHG190 cells at $4.08 \times 10^4$ $cm^{-1}$ on gelatin-coated plates. At 18-24 h after plating, medium was exchanged for standard hES medium with 4 ng/mL added bFGF. The medium was conditioned by the cells for 18-24 h, harvested, and an additional 4 ng/mL bFGF was added. The medium was used to support hES cell cultures the same day as it was collected. Irradiated NHG190 cells could be used for preparing conditioned medium for 7-10 days.

hES cells were transfected as follows. The cells were removed from the feeder layer using collagenase (~200 U/mL) at 37° C. for 7-10 min, and transferred to a 50 mL conical tube. hES growth medium was added to a final volume of 10 mL; the suspension was triturated 10-12 times with a 10 mL pipet, and another 8 mL hES medium was added. Three mL of cell suspension was added to each well in a 6-well plate precoated with Matrigel® and NHG190 feeder cells.

Forty-eight hours after seeding, the hES were transfected with 10 µg DNA per well using FuGENE™ 6 (Roche) according to manufacturer's protocol in OptiMEM™ serum-free medium. The DNA was a plasmid containing the PGK promoter driving neo$^r$. Four h later, 3 mL of NHG190-conditioned medium was added to each transfected well. Cells were re-fed daily with 3 mL conditioned medium. Forty-eight h after transfection, the cells were layered with NHG190 conditioned medium containing 200 µg/mL added geneticin (Sigma), which was replaced daily thereafter. After 3 days of selection, additional irradiated NHG190 feeder cells were added ($1.25 \times 10^5$ cells/well in hES medium). Twenty-four h later, the medium was again replaced with NHG190-conditioned medium containing 200 µg/mL geneticin, replaced daily.

Individual colonies were isolated and expanded through another round of selection. After a further 5 days, individual colonies were identified by microscope and marked on the outside of the dish. Medium was removed, and replaced with collagenase (~200 U/mL). Individual colonies were picked using a p20 pipet tip, and transferred to individual tubes containing 2 mL NHG190 conditioned medium (without geneticin). The suspension was triturated 5 times to disaggregate colonies, and the contents of each tube were transferred to a well of a 12-well plate coated with gelatin and irradiated NHG190 cells ($1.875 \times 10^5$ cells/well). Cells were fed 24 h later with 2 fresh conditioned medium. Two days after seeding, cells were layered with 2 mL conditioned medium containing 200 µg/mL geneticin, replaced daily for 5 days. As each well became 50-75% confluent, the cells were detached with collagenase, transferred to 6 mL conditioned medium, and triturated 10-12 times. 3 mL cell suspension was added to each of 2 wells of a 6-well plated coated with gelatin and irradiated NHG190 cells ($3.75 \times 10^5$ cells/well); the cells were refed with 3 mL conditioned medium at 24 h. The cells were then selected for 5 days using 3 mL conditioned medium containing geneticin, and split 1:6 as before.

Stable transduction using retrovirus was conducted as follows. Retroviral vector designated GRN354 was constructed at Geron Corp. using PMSCVneo vector purchased from ClonTech (cat #K1062-1). The eGFP encoding region was inserted downstream from the MSCV LTR. The LTR drives expression of GFP and the vector also contains the neor gene driven by the murine PGK promoter. Plates were coated with 0.5% gelatin and NHG190 feeder cells ($7.5 \times 10^4$ in 1 mL NHG190 medium for 24 well plates; $3.75 \times 10^5$ in 3 medium for 6 well plates). The hES line H7 was seeded onto a 24 well prepared plate in hES medium (1 mL/well). Forty-eight h later, 3 wells of hES cells were detached using 0.05% trypsin/5 mM EDTA (Sigma) at 37° C., resuspended in 500 µL NHG190 medium, and counted. Stock of retrovirus construct pGRN354 was thawed on ice immediately prior to use. Growth medium was aspirated from the wells and replaced with 400 µL hES medium plus 8 µL retrovirus (MOI of 10) and 4 µL of 8 mg/mL polybrene solution (Sigma). Two h later, 800 µL hES growth medium were added per well. Each transduced well was refed with 1 mL fresh hES medium every 24 h.

Four days after transduction, medium was replaced with 1 mL hES growth medium containing 200 µg/mL geneticin. After 3 days of geneticin selection, the cells were detached with collagenase, triturated, resuspended in 3 mL hES medium, reseeded into one well of a 6-well plate coated with gelatin and NHG190 feeders, and refed with hES medium after 24 h. The medium was then again replaced with hES medium containing geneticin and refed every 24 h. Undifferentiated colonies survived the selection, and have been maintained for over 3 months. FACS analysis showed that 50-65% of the selected cells express GFP, albeit at low levels. The karyotype of the cells was normal.

Figure 3:
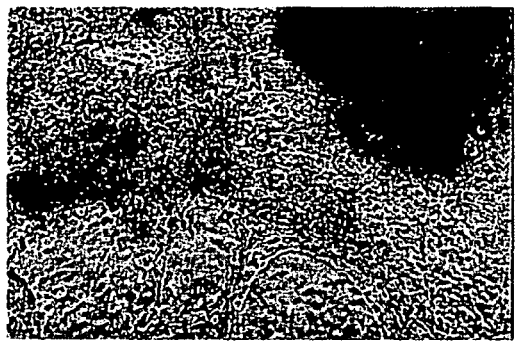
FIG. 3 is a half-tone reproduction showing expression of the GFP reporter gene in hES cells transduced with retrovirus and then differentiated. hES cells were transferred to suspension culture to form embryoid bodies, cultured for a further 4 days, replated onto gelatin-coated slides and cultured for a week, and then fixed and photographed under fluorescence for GFP expression. Left panels show bright-field illumination; right panels show fluorescence due to GFP expression.
Figure 3:
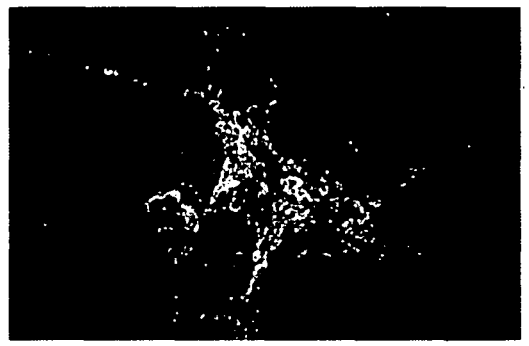
Figure 3:
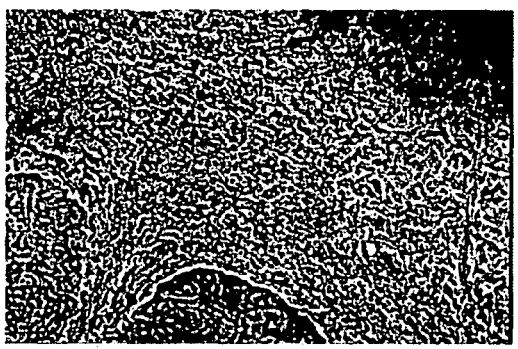
Figure 3:
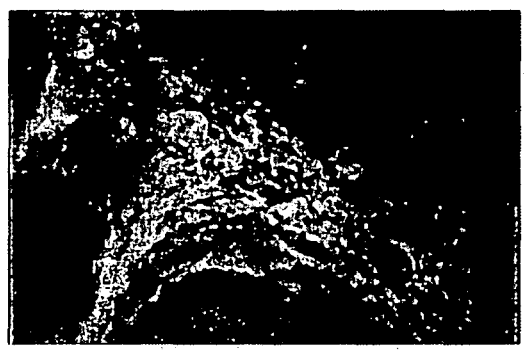

FIG. 3 shows GFP expression of hES cells transduced with retrovirus and then differentiated. The hES cell line H7 was plated on drug resistant (NHG190) feeder layers, infected with GRN354 and selected for resistance to the drug G418. Transduced cells were expanded and maintained under G418 selection for multiple passages. The cells were transferred to suspension culture to form embryoid bodies, allowed to differentiate for 4 days, and then plated in 20% FBS medium for 1 week. After extensive differentiation occurred, cultures were fixed in 4% paraformaldehyde and photographed under fluorescence for GFP expression. Many of the differentiated cells express higher levels of GFP than the undifferentiated transfected hES line, consistent with differential activation of the MESV-LTR in different cell types.

Example 8

Transfection of Feeder-Free hES Cells

In this example, hES cells maintained in feeder-free culture on laminin in conditioned medium were genetically modified by transfecting with a plasmid carrying green fluorescent protein (GFP) driven by the CMV promoter.

mEF conditioned medium was prepared as described earlier. mEFs were irradiated and seeded at about $5.7 \times 10^4$ cells/cm$^2$. After at least 16 hours the medium was exchanged with hES medium including 4 ng/mL added hbFGF. Conditioned medium was collected daily for feeding of hES cultures. Before addition to the hES cultures, this medium was supplemented with an additional 4 ng/mL of hbFGF. Where needed for selection of stable transfectants, the mEF-conditioned medium was supplemented with 200 µg/mL geneticin (Sigma cat. #G5013).

H9 hES cells maintained on mEF feeder layers were harvested from cultures by incubation with ~200 units/mL collagenase IV at 37° C. for 10 min. Cells were dissociated and resuspended in regular hES culture medium or mEF-conditioned medium. Cells in the regular medium were then re-seeded onto mEF feeder layers and cells in the mEF-conditioned medium were plated onto Matrigel® or laminin. Seeding density for all cultures was approximately $4 \times 10^4$ cells/cm$^2$. Cells on feeder layers were maintained in regular medium while cells on matrices were maintained in mEF-conditioned medium for 1 or 2 days before the transfection. Conditioned medium was replaced every 24 h.

hES cell cultures were transfected with Lipofectamine 2000™ as described above. FACS analysis of GFP expression was conducted as follows. hES cells were harvested using 0.5 mM EDTA in PBS and resuspended at approximately $1 \times 10^6$ cells/test. Cells were washed in a solution containing PBS plus 2% FBS, 0.1% sodium azide, and 2 mM EDTA. SSEA-4 staining was performed in the same buffer using antibody obtained from the Developmental Studies Hybridoma Bank (University of Iowa, Iowa City) at 1:15 dilution. Isotype matched controls were obtained from Sigma, (St. Louis Mo., USA). Cells were incubated with antibodies in a final volume of 100 µl for 30 min at 4° C., washed and incubated with rat anti-mouse κ chain antibodies conjugated with PE (Becton Dickinson, San Jose, Calif.) at 4° C. for 30 min. Samples were washed as before and analyzed for GFP and SSEA-4 expression on FACScalibur™ flow cytometer (Becton Dickinson, San Jose, Calif.) using CellQuest™ software.

hES cells of the H9 line maintained on laminin in mEF-conditioned medium were transfected with a plasmid carrying GFP driven by the CMV promoter at 24 or 48 h after plating. Initial experiments used a mixture of 5 µg of plasmid and 12 µL of Lipofectamine 2000™. Cells received 1 mL of DNA/lipid complex and were incubated for 4 h at 37° before the addition of 3 mL of mEF-conditioned medium, and then monitored for GFP expression 24 h after transfection.

Figure 4:
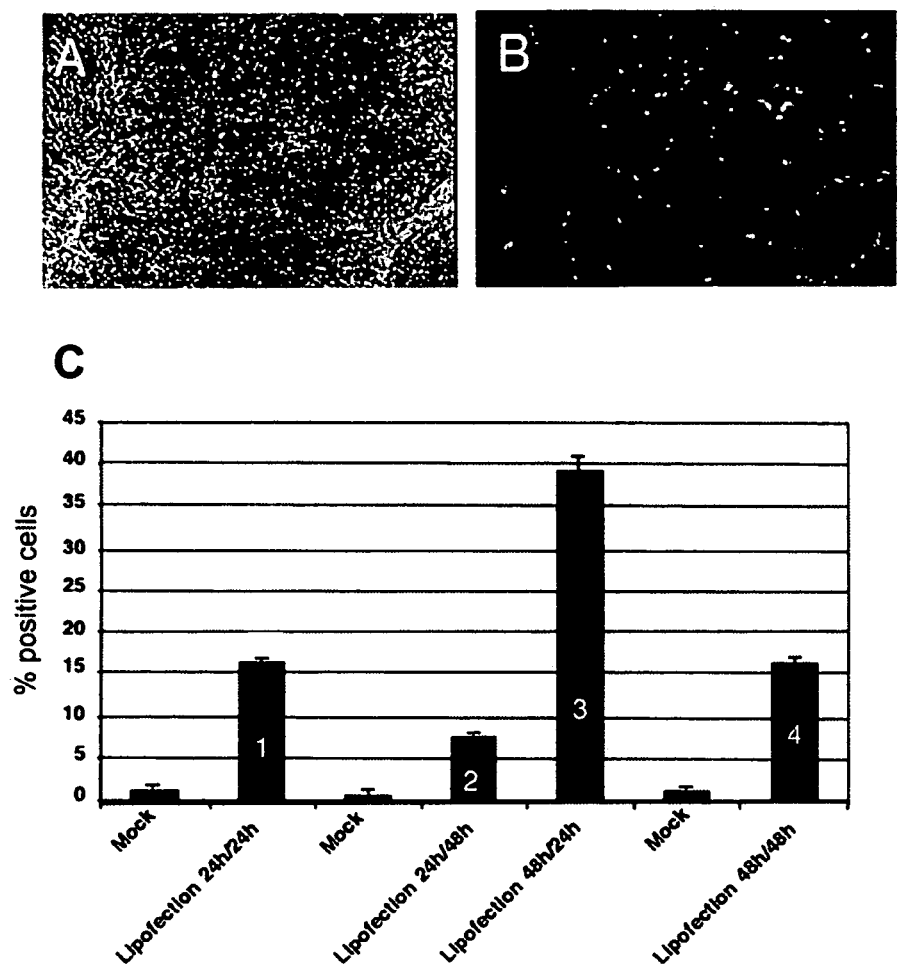
FIG. 4 shows the results of a study in which hES cells were transiently genetically altered in feeder-free culture by lipofection. Panel A is a half-tone reproduction of a light micrograph showing morphology of hES cells on laminin after they have been transfected. Panel B is a half-tone reproduction of a fluorescence micrograph showing GFP expression in the same colony. Panel C is a bar graph showing percentage of cells expressing GFP under various conditions.

FIG. 4 shows the results of this experiment. Panel A: morphology of H9 cells maintained on laminin. Panel B: GFP-positive cells observed in the same colony shown in A. Panel C: FACS analysis of % GFP-positive cells in SSEA-4 high population (undifferentiated cells). Cells were transfected 24 (bar 1 and 2) or 48 h (bar 3 and 4) after the seeding and analyzed 24 (bar 1 and 3) or 48 h (bar 2 and 4) after the transfection. Bright green cells were observed in compact areas of undifferentiated ES colonies on laminin 24 h after transfection (Panels A & B). Transfection at 48 h after initial seeding gave the highest efficiency: 38% of the cells were GFP-positive as determined by FACS analysis 24 h after the transfection (Panel C).

The next experiment compared the transfection efficiency of H9 cells maintained on Matrigel® or laminin-coated plates in mEF-conditioned medium with cells maintained on mEF feeders. Cells on feeder layers maintained in regular medium were used as a control. Morphological differences between cells on feeders and cells off feeders were observed 1 or 2 days after seeding. Colonies on feeders were more compact than cells maintained off feeder layers; individual hES cells in feeder-free cultures were less compact and flatter. There was no significant difference in cell or colony morphology between cells on laminin and cells on Matrigel. These cells were transfected with a plasmid expressing GFP driven by the CMV promoter 2 days after seeding. Twenty-four hours after the transfection, cells were examined for GFP expression under a fluorescence microscope.

The cells were maintained on mEF feeders in regular medium (mEF/RM), on laminin in medium conditioned by mEF (Laminin/CM) or on Matrigel® in the conditioned medium (Matrigel/CM). Bright green cells were observed in undifferentiated hES colonies of feeder-free cultures. In contrast, very few green cells were found in colonies on feeders. FACS analysis showed that 16% of cells on Matrigel® and 14% of cells on laminin were GFP positive in SSEA-4 high population while only 5% of cells on feeders were positive. These results indicate that transfection efficiency is significantly increased by using feeder-free conditions.

The next experiments evaluated the effects of 1) the ratio of DNA:lipid; 2) adding the DNA/lipid complex to cells 4 h prior to the addition of mEF-conditioned medium vs. addition of the complex to cells in the presence of mEF-conditioned medium; and 3) use of Lipofectamine 2000™ vs. FuGENE™.

Transfection using Lipofectamine2000™ is described above. Transfection with FuGENE™ was conducted as follows. The plasmid DNA (5-10 µg of pEGFP-C1, ClonTech cat. #6084-1) was diluted in water to a final volume of 100 µl. In pilot experiments, 5-30 µL of FUGENE™ were added to sufficient OptiMEM™ to achieve a final volume of 100 µL. The DNA solution was then added slowly to the FuGENE™ solution and mixed gently. The mixture was incubated at room temperature for 30 min before being supplemented with 800 µl of OptiMEM™. Cells were washed with 3 mL of pre-warmed OptiMEM™ and incubated in 1 mL of the DNA/lipid mixture solution at 37° C. for 4 h. In some experiments, at 4 h the wells received an additional 2 mL of mEF-conditioned medium; in others the DNA/lipid mixture was added to wells containing 2 mL of mEF-conditioned medium and the cells were incubated in this mixture overnight.

Highest efficiencies were obtained under the following conditions: Bar 1=a mixture of 5 µg plasmid plus 12 µl of Lipofectamine 2000™, adding 1 mL of the DNA/lipid mixture to wells containing 2.5 mL of mEF-conditioned medium and incubating the cells in this mixture overnight. Bars 2 & 3=a mixture of 10 µg plasmid plus 15 µl of FuGENE™ and incubating the cells in 1 mL of the DNA/lipid mixture for 4 h before adding 2.5 mL of mEF-conditioned medium. L=Lipofectamine2000™; F=FuGENE™.

To investigate whether the feeder-free hES cells undergo stable genetic modification, H1 hES cells maintained on Matrigel® were cotransfected with a mixture of 7.5 µg plasmid carrying β-galactosidase driven by the EF1a promoter, and 2.5 µg of plasmid carrying the PGK promoter driving the neophosphotransferase gene. The cells were transfected 48 h after plating them on Matrigel® in mEF-conditioned medium. 10 µg of plasmid plus 15 µl of FuGENE™ were incubated with the cells in 1 mL for 4 h before adding 2.5 mL of mEF-conditioned medium. After 48 h, medium was exchanged for mEF-conditioned medium supplemented with 200 µg/mL geneticin. Cultures were maintained in this geneticin-containing medium with daily medium exchange for over 21 days. All mock-transfected cultures (i.e., those that received FuGENE™ mixed with water rather than plasmid) died within 48-72 h. Drug resistant colonies arose in the wells transfected with both FuGENE™ and plasmid at a frequency of about 1 in to $10^5$ originally transfected cells. The colonies were maintained in geneticin-containing mEF-conditioned medium and expanded.

Example 9

Preparation of Vectors in Which a Thymidine Kinase Gene is Under Control of an hTERT Promoter Sequence The lambda clone designated λGΦ5 containing the hTERT promoter is deposited with the American Type Culture Collection (ATCC), 10801 University Blvd., Manassas, Va. 20110 U.S.A., under Accession No. 98505. λGΦ5 contains a 15.3 kbp insert including approximately 13,500 bases upstream from the hTERT coding sequence.

A Not1 fragment containing the hTERT promoter sequences was subcloned into the Not1 site of pUC derived plasmid, which was designated pGRN142. A subclone (plasmid "pGRN140") containing a 9 kb NcoI fragment (with hTERT gene sequence and about 4 to 5 kb of lambda vector sequence) was partially sequenced to determine the orientation of the insert. pGRN140 was digested using SalI to remove lambda vector sequences, the resulting plasmid (with removed lambda sequences) designated pGRN144. The pGRN144 insert was then sequenced.

SEQ. ID NO:1 is a listing of the sequence data obtained. Nucleotides 1-43 and 15376-15418 are plasmid sequence. Thus, the genomic insert begins at residue 44 and ends at residue 15375. The beginning of the cloned cDNA fragment corresponds to residue 13490. There are Alu sequence elements located ~1700 base pairs upstream. The sequence of the hTERT insert of pGRN142 can now be obtained from GenBank (http://www.ncbi.nim.nih.gov/) under Accession PGRN142.INS AF121948. Numbering of hTERT residues for plasmids in the following description begins from the translation initiation codon, according to standard practice in the field. The hTERT ATG codon (the translation initiation site) begins at residue 13545 of SEQ. ID NO:1. Thus, position −1, the first upstream residue, corresponds to nucleotide 13544 in SEQ. ID NO:1.

Expression studies were conducted with reporter constructs comprising various hTERT upstream and intron sequences. A BglII-Eco47III fragment from pGRN144 (described above) was digested and cloned into the BglII-NruI site of pSEAP2Basic (ClonTech, San Diego, Calif.) to produce plasmid designated pGRN148. A second reporter-promoter, plasmid pGRN150 was made by inserting the BglII-FspI fragment from pGRN144 into the BglII-NruI sites of pSEAP2. Plasmid pGRN173 was constructed by using the EcoRV-StuI (from +445 to −2482) fragment from pGRN144. This makes a promoter reporter plasmid that contains the promoter region of hTERT from approximately 2.5 kb upstream from the start of the hTERT open reading frame to just after the first intron within the coding region, with the initiating Met codon of the hTERT open reading frame changed to Leu. Plasmid pGRN175 was made by APA1(Klenow blunt)-SRF1 digestion and religation of pGRN150 to delete most of the Genomic sequence upstream of hTERT. This makes a promoter/reporter plasmid that uses 204 nucleotides of hTERT upstream sequences (from position −36 to −117). Plasmid pGRN176 was made by PML1-SRF1 religation of pGRN150 to delete most of the hTERT upstream sequences. This makes a promoter/reporter plasmid that uses 204 nucleotides of hTERT upstream sequences (from position −36 to −239).

Levels of secreted placental alkaline phosphatase (SEAP) activity were detected using the chemiluminescent substrate CSPDTM (ClonTech). SEAP activity detected in the culture medium was found to be directly proportional to changes in intracellular concentrations of SEAP mRNA. The pGRN148 and pGRN150 plasmids (hTERT promoter-reporter) and the pSEAP2 plasmid (positive control, containing the SV40 early promoter and enhancer) were transfected into test cell lines. pGRN148 and pGRN150 constructs drove SEAP expression as efficiently as the pSEAP2 in immortal (tumor-derived) cell lines. Only the pSEAP2 control gave detectable activity in mortal cells.

The ability of the hTERT promoter to specifically drive the expression of the thymidine kinase (tk) gene in tumor cells was tested using a variety of constructs: One construct, designated pGRN266, contains an EcoRI-FseI PCR fragment with the tk gene cloned into the EcoRI-FseI sites of pGRN263. pGRN263, containing approximately 2.5 kb of hTERT promoter sequence, is similar to pGRN150, but contains a neomycin gene as selection marker. pGRN267 contains an EcoRI-FseI PCR fragment with the tk gene cloned into the EcoRI-FseI sites of pGRN264. pGRN264, containing approximately 210 bp of hTERT promoter sequence, is similar to pGRN176, but contains a neomycin gene as selection marker. pGRN268 contains an EcoRI-XbaI PCR fragment with the tk gene cloned into the EcoRI-XbaI (unmethylated) sites of pGRN265. pGRN265, containing approximately 90 bp of hTERT promoter sequence, is similar to pGRN175, but contains a neomycin gene as selection marker.

These hTERT promoter/tk constructs, pGRN266, pGRN267 and pGRN268, were re-introduced into mammalian cells and tk/+ stable clones (and/or mass populations) were selected. Ganciclovir treatment in vitro of the tk/+ cells resulted in selective destruction of all tumor lines tested, including 143B, 293, HT1080, Bxpc-3′, DAOY and NIH3T3. Ganciclovir treatment had no effect on normal BJ cells.

Figure 5:
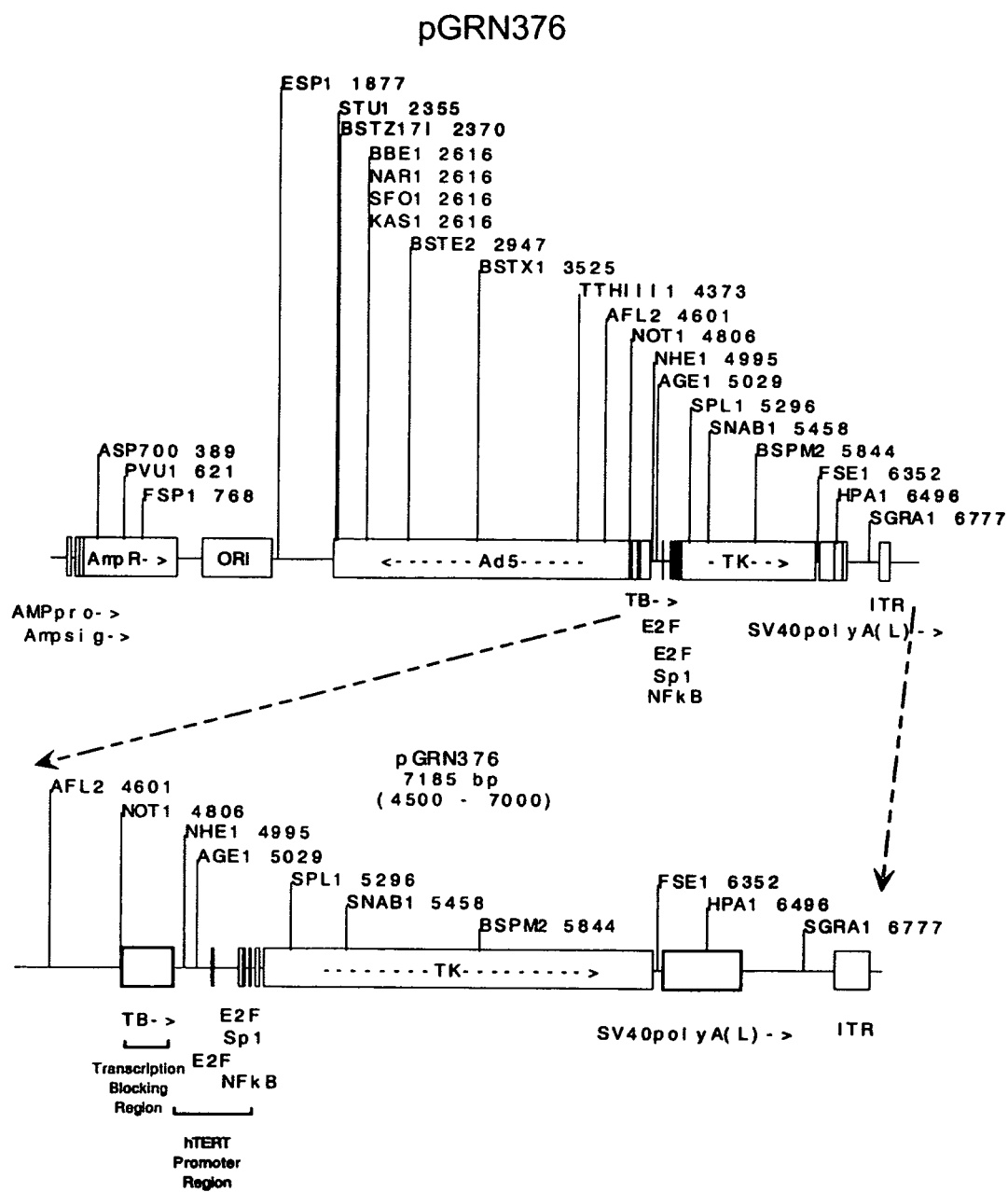
FIG. 5 is a map of $T_{PAC}$ vector designated pGRN376. This is an adenovirus vector of 7185 bp comprising the herpes simplex thymidine kinase (tk) gene under control of a promoter taken from the upstream sequence of the human gene for telomerase reverse transcriptase (hTERT). Expression of tk is promoted in cells expressing hTERT, such as undifferentiated embryonic stem cells.

FIG. 5 is a map of the $T_{PAC}$ adenovector pGRN376. It was made by cloning the NOT1-BAMH1 fragment from pGRN267 into the NOT1-BGL2 sites of pAdBN (Quantum Biotech). The 7185 bp vector comprises the herpes simplex thymidine kinase (TK) gene under control of the medium-length hTERT promoter sequence.

Example 10

Transduction of hES Cells with a Thymidine Kinase Construct

These experiments test the effect of the pGRN376 vector described in the preceding Example on hES cells. The vector contains the herpes virus thymidine kinase gene under control of the telomerase reverse transcriptase promoter. Expression of the thymidine kinase gene in cells should render them susceptible to toxicity from the prodrug ganciclovir.

Undifferentiated H1 cells were plated into 24 well plates (1 confluent well of a 6 well plate split into 24 wells of a 24 well plate). After 48 h, some wells were infected with the $T_{PAC}$ vector at an MOI of 30 or 100. Four h after addition of the viral vector, medium was exchanged for new mouse embryonic fibroblast conditioned medium (mEF-CM); some wells received medium supplemented with 30 μM ganciclovir (GCV). Cells exposed to GCV were re-fed with mEF-CM containing 30 μM GCV daily for 4 days. On days 2, 3, and 4 after the initiation of GCV treatment, wells were harvested and analyzed by flow cytometry to assess changes in 1) total cell number and 2) cell viability (measured by PI exclusion).

Figure 6:
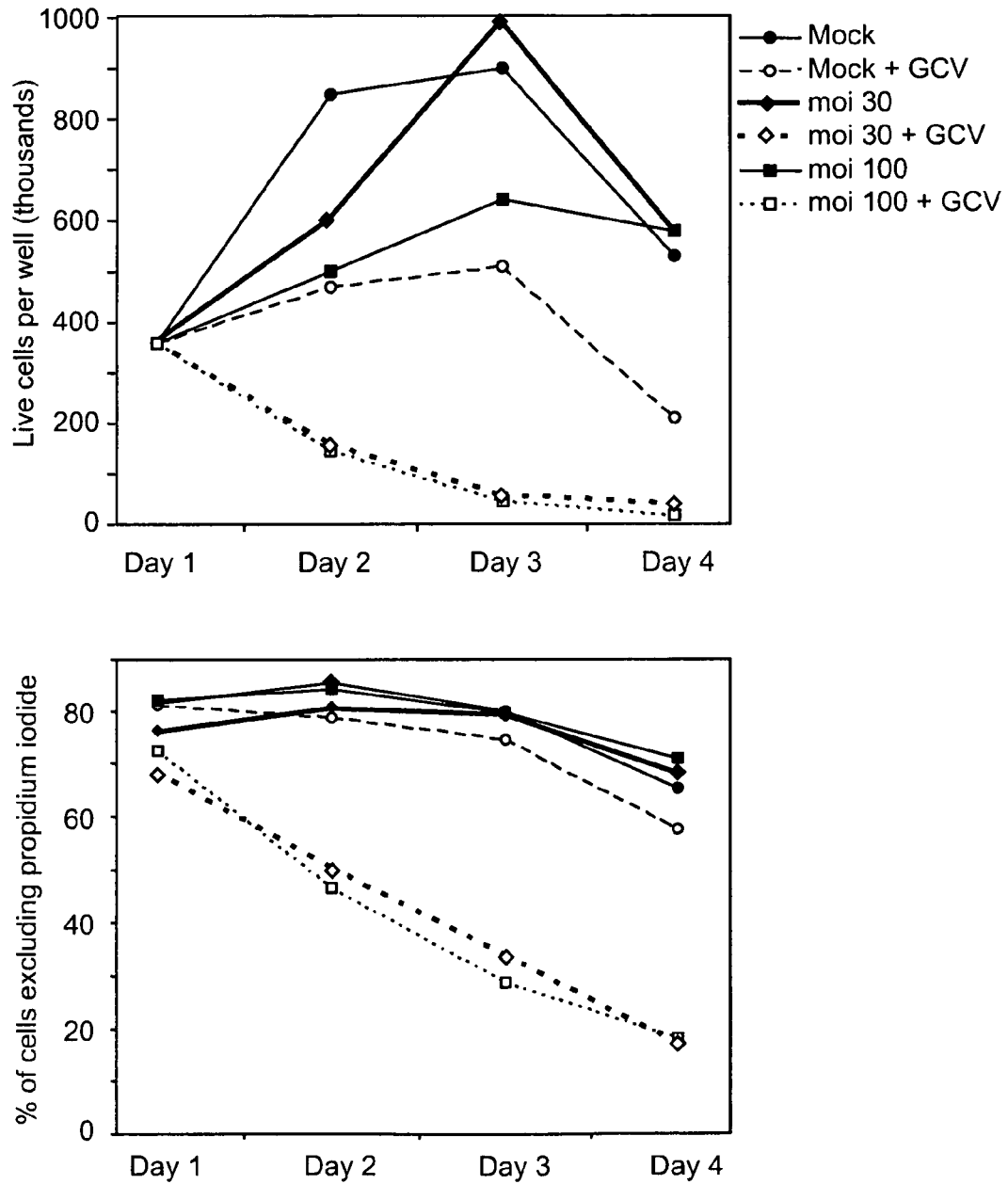
FIG. 6 is a two-panel line graph, showing the effect of the $T_{PAC}$ thymidine kinase vector on undifferentiated hES cells. 48 h after replating, the cells were transduced with $T_{PAC}$ vector at an MOI of 30 or 100, or mock transduced (no vector added). Four h later, the cells were exchanged into fresh medium containing the prodrug ganciclovir (GCV). By day 3, wells treated with $T_{PAC}$ vector+GCV contained 8% as many cells as the control wells.

FIG. 6 shows the results of this experiment. No change in total cell number was detected at MOI of 30 in the absence of GCV; but there was some decrease at MOI of 100 in absence of GCV starting at 48 h. Evidence for toxicity of GCV alone was detected: wells receiving GCV alone contained approximately 55% as many cells as the control wells on day 2, diminishing to 40% by day 4. Wells receiving GRN376 at MOIs of 30 or 100 cultured in the presence of GCV showed identical results: by day 2, these wells contained 18% of the cells contained in the control wells, while at days 3 and 4 these wells contained 6% and 8% of the cells in the control wells.

Slight toxicity was seen at MOI of 100 at day 4 in the absence of GCV (50% cells in ES gate vs. 83% for the control cells). Some toxicity of GCV alone was observed at d2, 75% cells in ES gate (vs. 85% control); at day 3, 68% (vs. 82% control); at day 4, 50% (vs. 65% control). Wells receiving GRN376 at MOIs of 30 or 100 cultured in the presence of GCV showed similar results: by day 2, these wells contained 24-28% cells in the ES gate, at day 3 they contained 19-22% cells in the ES gate, and at d4 these wells contained 12% cells in the ES gate. Thus, GRN376 plus GCV is effective at killing undifferentiated hES cells at an MOI as low as 30.

Titration Experiment

Undifferentiated H1 cells were plated into 24 well plates (1 confluent well of a 6 well plate split into 24 wells of a 24 well plate). After 48 h, some wells were infected with pGRN376 at an MOI of 30. Four h after addition of the viral vector, medium was exchanged for new mEF-CM; some wells received medium supplemented with 5, 10, 20, 30, or 40 μM ganciclovir (GCV). Cells exposed to GCV were re-fed with mEF-CM containing GCV daily for 2 days. On day 2 after the initiation of GCV treatment, wells were harvested and analyzed by flow cytometry to assess changes in total cell number, and cell viability (measured by PI exclusion).

Figure 7:
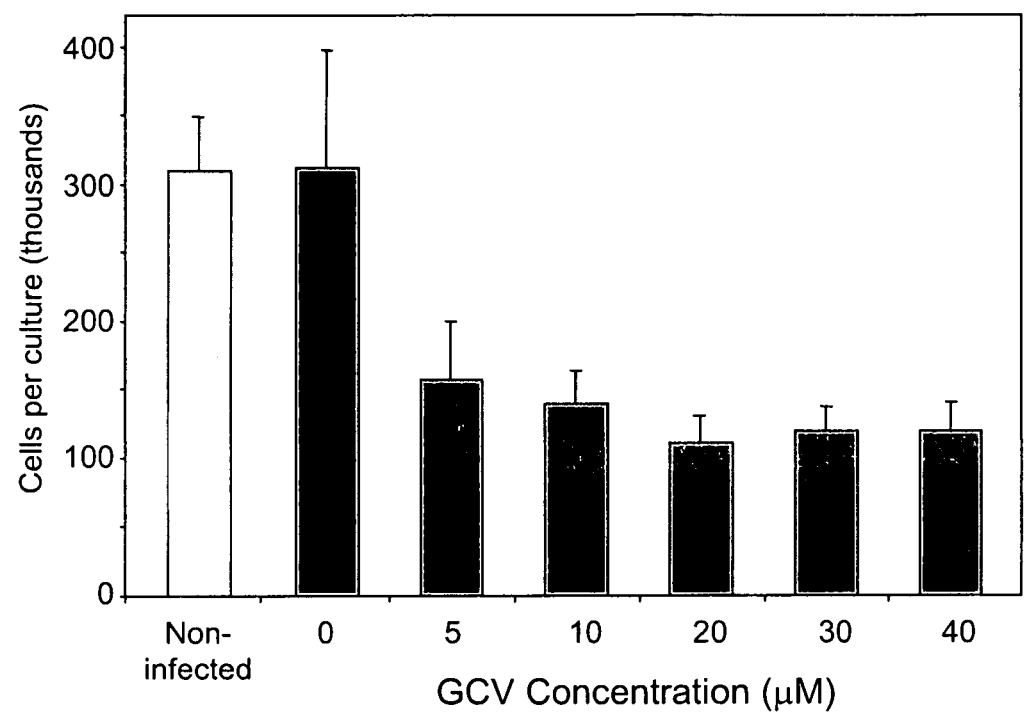
FIG. 7 is a bar graph showing titration of GCV in $T_{PAC}$ vector treated hES cells. 4 h after transduction with the vector, fresh medium was added containing GCV at the concentration shown. ~20 µM GCV was optimal under the conditions tested.

FIG. 7 shows the results of this experiment. ~20 μM GCV was optimal under the conditions tested.

Comparison of Different hES Lines

Undifferentiated hES of lines designated H1 and H7 cells were plated into 24 well plates (1 confluent well of a 6 well plate split into 24 wells of a 24 well plate). After 48 h, some wells were infected with pGRN376 at an MOI of 30. Four h after addition of the viral vector, medium was exchanged for new mEF-CM; some wells received medium supplemented with 20 μM GCV. Cells exposed to GCV were re-fed with mEF-CM containing GCV daily for 3 days. On day 4 after the initiation of GCV treatment, wells were harvested and analyzed by flow cytometry to assess changes in total cell number.

Figure 8:
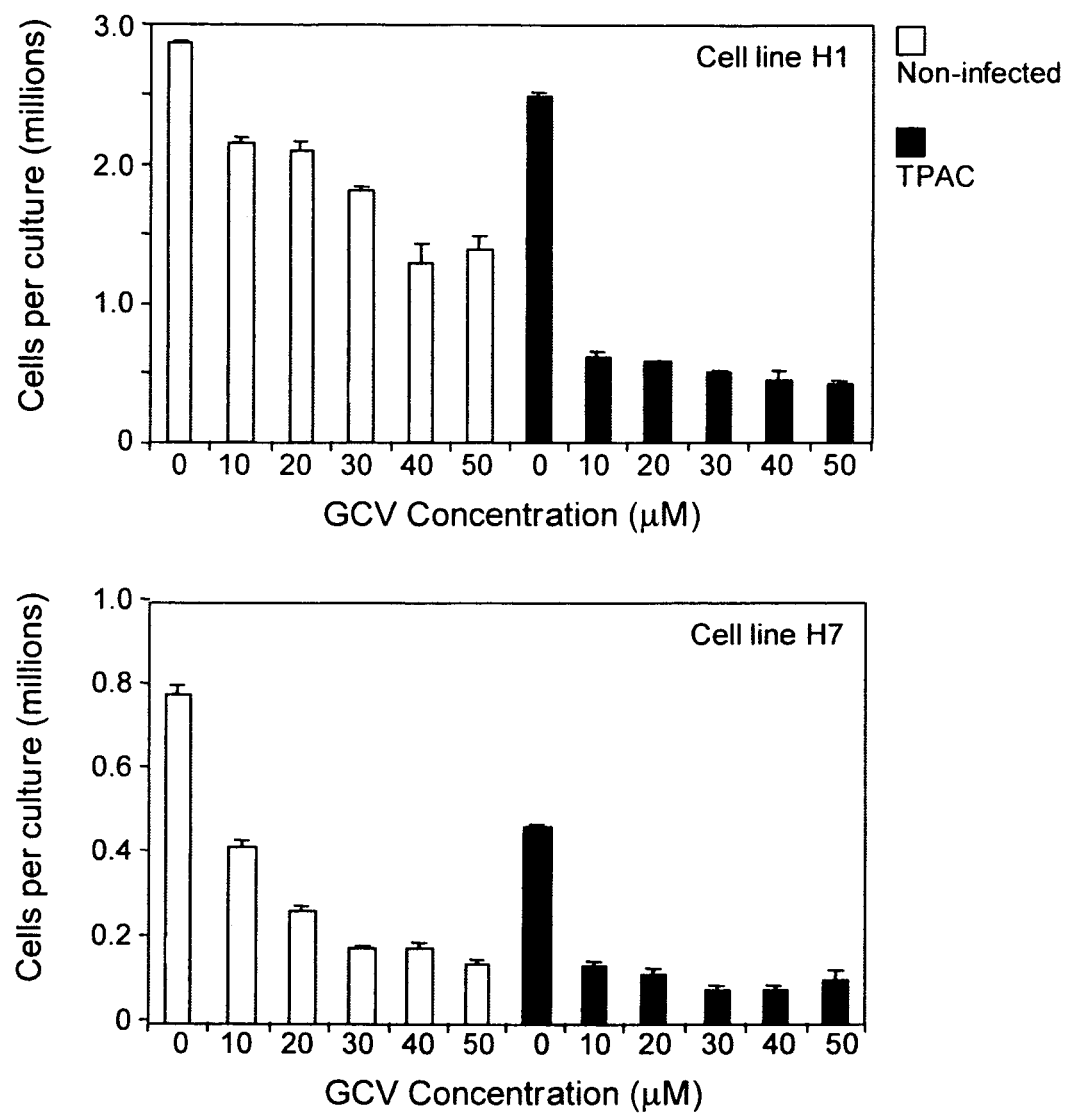
FIG. 8 is a two-panel bar graph showing titration of GCV on $T_{PAC}$ vector transduced and mock-transduced hES cells from two different lines. Both lines are sensitive to GCV after treatment with the $T_{PAC}$ vector.

FIG. 8 shows the results. The total cell number demonstrated decreases in cell number for both lines after $T_{PAC}$ vector treatment. H7 showed less toxicity induced by GCV alone than did H1. Thus, different hES cell lines respond to the $T_{PAC}$ vector. In subsequent studies, the H9 cell line was also found to be highly sensitive to GCV after $T_{PAC}$ vector treatment.

Example 11

Selection of Differentiated Cells

In this experiment, hES cells were treated with retinoic acid (RA) or dimethyl sulfoxide (DMSO), and then analyzed for hTERT and OCT-4 expression after treating with $T_{PAC}$.

Undifferentiated H1 cells were plated into 24 well plates (1 confluent well of a 6 well plate split into 24 wells of a 24 well plate). 24 h later, some wells were re-fed with mEF-CM containing either 500 nM RA or 0.5% DMSO; wells were re-fed with medium supplemented with RA or DMSO for the remainder of the experiment. After 7 days of treatment with RA or DMSO, cells were infected with GRN376 at an MOI of 30.

Four h after addition of the viral vector, medium was exchanged for new mEF-CM (plus RA or DMSO where appropriate); some wells also received medium supplemented with 20 μM ganciclovir (GCV). Cells exposed to GCV were re-fed with mEF-CM containing GCV daily for 3 days. On day 3 after the initiation of GCV treatment, wells were harvested and analyzed by flow cytometry to assess changes in total cell number. Additional wells were used in an effort to culture out any remaining undifferentiated stem cells; the medium of these wells was changed to mEF-CM (without RA, DMSO, or GCV). Cells were refed with mEF-CM every day for 7 days, then harvested for isolation of RNA. These samples were analyzed by quantitative RT-PCR for the expression of hTERT and OCT-4.

Figure 9:
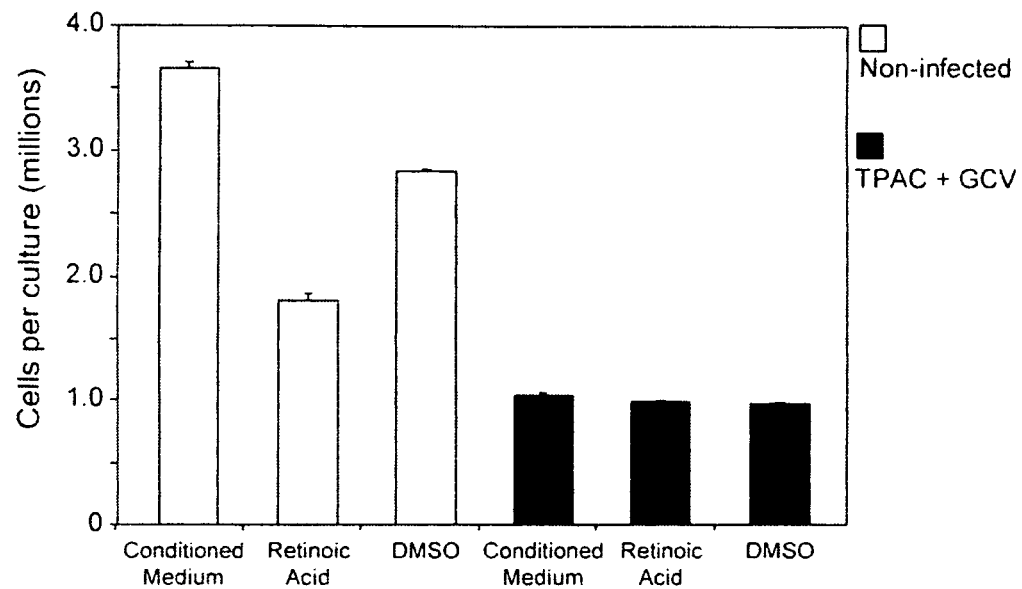
FIG. 9 shows the effect of $T_{PAC}$+GCV treatment on mixed cell populations obtained from differentiation of hES cells. The cells were fed daily with conditioned medium to maintain the undifferentiated state, or with either 500 nM retinoic acid or 0.5% DMSO, to induce differentiation into committed cells of mixed phenotype. 7 days later, they were infected with the $T_{PAC}$ vector at an MOI of 30, plus 20 µM GCV.
Figure 9:
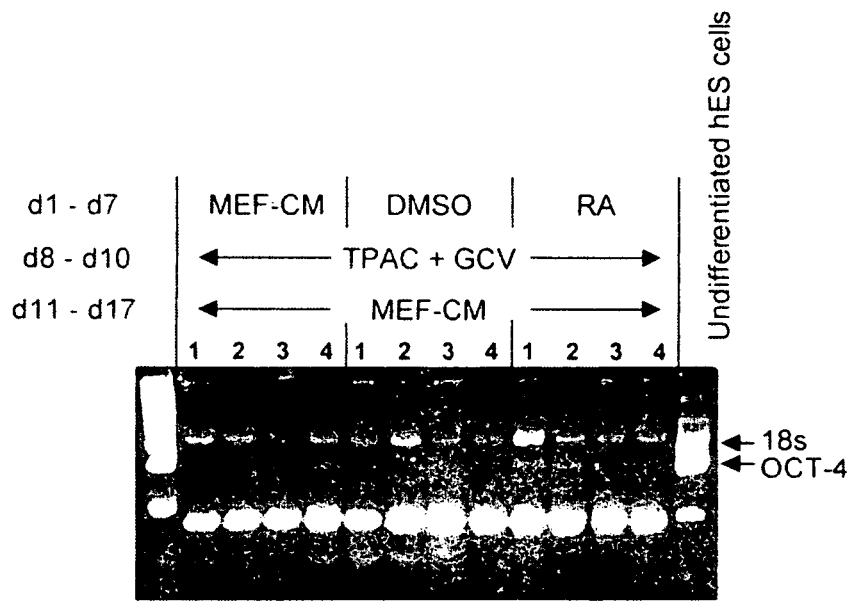

FIG. 9 shows that the cell number decreased after $T_{PAC}$ treatment. After 7 days of drug pretreatment followed by $T_{PAC}$ plus GCV, all wells contained similar cell numbers. During the attempt to culture out surviving stem cells, the wells became confluent with highly differentiated appearing cells; no undifferentiated hES cells were obvious. Wells containing cells that had been pre-treated with RA were distinct in appearance from the cells either pre-treated with unadulterated mEF-CM or treated with mEF-CM plus DMSO. RT-PCR analysis (Lower Panel, non-quantitative, 35 cycles) showed that the surviving cells from the mEF-CM or DMSO-treated wells had no detectable OCT-4 expression, while 2 out of 4 RA-pre-treated samples presented very weak OCT-4 PCR products.

Thus, no detectable undifferentiated cells survive $T_{PAC}$ treatment followed by subsequent culture of wells grown in mEF-CM or mEF-CM plus DMSO. RA pre-treatment leads to detection of low levels of OCT-4 in the surviving cells. It is not clear whether this reflects persistence of undifferentiated stem cells or induction of another cell type that expresses OCT-4.

Example 12

Stable Stem Cell Lines Containing the $T_{PAC}$ Construct

To facilitate creation of stable cell lines genetically altered with the hTERT promoter/thymidine kinase construct, plasmid pGRN376 (Example 9) was modified to delete most of the adenovirus sequence. The plasmid was digested with StuI and Not I, followed by blunting and re-ligation. The remaining vector contained the hTERT promoter/thymidine kinase construct, preceded by the transcription blocking sequence to prevent promotion of tk gene expression by promoter sequences upstream from the integration site in the genome. The modified vector was designated pGRN376mod.

| pGRN376 - adenoviral TPAC vector | | | | |
|---|---|---|---|---|
| Ad5 | TRM | pTERT 216 bp | HSV TK | SV40 polyA |

| pGRN376mod - TPAC plasmid vector | | | |
|---|---|---|---|
| TRM | pTERT 216 bp | HSV TK | SV40 polyA |

Cultures of the H9 hES cell line were split 1:4 using PBS containing 0.5 mM EDTA, as described earlier, and plated in feeder-free culture in 6-well plates. Twenty-four hrs after plating, cells were cotransfected with 2 μg GRN376mod plus 0.5 μg of a plasmid encoding neomycin phosphotransferase, using FuGENE™-6 as described above. Medium containing 200 μg/mL geneticin was added 48 h after transfection to select out transfected cells. After 7-10 days in geneticin-containing medium, 103 individual colonies were picked from the wells and individually plated in 24-well plates, which were then expanded by culturing for ~7 days. Ninety individual clones were screened for sensitivity to the pro-drug ganciclovir at a concentration of 30 μM. Ten clones were identified in which essentially all the undifferentiated cells died within 1-3 days of culture with ganciclovir, leaving only remnant cells that had differentiated outside the main colony.

In another experiment, the H1 line of hES cells (passage 59) was split 1:6 into Matrigel®-coated 24 well plates in standard hES cell medium (day 0; 1 ml/well, MEF conditioned medium with 4 ng/mL bFGF). The medium was exchanged with new standard medium on the following day. On day 3, the medium was removed and replaced with either 200 μL/well standard medium (mock transfection), or pGRN376 virus at MOI 100, diluted in 200 μL/well standard hES medium. After 4 h, the medium was removed from all wells and replaced with 1 mg/mL standard hES medium with or without 30 μM ganciclovir. The wells were exchanged with fresh medium (with or without 30 μM ganciclovir) on each of the next three days.

FIG. 10 is a micrograph of the cells on day 6. In wells transduced with control vector (Panel A), hES colonies formed colonies with normal characteristics. In wells transduced with pGRN376 virus and then treated with ganciclovir (Panel B), most or all ES cell colonies are gone and only differentiated cells remain. The $T_{PAC}$-treated wells contained 8-fold fewer cells than the control wells.

Example 13

Further Characterization of Stable $T_{PAC}$ Embryonic Stem Cell Lines $T_{PAC}$ stable clones were derived by co-transfection of pGRN376mod and pGK-neo plasmids into the hES cell line H9 grown in mEF conditioned media with basic FGF on growth factor reduced Matrigel® coated plates.

In one experiment, the H9 line (p 80) was passaged 6 times using 0.5 mM EDTA prior to transfection. 2 μg of pGRN376m plasmid and 0.5 μg of pGK-neo plasmid were used for transfection of each well of a 6 well plate of ES cells, using a 3:2 ratio of Fugene™ (a lipid-based transfection facilitator) to DNA. The cells were transfected 24 hours after seeding, and G418 selection was initiated 24 h post-transfection. 101 G418-resistant colonies were picked using collagenase. Clones from cells transfected only with pGK-neo were isolated as controls for co-transfection.

Individual colonies were expanded using 0.5 mM EDTA for primary and secondary GCV screening. Primary screen with 30 µM GCV (weeks 1 and 2) identified 10 GCV-sensitive clones and 20 partially GCV-sensitive clones. Secondary screen with 30 µM GCV (weeks 3 and 4) confirmed 9 GCV-sensitive clones, including those designated H9-376m-18, H9-376m-77, and H9-376m-62. Following secondary GCV screening, cells were expanded using 0.5 mM EDTA into larger cultures and then passaged using collagenase.

In a second experiment, the H9 line (p 24) was again initially passed using 0.5 mM EDTA, and then transfected as before. Sixty two G418-resistant co-transfected colonies were picked using collagenase on day 0. Primary screen with 30 µM GCV (days 20, 22, and 26) identified one GCV-sensitive clone and four partially GCV-sensitive clones. Following primary GCV screening, cells were expanded using 0.5 mM EDTA into larger cultures and gradually returned to standard collagenase passaging. Secondary screen with 30 µM GCV (day 57) confirmed one GCV-sensitive clones (designated H9-376m-6).

The GCV-sensitive clones from each of these experiments were subject to further selection in culture with G418, to determine their stability. Clones designated H9-376m-18 and H9-376m-77 showed G418 resistance that was not stable. Clones designated H9-376m-62, H9-376m-6, and H9-pGK-neo-1 were G418 resistant.

FIG. 11 (top) shows sensitivity of the stable $T_{PAC}$ lines to ganciclovir (GCV). Each cell line was exposed to decreasing amount of GCV to determine lowest concentration of GCV required to produce complete killing of undifferentiated ES cells with the least amount of toxicity. Concentrations as low as 0.5 µM were determined to kill undifferentiated ES cells similar to 30 µM, but with a significantly lower toxicity.

FIG. 11 (bottom) shows sensitivity of the $T_{PAC}$ lines to a different prodrug, (E)-5-(2-bromovinyl)-2'-deoxyuridine (BVDU). Although a significant decrease on cell counts was observed with all BVDU concentrations tested, ES cell killing was not actually observed. The number of cells present even at high concentrations of BVDU is not reduced to the level of the blank control.

To verify expression of HSV-TK in stable $T_{PAC}$ ES cell lines, RT PCR was performed on undifferentiated cells from H9-376m-6, H9-376m-62 and H9-pGK-neo-1 cultures using HSV-TK or OCT-4 specific primers. TK expression was detected in H9-376m-6 and H9-376m-62 samples and not in H9-pGK-neo samples at high concentrations of RNA, while OCT-4 expression was detected in all samples.

Example 14

Promoter Specificity for Undifferentiated Cells

To determine hTERT promoter specificity on in the stable $T_{PAC}$ clones, GCV sensitivity was determined after differentiation of each $T_{PAC}$ clone and the pGK-neo control clone.

Undifferentiated cells were seeded in growth factor reduced Matrigel® coated plates with KO DMEM plus 20% Hyclone FBS without bFGF (differentiation conditions). Cultures were maintained in differentiation conditions for 7 days, passaged and placed in the differentiation conditions for additional 4 days. Following this treatment, cultures contained few if any undifferentiated cells (assessed by morphology). At this point, 30 µM GCV was added to the differentiated cultures for 4 days.

There was no sensitivity to GCV observed in differentiated cultures obtained from the $T_{PAC}$ cell lines H9-376m-6, H9-376m-62, H9-376m-18, or H9-376m-77; or from the transfection control line H9-pGKneo. Thus, the hTERT promoter in the integrated construct has the appropriate specificity for turning on the TK effector gene only in undifferentiated cells.

Example 15

ES Marker Expression in Undifferentiated $T_{PAC}$ Cell Lines

Expression of ES markers on stable $T_{PAC}$ ES cell lines was determined by flow cytometry. Cells were harvested from confluent cultures using 0.5 mM EDTA and incubated with monoclonal antibodies against human SSEA-4, SSEA-1, Tra-1-60, Tra-1-81, CD9, AC133, and appropriate fluorochrome-conjugated secondary antibodies. Level of expression was determined using FACSCalibur™. Appropriate isotype matched negative controls and viability assessment were used to determine the level of non-specific binding.

TABLE 2

Markers on Parental hES cells and Stable TPAC Lines

| | Phenotypic marker | | | | | |
|---|---|---|---|---|---|---|
| | H9 p 35 | H9-376m-62 p 80 + 15 | H9 p 25 | H9-pGK-neo p 24 + 16 | H9-376m-6 p 24 + 19 | H9-376m-62 p 80 + 27 |
| SSEA4+ | 92* | 100 | 64 | 37 | 91 | 98 |
| SSEA1+ | 1 | 0 | 0 | 0 | 0 | 0 |
| Tra-1-60+ | 98 | 99 | 89 | 89 | 86 | 90 |
| Tra-1-81+ | 96 | 99 | 82 | 88 | 77 | 97 |
| CD9+ | 88 | 95 | 81 | 98 | 91 | 99 |
| AC133+ | 90 | 81 | 72 | 78 | 68 | 70 |

*% of live cells expressing markers.

H9-376m-6, H9-376m-62 and H9-pGK-neo-1 cell lines have expression of all tested ES markers at the levels comparable to those of untransfected H9 cell line.

Example 16

Ability of $T_{PAC}$ Cell Lines to Undergo Appropriate Differentiation

H9-376m-6, H9-376m-62, H9-376m-77, H9-376m-18 and H9-pGK-neo-1 were tested for their ability to generate cells from three embryonic germ lineages. Embryoid bodies (EBs) were established from each cell line and cultured in suspension with KO DMEM and 20% Hyclone FBS. Following 4 day culture, EBs were plated on gelatin-coated chamber slides and allowed to grow for additional 8-10 days. Cultures were scored for the presence of beating cells and stained for the presence of β-tubulin, AFP, muscle-specific actin and cardiac troponin I positive cells.

Figure 12B:
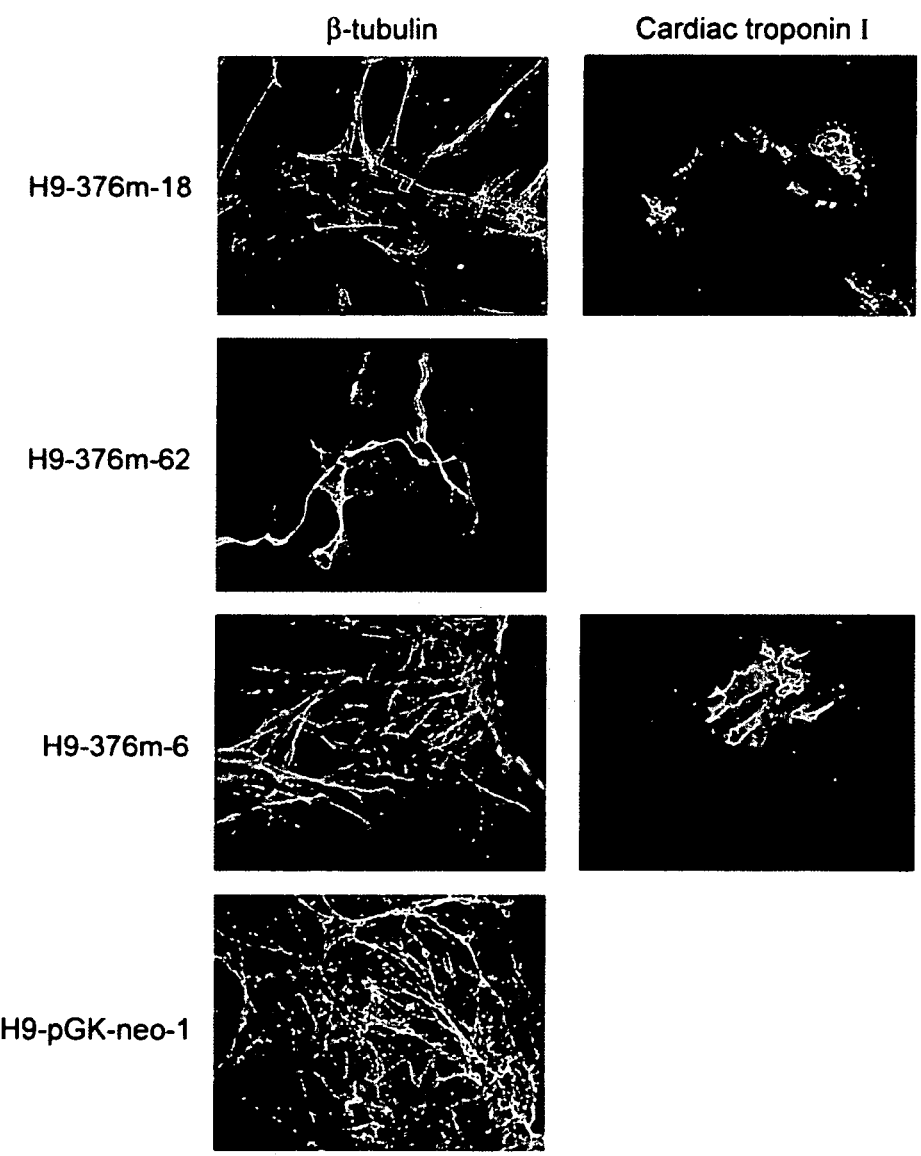

FIG. 12 shows representative fluorescence micrographs of immunocytochemistry. Results were as follows.

H9-376m-18 p 80+20 was able to generate large embryoid bodies (1 experiment). Beating areas (consistent with cardiomyocyte-lineage cells) were observed. Muscle-Specific Actin +++; α-fetoprotein +++; β-tubulin +++; cardiac troponin I +.

H9-376m-77 p 80+16 generated only small embryoid bodies (1 experiment). No beating areas were observed. Muscle-Specific Actin +; α-fetoprotein +β-tubulin- (none detected); cardiac troponin I −.

H9-376m-62 p 80+16, p 80+20, p 80+21, p 80+24 (4 experiments) were capable of generating only small embryoid bodies. No beating areas were observed. Muscle-Specific Actin ++; α-fetoprotein +; β-tubulin +; cardiac troponin I −.

H9-376m-6 p 24+12, p 24+13, p 24+21 (3 experiments) were able to generate large embryoid bodies, Many beating areas were observed in all experiments. Muscle-Specific Actin ++; α-fetoprotein ++; β-tubulin ++++; cardiac troponin I +.

H9-pGK-neo-1 p 24+9, p 24+10, p 24+13 (3 experiments) were able to generate large embryoid bodies, Beating areas were observed in 2 out of 3 experiments. β-tubulin +++; cardiac troponin I +; Muscle-Specific Actin ++++; α-fetoprotein ++.

The results of Examples 13-16 show that at least three of the stem cell lines containing the telomerase promoter driven thymidine kinase gene are capable of differentiating into cells of each of the three germ layers. Differentiated cells from these lines contain an important stop-gap against residual or reemerging undifferentiated cells. Ganciclovir at a concentration as low as 2.5 μM kills virtually all such modified undifferentiated ES cells within ~4 days.

Sequence Data

TABLE 3

| SEQ. ID NO: | Designation | Reference |
|---|---|---|
| 1 | Lambda clone designated λGφ5 (ATCC Accession No. 98505) | GenBank Accession AF121948 International Patent Publication WO 00/46355. |
| | Contains human Telomerase Reverse Transcriptase (hTERT) genomic insert (residues 44-15375). The ATG translation initiation site begins at residue 13545. | |
| 2 | Herpes simplex virus type 1 thymidine kinase and 3KBL gene sequence | GenBank Accession J02224 See also McKnight et al., Nucleic Acids Res. 8:5949 (1980); Wagner et al., Proc. Natl. Acad. Sci. U.S.A. 78:1441 (1981) |
| 3 | Herpes simplex virus type 1 thymidine kinase and 3KBL amino acid sequence | (supra) |
| 4-7 | Probes and Primers | (Artificial Sequences) |

It will be recognized that the compositions and procedures provided in the description can be effectively modified by those skilled in the art without departing from the spirit of the invention embodied in the claims that follow.

What is claimed as the invention is:

1. An isolated in vitro cell population comprising differentiated cells and less than 1% human embryonic stem (hES) cells, wherein the differentiated cells are the progeny of the hES cells, and wherein the differentiated cells and the hES cells comprise a nucleic acid molecule comprising the structure P-X,
   wherein X is a nucleic acid sequence encoding a product that is lethal to a cell in which it is expressed or renders a cell in which it is expressed susceptible to a lethal effect of an external agent, and
   wherein P is a transcriptional control element that is expressed in the hES cells and down regulated when the hES cells are induced to differentiate.

2. The cell population of claim 1, wherein X encodes a toxin, or a protein that induces or mediates apoptosis.

3. The cell population of claim 1, wherein X encodes an enzyme that converts a prodrug to a compound that is lethal to a cell in which X is expressed.

4. The cell of population claim 3, wherein X encodes a thymidine kinase.

5. The cell population of claim 1, wherein P-X is an introduced heterologous molecule.

6. The cell population of claim 1, wherein P is an endogenous transcriptional control element.

7. The cell population of claim 1, wherein P is an OCT 4 promoter or a promoter of telomerase reverse transcriptase (TERT).

8. The cell population of claim 1, wherein the differentiated cells are at least one of neurons, hepatocytes, and cardiomyocytes.

9. The cell population of claim 8, wherein the differentiated cells are neurons.

10. The cell population of claim 8, wherein the differentiated cells are hepatocytes.

11. The cell population of claim 8, wherein the differentiated cells are cardiomyocytes.

* * * * *

SEQUENCE LISTING

<160> NUMBER OF SEQ ID NOS: 7

<210> SEQ ID NO 1
<211> LENGTH: 15418
<212> TYPE: DNA
<213> ORGANISM: Homo sapiens

<400> SEQUENCE: 1

```
gcggccgcga gctctaatac gactcactat agggcgtcga ctcgatcaat ggaagatgag      60
gcattgccga agaaaagatt aatggatttg aacacacagc aacagaaact acatgaagtg     120
aaacacagga aaaaaaagat aaagaaacga aaagaaaagg gcatcagtga gcttcagcag     180
aagttccatc ggccttacat atgtgtaagc agaggccctg taggagcaga ggcagggggga    240 aaatacttta agaaataatg tctaaaagtt tttcaaatat gaggaaaaac ataaaaccac     300
agatccaaga agctcaacaa aacaaagcac aagaaacagg aagaaattaa aagttatatc     360
acagtcaaat tgctgaaaac cagcaacaaa gagaatatct taagagtatc agaggaaaag    420
agattaatga caggccaaga aacaatgaaa acaatacaga tttcttgtag gaaacacaag    480
acaaaagaca ttttttaaaa ccaaaaggaa aaaaaatgct acattaaaat gttttttacc     540
cactgaaagt atatttcaaa acatatttta ggccaggctt ggtggctcac acctgtaatc     600
ccagcacttt gggaggccaa ggtgggtgga tcgcttaagg tcaggagttc gagaccagcc     660
tggccaatat agcgaaaccc catctgtact aaaaacacaa aaattagctg ggtgtggtga     720
cacatgcctg taatcccagg tactcaggag gctaaggcag gagaattgct tgaactggga     780
ggcagaggtg gtgagccaag attgcaccag tgcactccag ccttggtgac agagtgaaac    840
tccatctcaa aaacaaacaa acaaaataca tatacataaa tatatatgca catatatata     900
catatataaa tatatataca catatataaa tctatataca tatatacata tatacacata    960
```

```
tataaatcta tatacatata tatacatata taatatattt acatatataa atatatacat    1020
atataaatat acatatataa atacatatat aaatatacat atataaatat acatatataa    1080
atatacatat ataaatatat acatatataa atacatatat ataaatatat atacatatat    1140
aaatatataa atatacaagt atatacaaat atatacatat ataaatgtat atacgtatat    1200
acatatatat ataaatatat aaaaaaactt ttggctgggc acctttccaa atctcatggc    1260
acatataagt ctcatggtaa cctcaaataa aaaaacatat aacagataca ccaaaaataa    1320
aaaccaataa attaaatcat gccaccagaa gaaattacct tcactaaaag gaacacagga    1380
aggaaagaaa gaaggaagag aagaccatga aacaaccaga aaacaaacaa caaaacagca    1440
ggagtaattc ctgacttatc aataataatg ctgggtgtaa atggactaaa ctctccaatc    1500
aaaagacata gagtggctga atggacgaaa aaaacaagac tcaataatct gttgcctaca    1560
agaatatact tcacctataa agggacacat agactgaaaa taaaaggaag gaaaaatatt    1620
ctatgcaaat ggaaaccaaa aaaagaacag aactagctac acttatatca gacaaaatag    1680
atttcaagac aaaaagtaca aaaagagaca aagtaattat ataataataa agcaaaaaga    1740
tataacaatt gtgaatttat atgcgcccaa cactgggaca cccagatata tacagcaaat    1800
attattagaa ctaaggagag agagagatcc ccatacaata atagctggag acttcaccccc    1860 gcttttagca ttggacagat catccagaca gaaaatcaac caaaaaattg gacttaatct    1920
ataatataga acaaatgtac ctaattgatg tttacaagac atttcatcca gtagttgcag    1980
aatatgcatt ttttcctcag catatggatc attctcaagg atagaccata tattaggcca    2040
cagaacaagc cattaaaaat tcaaaaaaat tgagccaggc atgatggctt atgcttgtaa    2100
ttacagcact ttggggaggg tgaggtggga ggatgtcttg agtacaggag tttgagacca    2160
gcctgggcaa aatagtgaga ccctgtctct acaaactttt ttttttaatt agccaggcat    2220
agtggtgtgt gcctgtagtc ccagctactt aggaggctga agtgggagga tcacttgagc    2280
ccaagagttc aaggctacgg tgagccatga ttgcaacacc acacaccagc cttggtgaca    2340
gaatgagacc ctgtctcaaa aaaaaaaaaa aaaattgaaa taatataaag catcttctct    2400
ggccacagtg gaacaaaacc agaaatcaac aacaagagga attttgaaaa ctatacaaac    2460
acatgaaaat taaacaatat acttctgaat aaccagtgag tcaatgaaga aattaaaaag    2520
gaaattgaaa aatttatttg agcaaatgat aacggaaaca taacctctca aaacccacgg    2580
tatacagcaa aagcagtgct aagaaggaag tttatagcta taagcagcta catcaaaaaa    2640
gtagaaaagc caggcgcagt ggctcatgcc tgtaatccca gcactttggg aggccaaggc    2700
gggcagatcg cctgaggtca ggagttcgag accagcctga ccaacacaga gaaaccttgt    2760
cgctactaaa aatacaaaat tagctgggca tggtggcaca tgcctgtaat cccagctact    2820
cgggaggctg aggcaggata accgcttgaa cccaggaggt ggaggttgcg gtgagccggg    2880
attgcgccat tggactccag cctgggtaac aagagtgaaa ccctgtctca agaaaaaaaa    2940
aaaagtagaa aaacttaaaa atacaaccta atgatgcacc ttaaagaact agaaaagcaa    3000 gagcaaaacta aacctaaaat tggtaaaaga aagaaataa taaagatcag agcagaaata    3060
aatgaaactg aaagataaca atacaaaaga tcaacaaaat taaaagttgg ttttttgaaa    3120
agataaacaa aattgacaaa cctttgccca gactaagaaa aaggaaaga agacctaaat    3180 aaataaagtc agagatgaaa aaagagacat tacaactgat accacagaaa ttcaaaggat    3240
cactagaggc tactatgagc aactgtacac taataaattg aaaaacctag aaaaaataga    3300
taaattccta gatgcataca acctaccaag attgaaccat gaagaaatcc aaagcccaaa    3360
```

| | |
|---|---|
| cagaccaata acaataatgg gattaaagcc ataataaaaa gtctcctagc aaagagaagc | 3420 |
| ccaggaccca atggcttccc tgctggattt taccaatcat ttaaagaaga atgaattcca | 3480 |
| atcctactca aactattctg aaaaatagag gaaagaatac ttccaaactc attctacatg | 3540 |
| gccagtatta ccctgattcc aaaaccagac aaaaacacat caaaaacaaa caaacaaaaa | 3600 |
| aacagaaaga aagaaaacta caggccaata tccctgatga atactgatac aaaaatcctc | 3660 |
| aacaaaacac tagcaaacca aattaaacaa caccttcgaa agatcattca ttgtgatcaa | 3720 |
| gtgggattta ttccagggat ggaaggatgg ttcaacatat gcaaatcaat caatgtgata | 3780 |
| catcatccca acaaaatgaa gtacaaaaac tatatgatta tttcactttta tgcagaaaaa | 3840 |
| gcatttgata aaattctgca cccttcatga taaaaaccct caaaaaacca ggtatacaag | 3900 |
| aaacatacag gccaggcaca gtggctcaca cctgcgatcc cagcactctg ggaggccaag | 3960 |
| gtgggatgat tgcttgggcc caggagtttg agactagcct gggcaacaaa atgagacctg | 4020 |
| gtctacaaaa aactttttta aaaaattagc caggcatgat ggcatatgcc tgtagtccca | 4080 |
| gctagtctgg aggctgaggt gggagaatca cttaagccta ggaggtcgag gctgcagtga | 4140 |
| gccatgaaca tgtcactgta ctccagccta gacaacagaa caagacccca ctgaataaga | 4200 |
| agaaggagaa ggagaaggga gaaaggaggg agaagggagg aggaggagaa ggaggaggtg | 4260 |
| gaggagaagt ggaaggggaa ggggaaggga aagaggaaga agaagaaaca tatttcaaca | 4320 |
| taataaaagc cctatatgac agaccgaggt agtattatga ggaaaaactg aaagcctttc | 4380 |
| ctctaagatc tggaaaatga caagggccca ctttcaccac tgtgattcaa catagtacta | 4440 |
| gaagtcctag ctagagcaat cagataagag aaagaaataa aaggcatcca aactggaaag | 4500 |
| gaagaagtca aattatcctg tttgcagatg atatgatctt atatctggaa aagacttaag | 4560 |
| acaccactaa aaaactatta gagctgaaat ttggtacagc aggatacaaa atcaatgtac | 4620 |
| aaaaatcagt agtatttcta tattccaaca gcaaacaatc tgaaaagaa accaaaaaag | 4680 |
| cagctacaaa taaaattaaa cagctaggaa ttaaccaaag aagtgaaaga tctctacaat | 4740 |
| gaaaactata aaatattgat aaaagaaatt gaagagggca caaaaaaaga aaagatattc | 4800 |
| catgttcata gattggaaga ataaatactg ttaaaatgtc catactaccc aaagcaattt | 4860 |
| acaaattcaa tgcaatccct attaaaatac taatgacgtt cttcacagaa atagaagaaa | 4920 |
| caattctaag atttgtacag aaccacaaaa gacccagaat agccaaagct atcctgacca | 4980 |
| aaaagaacaa aactggaagc atcacattac ctgacttcaa attatactac aaagctatag | 5040 |
| taacccaaac tacatggtac tggcataaaa acagatgaga catggaccag aggaacagaa | 5100 |
| tagagaatcc agaaacaaat ccatgcatct acagtgaact cattttttgac aaaggtgcca | 5160 |
| agaacatact ttggggaaaa gataatctct tcaataaatg gtgctggagg aactggatat | 5220 |
| ccatatgcaa ataacaata ctagaactct gtctctcacc atatacaaaa gcaaatcaaa | 5280 |
| atggatgaaa ggcttaaatc taaaacctca aactttgcaa ctactaaaag aaaacaccgg | 5340 |
| agaaactctc caggacattg gagtgggcaa agacttcttg agtaattccc tgcaggcaca | 5400 |
| ggcaaccaaa gcaaaacag acaaatggga tcatatcaag ttaaaaagct tctgcccagc | 5460 |
| aaaggaaaca atcaacaaag agaagagaca acccacagaa tgggagaata tatttgcaaa | 5520 |
| ctattcatct aacaaggaat taataaccag tatatataag gagctcaaac tactctataa | 5580 |
| gaaaacacc taataagctg attttcaaaa ataagcaaaa gatctgggta gacatttctc | 5640 |
| aaaataagtc atacaaatgg caaacaggca tctgaaaatg tgctcaacac cactgatcat | 5700 |
| cagagaaatg caaatcaaaa ctactatgag agatcatctc accccagtta aaatggcttt | 5760 |

-continued

```
tattcaaaag acaggcaata acaaatgcca gtgaggatgt ggataaaagg aaacccttgg    5820
acactgttgg tgggaatgga aattgctacc actatggaga acagtttgaa agttcctcaa    5880
aaaactaaaa ataaagctac catacagcaa tcccattgct aggtatatac tccaaaaaag    5940
ggaatcagtg tatcaacaag ctatctccac tcccacattt actgcagcac tgttcatagc    6000
agccaaggtt tggaagcaac ctcagtgtcc atcaacagac gaatggaaaa agaaaatgtg    6060
gtgcacatac acaatggagt actacgcagc cataaaaaag aatgagatcc tgtcagttgc    6120
aacagcatgg ggggcactgg tcagtatgtt aagtgaaata agccaggcac agaaagacaa    6180
acttttcatg ttctcccctta cttgtgggag caaaaattaa acaattgac atagaaatag    6240
aggagaatgg tggttctaga ggggtggggg acagggtgac tagagtcaac aataatttat    6300
tgtatgtttt aaaataacta aaagagtata attgggttgt ttgtaacaca agaaaaggat    6360
aaatgcttga aggtgacaga tacccccattt accctgatgt gattattaca cattgtatgc    6420
ctgtatcaaa atatctcatg tatgctatag atataaaccc tactatatta aaaattaaaa    6480
ttttaatggc caggcacggt ggctcatgtc cataatccca gcactttggg aggccgaggc    6540
ggtggatcac ctgaggtcag gagtttgaaa ccagtctggc caccatgatg aaaccctgtc    6600
tctactaaag atacaaaaat tagccaggcg tggtggcaca tacctgtagt cccaactact    6660
caggaggctg agacaggaga attgcttgaa cctgggaggc ggaggttgca gtgagccgag    6720
atcatgccac tgcactgcag cctgggtgac agagcaagac tccatctcaa aacaaaaaca    6780
aaaaaagaa gattaaaatt gtaattttta tgtaccgtat aaatatatac tctactatat    6840
tagaagttaa aaattaaaac aattataaaa ggtaattaac cacttaatct aaaataagaa    6900
caatgtatgt gggggtttcta gcttctgaag aagtaaaagt tatggccacg atggcagaaa    6960
tgtgaggagg gaacagtgga agttactgtt gttagacgct catactctct gtaagtgact    7020
taattttaac caaagacagg ctgggagaag ttaaagaggc attctataag ccctaaaaca    7080
actgctaata atggtgaaag gtaatctcta ttaattacca ataattacag atatctctaa    7140
aatcgagctg cagaattggc acgtctgatc acaccgtcct ctcattcacg gtgcttttt    7200
tcttgtgtgc ttggagattt tcgattgtgt gttcgtgttt ggttaaactt aatctgtatg    7260
aatcctgaaa cgaaaatgg tggtgatttc ctccagaaga attagagtac ctggcaggaa    7320
gcaggtggct ctgtggacct gagccacttc aatcttcaag ggtctctggc caagacccag    7380
gtgcaaggca gaggcctgat gacccgagga caggaaagct cggatgggaa ggggcgatga    7440
gaagcctgcc tcgttggtga gcagcgcatg aagtgcccct atttacgctt tgcaaagatt    7500
gctctggata ccatctggaa aaggcggcca gcgggaatgc aaggagtcag aagcctcctg    7560
ctcaaaccca ggccagcagc tatggcgccc acccggcgt gtgccagagg gagaggagtc    7620
aaggcacctc gaagtatggc ttaaatctttt ttttcacctg aagcagtgac caaggtgtat    7680
tctgagggaa gcttgagtta ggtgccttct ttaaaacaga aagtcatgga agcacccttc    7740
tcaagggaaa accagacgcc cgctctgcgg tcatttacct ctttcctctc tccctctctt    7800
gccctcgcgg tttctgatcg ggacagagtg accccgtgg agcttctccg agccgtgct    7860
gaggaccctc ttgcaaaggg ctccacagac ccccgccctg gagagaggag tctgagcctg    7920
gcttaataac aaactgggat gtggctgggg cggacagcg acggcgggat tcaaagactt    7980
aattccatga gtaaattcaa ccttttccaca tccgaatgga tttggatttt atcttaatat    8040
tttcttaaat ttcatcaaat aacattcagg agtgcagaaa tccaaaggcg taaaacagga    8100
actgagctat gtttgccaag gtccaaggac ttaataacca tgttcagagg gattttttcgc    8160
```

```
cctaagtact tttattggt ttcataagg tggcttaggg tgcaagggaa agtacacgag    8220
gagaggactg ggcggcaggg ctatgagcac ggcaaggcca ccggggagag agtccccggc    8280
ctgggaggct gacagcagga ccactgaccg tcctccctgg gagctgccac attgggcaac    8340
gcgaaggcgg ccacgctgcg tgtgactcag gaccccatac cggcttcctg ggcccaccca    8400
cactaaccca ggaagtcacg gagctctgaa cccgtggaaa cgaacatgac ccttgcctgc    8460
ctgcttccct gggtgggtca agggtaatga agtggtgtgc aggaaatggc catgtaaatt    8520
acacgactct gctgatgggg accgttcctt ccatcattat tcatcttcac ccccaaggac    8580
tgaatgattc cagcaacttc ttcgggtgtg acaagccatg acaacactca gtacaaacac    8640
cactctttta ctaggcccac agagcacggc ccacacccct gatatattaa gagtccagga    8700
gagatgaggc tgctttcagc caccaggctg gggtgacaac agcggctgaa cagtctgttc    8760
ctctagacta gtagaccctg gcaggcactc ccccagattc tagggcctgg ttgctgcttc    8820
ccgagggcgc catctgccct ggagactcag cctggggtgc cacactgagg ccagccctgt    8880
ctccacaccc tccgcctcca ggcctcagct tctccagcag cttcctaaac cctgggtggg    8940
ccgtgttcca gcgctactgt ctcacctgtc ccactgtgtc ttgtctcagc gacgtagctc    9000
gcacggttcc tcctcacatg gggtgtctgt ctccttcccc aacactcaca tgcgttgaag    9060
ggaggagatt ctgcgcctcc cagactggct cctctgagcc tgaacctggc tcgtggcccc    9120
cgatgcaggt tcctggcgtc cggctgcacg ctgacctcca tttccaggcg ctccccgtct    9180
cctgtcatct gccggggcct gccgtgtgt cttctgttt ctgtgctcct ttccacgtcc    9240
agctgcgtgt gtctctgtcc gctagggtct cggggttttt ataggcatag gacggggggcg    9300 tggtgggcca gggcgctctt gggaaatgca acatttgggt gtgaaagtag gagtgcctgt    9360
cctcacctag gtccacgggc acaggcctgg ggatggagcc cccgccaggg acccgccctt    9420
ctctgcccag cacttttctg ccccccctccc tctggaacac agagtggcag tttccacaag    9480
cactaagcat cctcttccca aaagacccag cattggcacc cctggacatt tgccccacag    9540
ccctgggaat tcacgtgact acgcacatca tgtacacact cccgtccacg accgacccc    9600 gctgttttat tttaatagct acaaagcagg gaaatccctg ctaaaatgtc ctttaacaaa    9660
ctggttaaac aaacgggtcc atccgcacgg tggacagttc ctcacagtga agaggaacat    9720
gccgtttata aagcctgcag gcatctcaag ggaattacgc tgagtcaaaa ctgccacctc    9780
catgggatac gtacgcaaca tgctcaaaaa gaaagaattt caccccatgg caggggagtg    9840 gttgggggt taaggacggt gggggcagca gctgggggct actgcacgca ccttttacta    9900
aagccagttt cctggttctg atggtattgg ctcagttatg ggagactaac catagggggag    9960 tgggatggg gaacccgga ggctgtgcca tcttgcccat gccgagtgt cctgggcagg   10020 ataatgctct agagatgccc acgtcctgat tcccccaaac ctgtggacag aacccgcccg   10080
gccccagggc ctttgcaggt gtgatctccg tgaggaccct gaggtctggg atccttcgg   10140 actacctgca ggcccgaaaa gtaatccagg ggttctggga agaggcgggc aggagggtca   10200 gagggggca gcctcaggac gatggaggca gtcagtctga ggctgaaaag ggagggaggg   10260
cctcgagccc aggcctgcaa gcgcctccag aagctggaaa aagcggggaa gggaccctcc   10320
acggagcctg cagcaggaag gcacggctgg cccttagccc accagggccc atcgtggacc   10380
tccggcctcc gtgccatagg agggcactcg cgctgcccctt ctagcatgaa gtgtgtgggg   10440 attgcagaa gcaacaggaa acccatgcac tgtgaatcta ggattatttc aaaacaaagg   10500
tttacagaaa catccaagga cagggctgaa gtgcctccgg gcaaggggcag ggcaggcacg   10560
```

```
agtgatttta tttagctatt ttattttatt tacttacttt ctgagacaga gttatgctct   10620
tgttgcccag gctggagtgc agcggcatga tcttggctca ctgcaacctc cgtctcctgg   10680
gttcaagcaa ttctcgtgcc tcagcctccc aagtagctgg gatttcaggc gtgcaccacc   10740
acacccggct aattttgtat ttttagtaga gatgggcttt caccatgttg gtcaggctga   10800
tctcaaaatc ctgacctcag gtgatccgcc cacctcagcc tcccaaagtg ctgggattac   10860
aggcatgagc cactgcacct ggcctattta accatttaa aacttccctg gctcaagtc    10920
acacccactg gtaaggagtt catggagttc aatttcccct ttactcagga gttaccctcc   10980
tttgatattt tctgtaattc ttcgtagact ggggatacac cgtctcttga catattcaca   11040
gtttctgtga ccacctgtta tcccatggga cccactgcag gggcagctgg gaggctgcag   11100
gcttcaggtc ccagtggggt tgccatctgc cagtagaaac ctgatgtaga atcagggcgc   11160
gagtgtggac actgtcctga atctcaatgt ctcagtgtgt gctgaaacat gtagaaatta   11220
aagtccatcc ctcctactct actgggattg agccccttcc ctatcccccc ccaggggcag   11280
aggagttcct ctcactcctg tgaggaagg aatgatactt tgttattttt cactgctggt    11340
actgaatcca ctgttcatt tgttggtttg tttgttttgt tttgagaggc ggtttcactc    11400
ttgttgctca ggctggaggg agtgcaatgg cgcgatcttg gcttactgca gcctctgcct   11460
cccaggttca agtgattctc ctgcttccgc ctcccatttg gctgggatta caggcacccg   11520
ccaccatgcc cagctaattt tttgtatttt tagtagagac gggggtgggg gtggggttca   11580
ccatgttggc caggctggtc tcgaacttct gacctcagat gatccacctg cctctgcctc   11640
ctaaagtgct gggattacag gtgtgagcca ccatgcccag ctcagaattt actctgttta   11700
gaaacatctg ggtctgaggt aggaagctca ccccactcaa gtgttgtggt gttttaagcc   11760
aatgatagaa ttttttatt gttgttagaa cactcttgat gttttacact gtgatgacta    11820
agacatcatc agcttttcaa agacacacta actgcaccca taatactggg gtgtcttctg   11880
ggtatcagcg atcttcattg aatgccggga ggcgtttcct cgccatgcac atggtgttaa   11940
ttactccagc ataatcttct gcttccattt cttctcttcc ctcttttaaa attgtgtttt   12000
ctatgttggc ttctctgcag agaaccagtg taagctacaa cttaactttt gttggaacaa   12060
attttccaaa ccgccccttt gccctagtgg cagagacaat tcacaaacac agcccttaa    12120
aaaggcttag ggatcactaa ggggatttct agaagagcga cccgtaatcc taagtattta   12180
caagacgagg ctaacctcca gcgagcgtga cagcccaggg agggtgcgag gcctgttcaa   12240
atgctagctc cataaataaa gcaatttcct ccggcagttt ctgaaagtag gaaaggttac   12300
atttaaggtt gcgtttgtta gcatttcagt gtttgccgac ctcagctaca gcatccctgc   12360
aaggcctcgg gagacccaga gtttctcgc cccttagatc caaacttgag caaccccgag    12420
tctggattcc tgggaagtcc tcagctgtcc tgcggttgtg ccggggcccc aggtctggag   12480
gggaccagtg gccgtgtggc ttctactgct gggctggaag tcgggcctcc tagctctgca   12540
gtccgaggct tggagccagg tgcctggacc ccgaggctgc cctccaccct gtgcgggcgg   12600
gatgtgacca gatgttggcc tcatctgcca gacagagtgc cggggcccag ggtcaaggcc   12660
gttgtggctg gtgtgaggcg cccggtgcgc ggccagcagg agcgcctggc tccatttccc   12720
accctttctc gacgggaccg ccccggtggg tgattaacag atttgggtg gtttgctcat    12780
ggtggggacc cctcgccgcc tgagaacctg caaagagaaa tgacgggcct gtgtcaagga   12840
gcccaagtcg cggggaagtg ttgcaggag gcactccggg aggtcccgcg tgcccgtcca    12900
gggagcaatg cgtcctcggg ttcgtcccca gccgcgtcta cgcgcctccg tcctcccctt   12960
```

```
cacgtccggc attcgtggtg cccggagccc gacgccccgc gtccggacct ggaggcagcc   13020
ctgggtctcc ggatcaggcc agcggccaaa gggtcgccgc acgcacctgt cccagggcc    13080
tccacatcat ggcccctccc tcgggttacc ccacagccta ggccgattcg acctctctcc   13140
gctggggccc tcgctggcgt ccctgcaccc tgggagcgcg agcggcgcgc gggcggggaa   13200
gcgcggccca gaccccgggt ccgcccggag cagctgcgc tgtcggggcc aggccgggct    13260
cccagtggat tcgcgggcac agacgcccag gaccgcgctt ccacgtggc ggagggactg    13320
gggacccggg cacccgtcct gcccttcac cttccagctc cgcctcctcc gcgcggaccc    13380
cgccccgtcc cgacccctcc cgggtccccg gccagcccc ctccgggccc tccagcccc     13440
tcccttcct ttccgcggcc ccgccctctc ctcgcggcgc gagtttcagg cagcgctgcg    13500
tcctgctgcg cacgtgggaa gccctggccc cggccacccc cgcgatgccg cgcgctcccc   13560
gctgccgagc cgtgcgctcc ctgctgcgca gccactaccg cgaggtgctg ccgctggcca   13620
cgttcgtgcg gcgcctgggg ccccaggggct ggcggctggt gcagcgcggg gacccggcgg  13680
cttccgcgc gctggtggcc cagtgcctgg tgtgcgtgcc ctgggacgca cggccgcccc    13740
ccgccgcccc ctccttccgc caggtgggcc tccccgggggt cggcgtccgg ctggggttga  13800
gggcggccgg ggggaaccag cgacatgcgg agagcagcgc aggcgactca gggcgcttcc   13860
cccgcaggtg tcctgcctga aggagctggt ggcccgagtg ctgcagaggc tgtgcgagcg   13920
cggcgcgaag aacgtgctgg ccttcggctt cgcgctgctg gacggggccc gcgggggccc   13980
ccccgaggcc ttcaccacca gcgtgcgcag ctacctgccc aacacggtga ccgacgcact   14040
gcggggagc ggggcgtggg ggctgctgct gcgccgcgtg ggcgacgacg tgctggttca    14100
cctgctggca cgctgcgcgc tctttgtgct ggtggctccc agctgcgcct accaggtgtg   14160
cgggccgccg ctgtaccagc tcggcgctgc cactcaggcc cggcccccgc cacacgctag   14220
tggaccccga aggcgtctgg gatgcgaacg ggcctggaac catagcgtca gggaggccgg   14280
ggtccccctg ggcctgccag ccccgggtgc gaggaggcgc gggggcagtg ccagccgaag   14340
tctgccgttg cccaagaggc ccaggcgtgg cgctgcccct gagccggagc ggacgcccgt   14400
tgggcagggg tcctgggccc acccgggcag gacgcgtgga ccgagtgacc gtggtttctg   14460
tgtggtgtca cctgccagac ccgccgaaga agccacctct ttggagggtg cgctctctgg   14520
cacgcgccac tcccacccat ccgtgggccg ccagcaccac gcgggccccc catccacatc   14580
gcggccacca cgtccctggg acacgccttg tccccggtg tacgccgaga ccaagcactt    14640
cctctactcc tcaggcgaca aggagcagct gcggccctcc ttcctactca gctctctgag   14700
gcccagcctg actggcgctc ggaggctcgt ggagaccatc tttctgggtt ccaggccctg   14760
gatgccaggg actccccgca ggttgccccg cctgccccag cgctactggc aaatgcggcc   14820
cctgtttctg gagctgcttg gaaccacgc gcagtgcccc tacggggtgc tcctcaagac    14880
gcactgcccg ctgcgagctg cggtcacccc agcagccggt gtctgtgccc gggagaagcc   14940
ccagggctct gtggcggccc ccgaggagga ggacacagac cccgtcgcc tggtgcagct    15000
gctccgccag cacagcagcc cctggcaggt gtacggcttc gtgcgggcct gcctgcgccg   15060
gctggtgccc ccaggcctct ggggctccag gcacaacgaa cgccgcttcc tcaggaacac   15120
caagaagttc atctccctgg ggaagcatgc caagctctcg ctgcaggagc tgacgtggaa   15180
gatgagcgtg cgggactgcg cttggctgcg caggagccca ggtgaggagg tggtggccgt   15240
cgagggccca ggcccagag ctgaatgcag taggggctca gaaaagggg caggcagagc     15300
cctggtcctc ctgtctccat cgtcacgtgg gcacacgtgg cttttcgctc aggacgtcga   15360
```

| | |
|---|---:|
| gtggacacgg tgatcgagtc gactcccttt agtgagggtt aattgagctc gcggccgc | 15418 |

<210> SEQ ID NO 2
<211> LENGTH: 2403
<212> TYPE: DNA
<213> ORGANISM: Herpes simplex virus type 1

<400> SEQUENCE: 2

| | |
|---|---:|
| gggtcctagg ctccatgggg accgtatacg tggacaggct ctggagcatc gcacgactgc | 60 |
| gtgatattac cggagacctt ctgcgggacg agccgggtca cgcggctgac ggagcgtccg | 120 |
| ttgggcgaca acaccagga cggggcacag gtacactatc ttgtcacccg gagcgcgagg | 180 |
| gactgcagga gcttcaggga gtggcgcagc tgcttcatcc ccgtggcccg ttgctcgcgt | 240 |
| ttgctggcgt tgtccccgga agaaatatat ttgcatgtct ttagttctat gatgacacaa | 300 |
| accccgccca gcgtcttgtc attggcgaat cgaacacgc agatgcagtc ggggcggcgc | 360 |
| ggtcccaggt ccacttcgca tattaaggtg acgcgtgtgg cctcgaacac cgagcgaccc | 420 |
| tgcagcgacc cgcttaacag cgtcaacagc gtgccgcaga tcttggtggc gtgaaactcc | 480 |
| cgcacctctt tggcaagcgc cttgtagaag cgcgtatggc ttcgtacccc tgccatcaac | 540 |
| acgcgtctgc gttcgaccag gctgcgcgtt ctcgcggcca tagcaaccga cgtacggcgt | 600 |
| tgcgccctcg ccggcagcaa gaagccacgg aagtccgcct ggagcagaaa atgcccacgc | 660 |
| tactgcgggt ttatatagac ggtcctcacg ggatggggaa accaccacc acgcaactgc | 720 |
| tggtggccct gggttcgcgc gacgatatcg tctacgtacc cgagccgatg acttactggc | 780 |
| aggtgctggg ggcttccgag acaatcgcga acatctacac cacacaacac cgcctcgacc | 840 |
| agggtgagat atcggccggg gacgcggcgg tggtaatgac aagcgcccag ataacaatgg | 900 |
| gcatgcctta tgccgtgacc gacgccgttc tggctcctca tgtcgggggg gaggctggga | 960 |
| gttcacatgc cccgccccg gccctcaccc tcatcttcga ccgccatccc atcgccgccc | 1020 |
| tcctgtgcta cccggccgcg cgataccttta tgggcagcat gaccccccag gccgtgctgg | 1080 |
| cgttcgtggc cctcatcccg ccgaccttgc ccggcacaaa catcgtgttg ggggcccttc | 1140 |
| cggaggacag acacatcgac cgcctggcca aacgccagcg ccccggcgag cggcttgacc | 1200 |
| tggctatgct ggccgcgatt cgccgcgttt acgggctgct tgccaatacg gtgcggtatc | 1260 |
| tgcagggcg cgggtcgtgg tgggaggatt ggggacagct ttcggggacg gccgtgccgc | 1320 |
| cccagggtgc cgagcccag agcaacgcgg gcccacgacc ccatatcggg gacacgttat | 1380 |
| ttaccctgtt tcgggccccc gagttgctgg ccccaacgg cgacctgtat aacgtgtttg | 1440 |
| cctgggcctt ggacgtcttg gccaaacgcc tccgtcccat gcacgtcttt atcctggatt | 1500 |
| acgaccaatc gcccgccggc tgccgggacg ccctgctgca acttacctcc gggatggtcc | 1560 |
| agacccacgt caccaccca ggctccatac cgacgatctg cgacctggcg cgcacgtttg | 1620 |
| cccgggagat gggggaggct aactgaaaca cggaaggaga caataccgga aggaacccgc | 1680 |
| gctatgacgg caataaaaag acagaataaa acgcacgggt gttgggtcgt tgttcataa | 1740 |
| acgcggggtt cggtcccagg gctggcactc tgtcgatacc ccaccgagac cccattgggg | 1800 |
| ccaatacgcc cgcgtttctt ccttttcccc accccaaccc caagttcgg gtgaaggccc | 1860 |
| agggctcgca gccaacgtcg gggcggcaag cccgccatag ccacgggccc cgtgggttag | 1920 |
| ggacggggtc cccatgggg aatggtttat ggttcgtggg ggttattctt ttgggcgttg | 1980 |
| cgtggggtca ggtccacgac tggactgagc agacagaccc atggtttttg gatggcctgc | 2040 |
| gcatggaccg catgtactgg cgcgacacga acaccgggcg tctgtggctg ccaaacaccc | 2100 |

-continued

```
ccgacccca aaaaccaccg cgcggatttc tggcgccgcc ggacgaacta aacctgacta      2160
cggcatctct gccccttctt cgctggtacg aggagcgctt tgttttgta ttggtcacca      2220 cggccgagtt tccgcgggac cccggccagc tgctttacat ctcgaagacc tacctactcg    2280 gccggcccc gaacgcgagc ctgccgccc catcacggt cgagccgacc gcccagcctc        2340
cccccgcggt cgcccccctt aagggtctct tgcacaatcc aaccgcctcc gtgttgctgc    2400
gtt                                                                   2403
```

<210> SEQ ID NO 3
<211> LENGTH: 376
<212> TYPE: PRT
<213> ORGANISM: Herpes simplex virus type 1

<400> SEQUENCE: 3

| | | | | | | | | | | | | | | | |
|---|---|---|---|---|---|---|---|---|---|---|---|---|---|---|---|
| Met | Ala | Ser | Tyr | Pro | Cys | His | Gln | His | Ala | Ser | Ala | Phe | Asp | Gln | Ala |
| 1 | | | | 5 | | | | | 10 | | | | | 15 | |
| Ala | Arg | Ser | Arg | Gly | His | Ser | Asn | Arg | Arg | Thr | Ala | Leu | Arg | Pro | Arg |
| | | | 20 | | | | | 25 | | | | | 30 | | |
| Arg | Gln | Gln | Glu | Ala | Thr | Glu | Val | Arg | Leu | Glu | Gln | Lys | Met | Pro | Thr |
| | | 35 | | | | | 40 | | | | | 45 | | | |
| Leu | Leu | Arg | Val | Tyr | Ile | Asp | Gly | Pro | His | Gly | Met | Gly | Lys | Thr | Thr |
| | 50 | | | | | 55 | | | | | 60 | | | | |
| Thr | Thr | Gln | Leu | Leu | Val | Ala | Leu | Gly | Ser | Arg | Asp | Asp | Ile | Val | Tyr |
| 65 | | | | | 70 | | | | | 75 | | | | | 80 |
| Val | Pro | Glu | Pro | Met | Thr | Tyr | Trp | Gln | Val | Leu | Gly | Ala | Ser | Glu | Thr |
| | | | | 85 | | | | | 90 | | | | | 95 | |
| Ile | Ala | Asn | Ile | Tyr | Thr | Thr | Gln | His | Arg | Leu | Asp | Gln | Gly | Glu | Ile |
| | | | 100 | | | | | 105 | | | | | 110 | | |
| Ser | Ala | Gly | Asp | Ala | Ala | Val | Val | Met | Thr | Ser | Ala | Gln | Ile | Thr | Met |
| | | 115 | | | | | 120 | | | | | 125 | | | |
| Gly | Met | Pro | Tyr | Ala | Val | Thr | Asp | Ala | Val | Leu | Ala | Pro | His | Val | Gly |
| | 130 | | | | | 135 | | | | | 140 | | | | |
| Gly | Glu | Ala | Gly | Ser | Ser | His | Ala | Pro | Pro | Ala | Leu | Thr | Leu | Ile |
| 145 | | | | | 150 | | | | | 155 | | | | | 160 |
| Phe | Asp | Arg | His | Pro | Ile | Ala | Ala | Leu | Leu | Cys | Tyr | Pro | Ala | Ala | Arg |
| | | | | 165 | | | | | 170 | | | | | 175 | |
| Tyr | Leu | Met | Gly | Ser | Met | Thr | Pro | Gln | Ala | Val | Leu | Ala | Phe | Val | Ala |
| | | | 180 | | | | | 185 | | | | | 190 | | |
| Leu | Ile | Pro | Pro | Thr | Leu | Pro | Gly | Thr | Asn | Ile | Val | Leu | Gly | Ala | Leu |
| | | 195 | | | | | 200 | | | | | 205 | | | |
| Pro | Glu | Asp | Arg | His | Ile | Asp | Arg | Leu | Ala | Lys | Arg | Gln | Arg | Pro | Gly |
| | 210 | | | | | 215 | | | | | 220 | | | | |
| Glu | Arg | Leu | Asp | Leu | Ala | Met | Leu | Ala | Ala | Ile | Arg | Arg | Val | Tyr | Gly |
| 225 | | | | | 230 | | | | | 235 | | | | | 240 |
| Leu | Leu | Ala | Asn | Thr | Val | Arg | Tyr | Leu | Gln | Gly | Gly | Gly | Ser | Trp | Trp |
| | | | | 245 | | | | | 250 | | | | | 255 | |
| Glu | Asp | Trp | Gly | Gln | Leu | Ser | Gly | Thr | Ala | Val | Pro | Pro | Gln | Gly | Ala |
| | | | 260 | | | | | 265 | | | | | 270 | | |
| Glu | Pro | Gln | Ser | Asn | Ala | Gly | Pro | Arg | Pro | His | Ile | Gly | Asp | Thr | Leu |
| | | 275 | | | | | 280 | | | | | 285 | | | |
| Phe | Thr | Leu | Phe | Arg | Ala | Pro | Glu | Leu | Leu | Ala | Pro | Asn | Gly | Asp | Leu |
| | 290 | | | | | 295 | | | | | 300 | | | | |
| Tyr | Asn | Val | Phe | Ala | Trp | Ala | Leu | Asp | Val | Leu | Ala | Lys | Arg | Leu | Arg |
| 305 | | | | | 310 | | | | | 315 | | | | | 320 |

```
Pro Met His Val Phe Ile Leu Asp Tyr Asp Gln Ser Pro Ala Gly Cys
            325                 330                 335

Arg Asp Ala Leu Leu Gln Leu Thr Ser Gly Met Val Gln Thr His Val
            340                 345                 350

Thr Thr Pro Gly Ser Ile Pro Thr Ile Cys Asp Leu Ala Arg Thr Phe
            355                 360                 365

Ala Arg Glu Met Gly Glu Ala Asn
        370                 375

<210> SEQ ID NO 4
<211> LENGTH: 25
<212> TYPE: DNA
<213> ORGANISM: Artificial
<220> FEATURE:
<223> OTHER INFORMATION: DNA/RNA

<400> SEQUENCE: 4
cttgctgcag aagtgggtgg aggaa                                          25

<210> SEQ ID NO 5
<211> LENGTH: 21
<212> TYPE: DNA
<213> ORGANISM: Artificial
<220> FEATURE:
<223> OTHER INFORMATION: DNA/RNA

<400> SEQUENCE: 5
ctgcagtgtg ggtttcgggc a                                              21

<210> SEQ ID NO 6
<211> LENGTH: 20
<212> TYPE: DNA
<213> ORGANISM: Artificial
<220> FEATURE:
<223> OTHER INFORMATION: DNA/RNA

<400> SEQUENCE: 6
cggaagagtg tctggagcaa                                                20

<210> SEQ ID NO 7
<211> LENGTH: 19
<212> TYPE: DNA
<213> ORGANISM: Artificial
<220> FEATURE:
<223> OTHER INFORMATION: DNA/RNA

<400> SEQUENCE: 7
ggatgaagcg gagtctgga                                                 19
```